(12) United States Patent
Friend et al.

(10) Patent No.: US 8,956,396 B1
(45) Date of Patent: \*Feb. 17, 2015

(54) EYE-TRACKING VISUAL PROSTHETIC AND METHOD

(75) Inventors: Michael E. Friend, Seattle, WA (US); Yongdan Hu, Bothell, WA (US); Charles A. Lemaire, Bothell, WA (US)

(73) Assignee: Lockheed Martin Corporation, Bethesda, MD (US)

( \* ) Notice: Subject to any disclaimer, the term of this patent is extended or adjusted under 35 U.S.C. 154(b) by 0 days.

This patent is subject to a terminal disclaimer.

(21) Appl. No.: 13/525,270

(22) Filed: Jun. 15, 2012

Related U.S. Application Data

(60) Provisional application No. 61/514,894, filed on Aug. 3, 2011.

(51) Int. Cl.
*A61N 5/067* (2006.01)
*A61N 5/06* (2006.01)

(52) U.S. Cl.
CPC .............. *A61N 5/0622* (2013.01); *A61N 5/06* (2013.01); *A61N 2005/0659* (2013.01); *A61N 2005/067* (2013.01)
USPC .............................................. 607/89; 607/88

(58) Field of Classification Search
USPC ................................. 607/53–54; 623/6.11, 22
See application file for complete search history.

(56) References Cited

U.S. PATENT DOCUMENTS 3,866,249 A \* 2/1975 Flom ............................ 623/6.12
4,064,872 A 12/1977 Caplan
4,215,694 A 8/1980 Isakov et al.
4,296,995 A 10/1981 Bickel
4,400,590 A 8/1983 Michelson
4,504,970 A 3/1985 Werth et al.

(Continued)

FOREIGN PATENT DOCUMENTS

WO       WO 0025112        5/2000
WO       WO 2010006049     1/2010

(Continued)

OTHER PUBLICATIONS

Dummer et al., Development of VCSELs for Optical Nerve Stimulation, Proc. SPIE 7883, Photonic Therapeutics and Diagnostics VII, 788351 (Feb. 17, 2011).\*

(Continued)

*Primary Examiner* — Lynsey Crandall
*Assistant Examiner* — Manolis Pahakis
(74) *Attorney, Agent, or Firm* — Charles A. Lemaire; Jonathan M. Rixen; Lemaire Patent Law Firm, P.L.L.C.

(57) ABSTRACT

An improved prosthesis and method for stimulating vision nerves to obtain a vision sensation that is useful for the patient that has lost vision due to AMD, RP, and other diseases. The invention utilizes infrared light to cause action potentials in the retinal nerves similar to those which result from rods and cones stimulated by visible light in healthy retinas. In some embodiments, the invention provides a prosthesis that generates a stimulation pattern of infrared light from an external stimulator array through the eye and focusing the stimulation pattern of infrared light on the retina, especially the fovea. Some embodiments the invention provides improved resolution down to a group of nerves, or even the individual nerve level, with sufficient energy density so as to cause a desired action potential.

25 Claims, 13 Drawing Sheets

(56) References Cited

U.S. PATENT DOCUMENTS

| | | | |
|---|---|---|---|
| 4,541,115 A | 9/1985 | Werth | |
| 4,550,431 A | 10/1985 | Werth et al. | |
| 4,551,850 A | 11/1985 | Werth et al. | |
| 4,558,703 A | 12/1985 | Mark | |
| 4,566,935 A | 1/1986 | Hornbeck | |
| 4,596,992 A | 6/1986 | Hornbeck | |
| 4,628,933 A * | 12/1986 | Michelson | 607/53 |
| 4,671,285 A | 6/1987 | Walker | |
| 4,681,791 A | 7/1987 | Shibahashi et al. | |
| 4,720,189 A | 1/1988 | Heynen et al. | |
| 4,724,835 A | 2/1988 | Liss et al. | |
| 4,757,515 A | 7/1988 | Hughes | |
| 4,768,516 A | 9/1988 | Stoddart et al. | |
| 4,813,418 A | 3/1989 | Harris | |
| 4,840,485 A | 6/1989 | Gratton | |
| 4,928,695 A | 5/1990 | Goldman et al. | |
| 4,930,504 A | 6/1990 | Diamantopoulos et al. | |
| 4,972,331 A | 11/1990 | Chance | |
| 4,989,605 A | 2/1991 | Rossen | |
| 5,062,428 A | 11/1991 | Chance | |
| 5,088,493 A | 2/1992 | Giannini et al. | |
| 5,109,844 A * | 5/1992 | de Juan et al. | 607/53 |
| 5,122,974 A | 6/1992 | Chance | |
| 5,139,025 A | 8/1992 | Lewis et al. | |
| 5,150,704 A | 9/1992 | Tatebayashi et al. | |
| 5,151,909 A | 9/1992 | Davenport et al. | |
| 5,152,278 A | 10/1992 | Clayman | |
| 5,159,927 A * | 11/1992 | Schmid | 607/53 |
| 5,187,672 A | 2/1993 | Chance et al. | |
| 5,192,278 A | 3/1993 | Hayes et al. | |
| 5,212,386 A | 5/1993 | Gratton et al. | |
| 5,213,093 A | 5/1993 | Swindle | |
| 5,213,105 A | 5/1993 | Gratton et al. | |
| 5,257,202 A | 10/1993 | Feddersen et al. | |
| 5,259,382 A | 11/1993 | Kronberg | |
| 5,261,822 A | 11/1993 | Hall et al. | |
| 5,323,010 A | 6/1994 | Gratton et al. | |
| 5,327,902 A | 7/1994 | Lemmen | |
| 5,353,799 A | 10/1994 | Chance | |
| 5,355,181 A * | 10/1994 | Ashizaki et al. | 348/744 |
| 5,386,827 A | 2/1995 | Chance et al. | |
| 5,391,202 A * | 2/1995 | Lipshitz et al. | 623/6.34 |
| 5,402,778 A | 4/1995 | Chance | |
| 5,419,312 A | 5/1995 | Arenberg et al. | |
| 5,430,175 A | 7/1995 | Hess et al. | |
| 5,445,146 A | 8/1995 | Bellinger | |
| 5,464,960 A | 11/1995 | Hall et al. | |
| 5,467,104 A * | 11/1995 | Furness et al. | 345/8 |
| 5,473,707 A | 12/1995 | Werth | |
| 5,473,708 A | 12/1995 | Werth | |
| 5,480,482 A | 1/1996 | Novinson | |
| 5,484,432 A | 1/1996 | Sand | |
| 5,548,604 A | 8/1996 | Toepel | |
| 5,553,614 A | 9/1996 | Chance | |
| 5,564,417 A | 10/1996 | Chance | |
| 5,596,339 A * | 1/1997 | Furness et al. | 345/8 |
| 5,608,519 A | 3/1997 | Gourley et al. | |
| 5,653,751 A * | 8/1997 | Samiy et al. | 623/6.63 |
| 5,659,327 A * | 8/1997 | Furness et al. | 345/8 |
| 5,664,574 A | 9/1997 | Chance | |
| 5,704,899 A | 1/1998 | Milo | |
| 5,709,645 A * | 1/1998 | Siever | 600/27 |
| 5,733,333 A * | 3/1998 | Sankey | 623/4.1 |
| 5,754,578 A | 5/1998 | Jayaraman | |
| 5,755,752 A | 5/1998 | Segal | |
| 5,791,231 A | 8/1998 | Cohn et al. | |
| 5,792,051 A | 8/1998 | Chance | |
| 5,796,889 A | 8/1998 | Xu et al. | |
| 5,799,030 A | 8/1998 | Brenner | |
| 5,820,625 A | 10/1998 | Izawa et al. | |
| 5,827,265 A | 10/1998 | Glinsky et al. | |
| 5,836,996 A * | 11/1998 | Doorish | 623/6.63 |
| 5,851,223 A | 12/1998 | Liss et al. | |
| 5,861,936 A * | 1/1999 | Sorensen | 351/200 |
| 5,899,865 A | 5/1999 | Chance | |
| 5,913,884 A | 6/1999 | Trauner et al. | |
| 5,935,155 A * | 8/1999 | Humayun et al. | 607/54 |
| 5,957,960 A | 9/1999 | Chen et al. | |
| 5,982,555 A * | 11/1999 | Melville et al. | 359/630 |
| 6,033,431 A | 3/2000 | Segal | |
| 6,048,359 A | 4/2000 | Biel | |
| 6,055,110 A | 4/2000 | Kintz et al. | |
| 6,066,127 A | 5/2000 | Abe | |
| 6,074,411 A | 6/2000 | Lai et al. | |
| 6,104,957 A | 8/2000 | Alo et al. | |
| 6,110,195 A | 8/2000 | Xie et al. | |
| 6,152,882 A | 11/2000 | Prutchi | |
| 6,171,239 B1 | 1/2001 | Humphrey | |
| 6,184,542 B1 | 2/2001 | Alphonse | |
| 6,224,969 B1 | 5/2001 | Steenbergen et al. | |
| 6,240,308 B1 | 5/2001 | Hardy et al. | |
| 6,246,892 B1 | 6/2001 | Chance | |
| 6,254,637 B1 | 7/2001 | Lee et al. | |
| 6,257,759 B1 | 7/2001 | Witonsky et al. | |
| 6,258,082 B1 | 7/2001 | Lin | |
| 6,263,221 B1 | 7/2001 | Chance et al. | |
| 6,267,779 B1 | 7/2001 | Gerdes | |
| 6,272,367 B1 | 8/2001 | Chance | |
| 6,284,078 B1 | 9/2001 | Witonsky et al. | |
| 6,294,109 B1 | 9/2001 | Ratna et al. | |
| 6,301,279 B1 | 10/2001 | Garbuzov et al. | |
| 6,307,526 B1 * | 10/2001 | Mann | 345/8 |
| 6,310,083 B1 | 10/2001 | Kao et al. | |
| 6,312,451 B1 | 11/2001 | Streeter | |
| 6,314,324 B1 | 11/2001 | Lattner et al. | |
| 6,317,103 B1 * | 11/2001 | Furness et al. | 345/8 |
| 6,324,429 B1 | 11/2001 | Shire et al. | |
| 6,330,388 B1 | 12/2001 | Bendett et al. | |
| 6,339,606 B1 | 1/2002 | Alphonse | |
| 6,349,001 B1 * | 2/2002 | Spitzer | 359/618 |
| 6,350,275 B1 * | 2/2002 | Vreman et al. | 607/88 |
| 6,353,226 B1 | 3/2002 | Khalil et al. | |
| 6,358,272 B1 | 3/2002 | Wilden | |
| 6,363,188 B1 | 3/2002 | Alphonse | |
| 6,391,055 B1 | 5/2002 | Ikada et al. | |
| 6,396,461 B1 * | 5/2002 | Lewis et al. | 345/7 |
| 6,400,989 B1 * | 6/2002 | Eckmiller | 607/54 |
| 6,417,524 B1 | 7/2002 | Alphonse | |
| 6,421,474 B2 | 7/2002 | Jewell et al. | |
| 6,444,313 B1 | 9/2002 | Ono et al. | |
| 6,456,866 B1 | 9/2002 | Tyler et al. | |
| 6,458,157 B1 * | 10/2002 | Suaning | 623/6.63 |
| 6,459,715 B1 | 10/2002 | Khalfin et al. | |
| 6,474,816 B2 * | 11/2002 | Butler et al. | 351/221 |
| 6,475,800 B1 | 11/2002 | Hazen et al. | |
| 6,488,704 B1 | 12/2002 | Connelly et al. | |
| 6,493,476 B2 | 12/2002 | Bendett | |
| 6,505,075 B1 | 1/2003 | Weiner | |
| 6,542,530 B1 | 4/2003 | Shieh et al. | |
| 6,542,772 B1 | 4/2003 | Chance | |
| 6,546,291 B2 | 4/2003 | Merfeld et al. | |
| 6,556,611 B1 | 4/2003 | Khalfin et al. | |
| 6,564,076 B1 | 5/2003 | Chance | |
| 6,585,722 B1 | 7/2003 | Abe | |
| 6,592,611 B1 | 7/2003 | Zawada | |
| 6,630,673 B2 | 10/2003 | Khalil et al. | |
| 6,636,678 B1 | 10/2003 | Bendett et al. | |
| 6,639,930 B2 | 10/2003 | Griffel et al. | |
| 6,669,379 B2 | 12/2003 | Janosik et al. | |
| 6,669,765 B2 | 12/2003 | Senga et al. | |
| 6,688,783 B2 | 2/2004 | Janosik et al. | |
| 6,690,873 B2 | 2/2004 | Bendett et al. | |
| 6,735,474 B1 | 5/2004 | Loeb et al. | |
| 6,735,475 B1 | 5/2004 | Whitehurst et al. | |
| 6,736,807 B2 | 5/2004 | Yamazaki et al. | |
| 6,744,548 B2 | 6/2004 | Abeles | |
| 6,746,473 B2 | 6/2004 | Shanks et al. | |
| 6,748,275 B2 | 6/2004 | Lattner et al. | |
| 6,823,109 B2 | 11/2004 | Sasaki et al. | |
| RE38,670 E | 12/2004 | Asah et al. | |
| 6,836,685 B1 | 12/2004 | Fitz | |
| 6,871,084 B1 | 3/2005 | Kingsley et al. | |
| 6,902,528 B1 | 6/2005 | Garibaldi et al. | |
| 6,909,826 B2 | 6/2005 | Cai et al. | |

(56) References Cited

U.S. PATENT DOCUMENTS

| | | |
|---|---|---|
| 6,920,358 B2 * | 7/2005 | Greenberg et al. ............. 607/54 |
| 6,921,413 B2 | 7/2005 | Mahadevan-Jansen et al. |
| 6,953,341 B2 | 10/2005 | Black |
| 6,956,650 B2 | 10/2005 | Boas et al. |
| 6,976,997 B2 | 12/2005 | Noolandi et al. |
| 6,980,579 B2 | 12/2005 | Jewell |
| 6,989,023 B2 | 1/2006 | Black |
| 7,003,353 B1 | 2/2006 | Parkhouse |
| 7,004,645 B2 | 2/2006 | Lemoff et al. |
| 7,006,749 B2 | 2/2006 | Illich et al. |
| 7,010,341 B2 | 3/2006 | Chance |
| 7,010,356 B2 | 3/2006 | Jog et al. |
| 7,031,363 B2 | 4/2006 | Biard et al. |
| 7,040,805 B1 | 5/2006 | Ou et al. |
| 7,068,878 B2 | 6/2006 | Crossman-Bosworth et al. |
| 7,069,083 B2 | 6/2006 | Finch |
| 7,079,900 B2 | 7/2006 | Greenburg et al. |
| 7,085,300 B2 | 8/2006 | Werner et al. |
| 7,095,770 B2 | 8/2006 | Johnson |
| 7,103,416 B2 * | 9/2006 | Ok et al. ......................... 607/54 |
| 7,116,886 B2 | 10/2006 | Colgan et al. |
| 7,130,447 B2 * | 10/2006 | Aughey et al. ............... 382/103 |
| 7,131,968 B2 | 11/2006 | Bendett et al. |
| 7,133,022 B2 * | 11/2006 | Grabert ......................... 345/156 |
| 7,139,603 B2 | 11/2006 | Chance |
| 7,156,866 B1 | 1/2007 | Riggs et al. |
| 7,160,289 B2 | 1/2007 | Cohen |
| 7,177,081 B2 | 2/2007 | Tomita et al. |
| 7,190,993 B2 | 3/2007 | Sharma et al. |
| 7,194,063 B2 | 3/2007 | Dilmanian et al. |
| 7,206,022 B2 * | 4/2007 | Miller et al. ............. 348/333.03 |
| 7,225,028 B2 | 5/2007 | Della Santina et al. |
| 7,231,256 B2 | 6/2007 | Wahlstrand et al. |
| 7,244,253 B2 | 7/2007 | Neev |
| 7,302,296 B1 | 11/2007 | Hoffer |
| 7,309,335 B2 | 12/2007 | Altshuler et al. |
| 7,311,722 B2 | 12/2007 | Larsen |
| 7,311,723 B2 * | 12/2007 | Seibel et al. ..................... 607/89 |
| 7,324,852 B2 | 1/2008 | Barolat et al. |
| 7,329,251 B2 | 2/2008 | Yamada et al. |
| 7,337,004 B2 | 2/2008 | Classen et al. |
| 7,351,241 B2 | 4/2008 | Bendett et al. |
| 7,391,561 B2 | 6/2008 | Di Teodoro et al. |
| 7,402,167 B2 | 7/2008 | Nemenov |
| RE40,587 E | 11/2008 | McKinnon |
| 7,488,341 B2 | 2/2009 | Merfeld |
| 7,598,088 B2 | 10/2009 | Balas |
| 7,647,112 B2 | 1/2010 | Tracey et al. |
| 7,654,750 B2 | 2/2010 | Brenner et al. |
| 7,657,062 B2 * | 2/2010 | Pilu ................................ 382/103 |
| 7,736,382 B2 * | 6/2010 | Webb et al. ....................... 607/89 |
| 7,747,318 B2 | 6/2010 | John et al. |
| 7,756,588 B2 | 7/2010 | Jog et al. |
| 7,771,374 B2 | 8/2010 | Slatkine |
| 7,776,631 B2 | 8/2010 | Miles |
| 7,787,170 B2 | 8/2010 | Patel et al. |
| 7,792,588 B2 | 9/2010 | Harding |
| 7,797,029 B2 | 9/2010 | Gibson et al. |
| 7,801,601 B2 | 9/2010 | Maschino et al. |
| 7,803,454 B2 | 9/2010 | Toepel |
| 7,833,257 B2 | 11/2010 | Walsh, Jr. et al. |
| 7,857,849 B2 | 12/2010 | Myung et al. |
| 7,865,236 B2 | 1/2011 | Cory et al. |
| 7,873,085 B2 | 1/2011 | Babushkin et al. |
| 7,883,535 B2 * | 2/2011 | Cantin et al. ..................... 607/89 |
| 7,883,536 B1 | 2/2011 | Bendett et al. |
| 7,894,905 B2 | 2/2011 | Pless et al. |
| 7,894,909 B2 * | 2/2011 | Greenberg et al. ............. 607/54 |
| 7,899,512 B2 | 3/2011 | Labadie et al. |
| 7,904,139 B2 | 3/2011 | Chance |
| 7,908,010 B2 * | 3/2011 | Greenberg et al. ............. 607/54 |
| 7,909,867 B2 | 3/2011 | Myung et al. |
| 7,914,842 B1 | 3/2011 | Greenberg et al. |
| 7,951,181 B2 | 5/2011 | Mahadevan-Jansen et al. |
| 7,962,192 B2 | 6/2011 | Bodduluri et al. |
| 7,988,688 B2 | 8/2011 | Webb et al. |
| 8,012,189 B1 | 9/2011 | Webb et al. |
| 8,078,263 B2 | 12/2011 | Zeman et al. |
| 8,136,531 B2 | 3/2012 | Chariff |
| 8,150,526 B2 * | 4/2012 | Gross et al. ...................... 607/54 |
| 8,197,539 B2 | 6/2012 | Nasiatka et al. |
| 8,207,211 B2 | 6/2012 | Wharton et al. |
| 8,244,363 B2 * | 8/2012 | Greenberg et al. ............. 607/54 |
| 8,244,364 B2 * | 8/2012 | Horsager et al. ................ 607/54 |
| 8,260,428 B2 * | 9/2012 | Fink et al. ......................... 607/54 |
| 8,271,091 B2 * | 9/2012 | McMahon et al. ............... 607/53 |
| 8,311,635 B2 * | 11/2012 | Greenberg et al. ............. 607/54 |
| 8,396,570 B2 | 3/2013 | Dadd et al. |
| 8,475,506 B1 * | 7/2013 | Bendett et al. ................... 607/89 |
| 8,652,187 B2 * | 2/2014 | Wells et al. ........................ 607/89 |
| 8,709,078 B1 * | 4/2014 | Friend et al. ................... 623/5.11 |
| 8,792,978 B2 * | 7/2014 | Wells et al. ......................... 607/3 |
| 2002/0002391 A1 | 1/2002 | Gerdes |
| 2002/0101568 A1 * | 8/2002 | Eberl et al. ....................... 351/211 |
| 2003/0158588 A1 * | 8/2003 | Rizzo et al. ....................... 607/54 |
| 2003/0236458 A1 | 12/2003 | Hochman |
| 2004/0143190 A1 | 7/2004 | Schnitzer |
| 2004/0225339 A1 | 11/2004 | Yaroslavsky et al. |
| 2004/0236421 A1 * | 11/2004 | Lipshitz et al. ................ 623/6.27 |
| 2005/0090875 A1 * | 4/2005 | Palanker et al. ................. 607/54 |
| 2005/0099824 A1 | 5/2005 | Dowling et al. |
| 2005/0143789 A1 | 6/2005 | Whitehurst et al. |
| 2005/0195277 A1 * | 9/2005 | Yamasaki ......................... 348/61 |
| 2006/0142818 A1 * | 6/2006 | Chow et al. ....................... 607/53 |
| 2006/0161218 A1 | 7/2006 | Danilov |
| 2006/0167564 A1 | 7/2006 | Flaherty et al. |
| 2006/0276861 A1 | 12/2006 | Lin |
| 2007/0053996 A1 | 3/2007 | Boyden et al. |
| 2007/0054319 A1 | 3/2007 | Boyden et al. |
| 2007/0191906 A1 | 8/2007 | Iyer et al. |
| 2007/0191910 A1 * | 8/2007 | Ren ...................................... 607/54 |
| 2007/0261127 A1 | 11/2007 | Boyden et al. |
| 2008/0009748 A1 | 1/2008 | Gratton et al. |
| 2008/0077200 A1 | 3/2008 | Bendett et al. |
| 2008/0161697 A1 | 7/2008 | Chance |
| 2008/0221640 A1 | 9/2008 | Overstreet et al. |
| 2008/0228242 A1 * | 9/2008 | Fink et al. ......................... 607/54 |
| 2008/0299201 A1 | 12/2008 | Kozloski et al. |
| 2008/0306576 A1 | 12/2008 | Boyden et al. |
| 2009/0030327 A1 | 1/2009 | Chance |
| 2009/0054954 A1 | 2/2009 | Foley et al. |
| 2009/0062685 A1 | 3/2009 | Bergethon et al. |
| 2009/0163982 A1 | 6/2009 | deCharms |
| 2009/0177247 A1 | 7/2009 | Neal et al. |
| 2009/0177255 A1 | 7/2009 | Merfeld |
| 2009/0210039 A1 | 8/2009 | Boyden et al. |
| 2010/0016732 A1 | 1/2010 | Wells et al. |
| 2010/0049180 A1 | 2/2010 | Wells et al. |
| 2010/0057166 A1 * | 3/2010 | Ahuja et al. ....................... 607/53 |
| 2010/0114190 A1 * | 5/2010 | Bendett et al. ................... 607/3 |
| 2010/0145418 A1 | 6/2010 | Zhang et al. |
| 2010/0162109 A1 | 6/2010 | Chatterjee et al. |
| 2010/0174329 A1 | 7/2010 | Dadd et al. |
| 2010/0174330 A1 | 7/2010 | Dadd et al. |
| 2010/0174344 A1 | 7/2010 | Dadd et al. |
| 2010/0184818 A1 | 7/2010 | Wharton et al. |
| 2010/0191079 A1 | 7/2010 | Shoureshi et al. |
| 2010/0191308 A1 | 7/2010 | Meister |
| 2010/0197995 A1 | 8/2010 | Wenzel et al. |
| 2010/0198317 A1 | 8/2010 | Lenarz et al. |
| 2010/0220176 A1 * | 9/2010 | Ziemeck et al. ................ 348/50 |
| 2010/0220291 A1 * | 9/2010 | Horning et al. ................ 351/210 |
| 2010/0262212 A1 | 10/2010 | Shoham et al. |
| 2010/0292758 A1 | 11/2010 | Lee et al. |
| 2011/0004271 A1 * | 1/2011 | Dapper et al. ................... 607/53 |
| 2011/0004272 A1 * | 1/2011 | Seibel et al. ..................... 607/54 |
| 2011/0060410 A1 * | 3/2011 | Tiedtke et al. ................ 623/6.63 |
| 2011/0172680 A1 | 7/2011 | Young et al. |
| 2011/0172725 A1 | 7/2011 | Wells et al. |
| 2011/0295331 A1 | 12/2011 | Wells et al. |
| 2011/0295344 A1 | 12/2011 | Wells et al. |
| 2011/0295345 A1 | 12/2011 | Wells et al. |
| 2011/0295347 A1 * | 12/2011 | Wells et al. ....................... 607/89 |
| 2012/0016174 A1 * | 1/2012 | De Taboada et al. ............. 600/2 |

(56) References Cited

U.S. PATENT DOCUMENTS

| | | | | |
|---|---|---|---|---|
| 2012/0283804 | A1* | 11/2012 | Kang et al. | 607/89 |
| 2013/0131797 | A1* | 5/2013 | Klaver et al. | 623/6.63 |
| 2014/0236270 | A1* | 8/2014 | Friend et al. | 607/92 |

FOREIGN PATENT DOCUMENTS

| | | |
|---|---|---|
| WO | WO 2010011404 A2 | 1/2010 |
| WO | WO 2011120540 | 10/2011 |

OTHER PUBLICATIONS

Hibbs-Brenner, VCSEL technology for medical diagnostics and therapeutics, Proc. of SPIE, 7180, 2009.*

The Hutchinson Encyclopedia, infrared radiation, 2013.*

W.L.Gore and Associates Inc. v. Garlock Inc., 721 F.2d 1540, 220 U.S.P.Q. 303, Federal Circuit, 1983.*

Allegre, et al., "Stimulation in the rat of a nerve fiber bundle by a short UV pulse from an excimer laser", "NeuroScience Letters", 1994, pp. 261-264, vol. 180.

Arridge, et al., "The theoretical basis for the determination of optical pathlengths in tissue: temporal and frequency analysis", "Phys. Med. Biol.", 1992, pp. 1531-1560, vol. 37.

Augustine, George J., "Combining patch-clamp and optical methods in brain slices", "Journal of Neuroscience Methods", 1994, pp. 163-169, vol. 54.

Banghart, Matthew, et al., "Light-activated ion channels for remote control of neuronal firing", "Nature Neuroscience", Nov. 21, 2004, pp. 1381-1386, vol. 7, No. 12.

Bashkato, A., et al., "Optical Clearing of Human Eye Sclera", "Proc. of SPIE", 2009, pp. 71631R-1-71631R-8, vol. 7163.

Bernstein, Jacob G., et al., "Prosthetic systems for therapeutic optical activation and silencing of genetically-targeted neurons", "Proc Soc Photo Opt Instrum Eng.", May 5, 2008, vol. 6854: 68540H.

Boyden, Edward S., et al., "Millisecond-timescale, genetically targeted optical control of neural activity", "Nature Neuroscience", Sep. 2005, pp. 1263-1268, vol. 8, No. 9.

Bureau, Ingrid, et al., "Precise Development of Functional and Anatomical Columns in the Neocortex", "Neuron", Jun. 10, 2004, pp. 789-801, vol. 42.

Chambers, James J., et al., "Light-Induced Depolarization of Neurons Using a Modified Shaker K+ Channel and a Molecular Photoswitch", "Journal of Neurophysiology", Jul. 26, 2006, pp. 2792-2796, vol. 96.

Chance, et al., "Comparison of time-resolved and -unresolved measurements of deoxyhemoglobin in brain", "Proc. Nati. Acad. Sci. USA", Jul. 1988, pp. 4971-4975, vol. 85.

Deal, Walter J., et al., "Photoregulation of Biol. Activity by Photochromic Reagents, 3. Photoreg. of Bioelectricity by Acetylcholine Receptor INH", "Proc. Natl. Acad. Sci.", 1969, pp. 1230-1234, vol. 64, No. 4.

Desmurget, et al., "Movement Intention after Parietal Cortex Stimulation in Humans", "Science", May 8, 2009, pp. 811-813, vol. 324.

Dodt, H.-U., et al., "Circuitry of rat barrel cortex investigated by infrared-guided laser stimulation", "NeuroReport", Mar. 24, 2003, pp. 623-627, vol. 14, No. 4.

Dodt, H.-U., et al., "Precisely Localized LTD in the Neocortex Revealed by Infrared-Guided Laser Stimulation.", "Science", Oct. 1, 1999, pp. 110-113, vol. 286.

Eder, Matthias, et al. , "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.

Fork, Richard L., "Laser Stimulation of Nerve Cells in Aplysia", "Science, New Series", Mar. 5, 1971, pp. 907-908, vol. 171, No. 3974.

Han, Xue, et al., "Multiple-Color Optical Activation, Silencing, and Desynchronization of Neural Activity, with Single-Spike Temporal Resol", "PLoS ONE 2(3): e299. doi:10.1371/journal.pone. 0000299", Mar. 2007, pp. e299, No. 3, Publisher: www.plosone.org.

Harner, et al., "Improved Preservation of Facial Nerve Function With Use of Electrical Monitoring During Removal of Acoustic Neuromas", "Mayo Clinic Proceedings. Mayo Clinic", Feb. 1987, pp. 92-102, vol. 62.

Huang, Ying-Ying, et al., "Biphasic Dose Response in Low Level Light Therapy", "Dose-Response", 2009, pp. 358-383, vol. 7.

Izzo, et al., "Laser Stimulation of the Auditory Nerve", "Lasers in Surgery and Medicine", 2006, Publisher: Wiley-Liss, Inc.

Izzo, et al., "Selectivity of neural stimulation in the auditory system: a comparison of optic and electric stimuli", "Journal of Biomedical Optics", Mar./Apr. 2007, p. 021008 , vol. 12, No. 2.

Izzo, Agnella D., et al., "Optical Parameter Variability in Laser Nerve Stimulation: A Study of Pulse Duration, Repetition Rate, and Wavelength.", "IEEE Transactions on Biomedical Engineering", Jun. 2007, pp. 1108-1114, vol. 54, No. 6(1).

Maiorov, M., et al., "218 W quasi-CW operation of 1.83 um two-dimensional laser diode array", "Electronics Letters", Apr. 15, 1999, pp. 636-638, vol. 35, No. 8.

Makeieff, et al., "Continuous Facial Nerve Monitoring During Pleomorphic Adenoma Recurrence Surgery", "The Laryngoscope", Jul. 2005, pp. 1310-1314.

Matthies, et al., "Direct Brainstem Recording of Auditory Evoked Potentials During Vestibular Schwannoma Resection: Nuclear BAEP Recording", "J. Neurosurg.", Jun. 1997, pp. 1057-1062, vol. 86.

Meier, et al., "Continuous Intraoperative Facial Nerve Monitoring in Predicting Postoperative Injury During Parotidectomy", "The Laryngoscope", Sep. 2006, pp. 1569-1572, vol. 116.

Moller, et al., "Intraoperative Neurophysiologic Monitoring", "American Journal of Otology", Jan. 1995, pp. 115-117, vol. 16, No. 1.

Nakagawa, Atsuhiro, et al., "Pulsed holmium:yttrium-aluminum-garnet laser-induced liquid jet as a novel dissection device in neuroendoscopic surgery", "J. Neurosurg.", Jul. 2004 , pp. 145-150, vol. 101.

Naples, et al., "A spiral nerve cuff electrode for peripheral nerve stimulation", "IEEE Trans Biomed Eng", Nov. 1988, pp. 905-916, vol. 35, No. 11.

Passos, D., et al., "Tissue phantom for optical diagnostics based on a suspension of microspheres with a fractal size distribution", "Journal of Biomedical Optics.", Nov.-Dec. 2005 , p. 064036, vol. 10, No. 6.

Princeton Lightwave (Company), "High Power Multimode Laser Arrays", "www.princetonlightwave.com/content/pli_high_power_multimode_laser_arrays.pdf", Dec. 24, 2005 downloaded.

Princeton Lightwave (Company), "High Power Water Cooled Laser Stack", "http://www.princetonlightwave.com/content/pli_high_power_multimode_laser_stacks.pdf", Oct. 24, 2005 downloaded.

Princeton Lightwave (Company), "High Power Single Element Laser", "www.princetonlightwave.com/content/HP%20Single%20Element%20Laser%20version%202.pdf", 2005 (downloaded).

Rolfe, "In Vivo Near-Infrared Spectroscopy", "Annu. Rev. Biomed. Eng.", 2000, pp. 715-754 , vol. 2.

Schiefer, et al., "A Model of Selective Activation of the Femoral Nerve with a Flat Interface Nerve Electrode for a Lower Extremity Neuropr", "IEEE Trans Neural Syst Rehabil Eng", Apr. 2008, pp. 195-204, vol. 16, No. 2.

Schwartz, et al., "Auditory Brainstem Implants", "Neurotherapeutics: The Journal of the American Society for Experimental NeuroTherapeutics", Jan. 2008, pp. 128-136, vol. 5.

Tarler, et al., "Comparison of joint torque evoked with monopolar and tripolar-cuff electrodes", "IEEE Trans Neural Syst Rehabil Eng", 2003, pp. 227-235, vol. 11, No. 3.

Teudt, et al., "Optical Stimulation of the Facial Nerve: A New Monitoring Technique?", "The Laryngoscope", 2007, pp. 1641-1647, vol. 117, No. 9.

Tonn, et al., "Acoustic Neuroma Surgery as an Interdisciplinary Approach: A Neurosurgical Series of 508 Patients", "Journal of Neurology, Neurosurgery and Psychiatry", Aug. 2000, pp. 161-166, vol. 69, No. 2.

Vogel, Alfred, et al., "Mechanisms of pulsed laser ablation of biological tissues.", "Chemical Reviews", 2003, pp. 577-644, vol. 103, No. 2.

(56) References Cited

OTHER PUBLICATIONS

Wells, Jonathon, et al., "Application of Infrared Light for in vivo Neural Stimulation.", "Journal of Biomedical Optics", Nov. 2005, pp. 064003-1 to 064003-12, vol. 10, No. 6.

Wells, Jonathon, et al., "Optical stimulation of neural tissue in vivo", "Optics Letters", Mar. 1, 2005, pp. 504-506, vol. 30, No. 5.

Wells, Jonathon D., et al., "Optically Mediated Nerve Stimulation: Identification of Injury Thresholds.", "Lasers in Surgery and Medicine", Jul. 23, 2007, pp. 513-526, vol. 39.

Wells, Jonathon, et al., "Pulsed laser versus electrical energy for peripheral nerve stimulation", "Journal of Neuroscience Methods", 2007, pp. 326-337, vol. 163.

Witt, Robert L., "Facial Nerve Monitoring in Parotid Surgery: The Standard of Care?", "Otolaryngology—Head and Neck Surgery", Nov. 1998, pp. 468-470, vol. 119, No. 5.

Yoo, et al., "Selective recording of the canine hypoglossal nerve using a multicontact flat interface nerve electrode", "IEEE Trans Biomed Eng", Aug. 2005, pp. 1461-1469, vol. 52, No. 8.

Zemelman, Boris V., et al., "Photochemical gating of heterologous ion channels: Remote control over genetically designated populations of neurons", "Proceedings of the National Academy of Sciences", Feb. 4, 2003, pp. 1352-1357, vol. 100, No. 3.

Zhang, Feng, et al., "Channelrhodopsin-2 and optical control of excitable cells", "Nature Methods", Sep. 21, 2006, pp. 785-792, vol. 3, No. 10.

\* cited by examiner

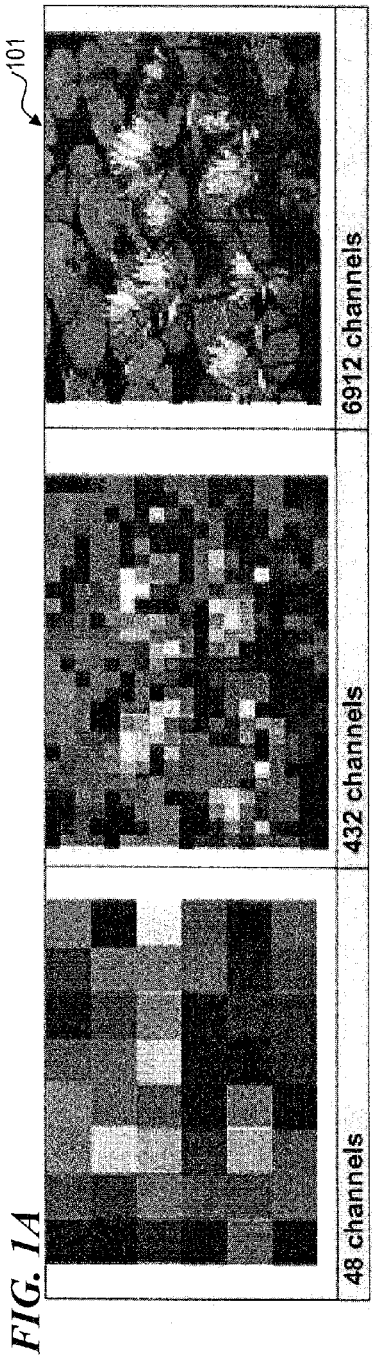
*FIG. 1A*
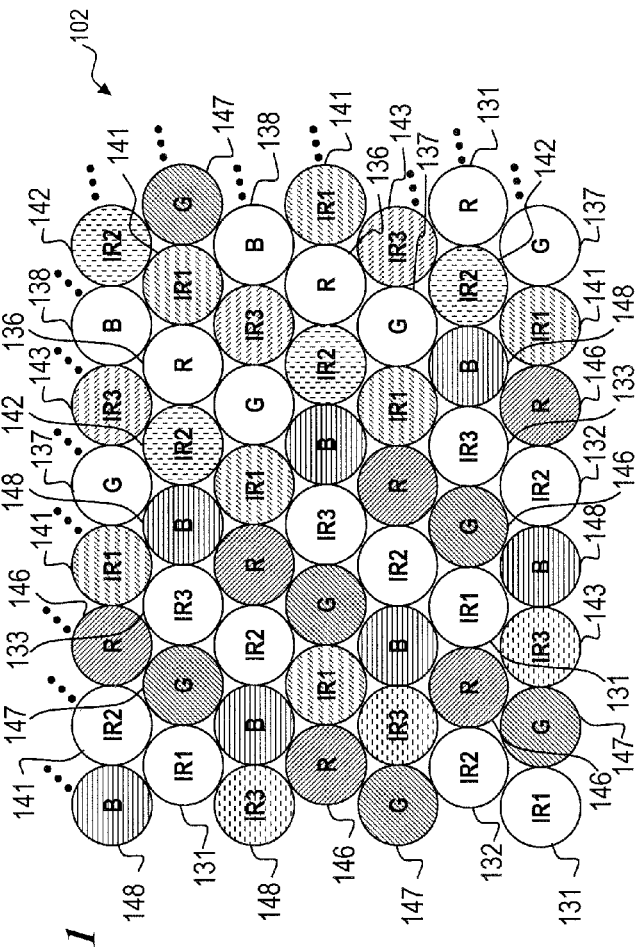
*FIG. 1B1*

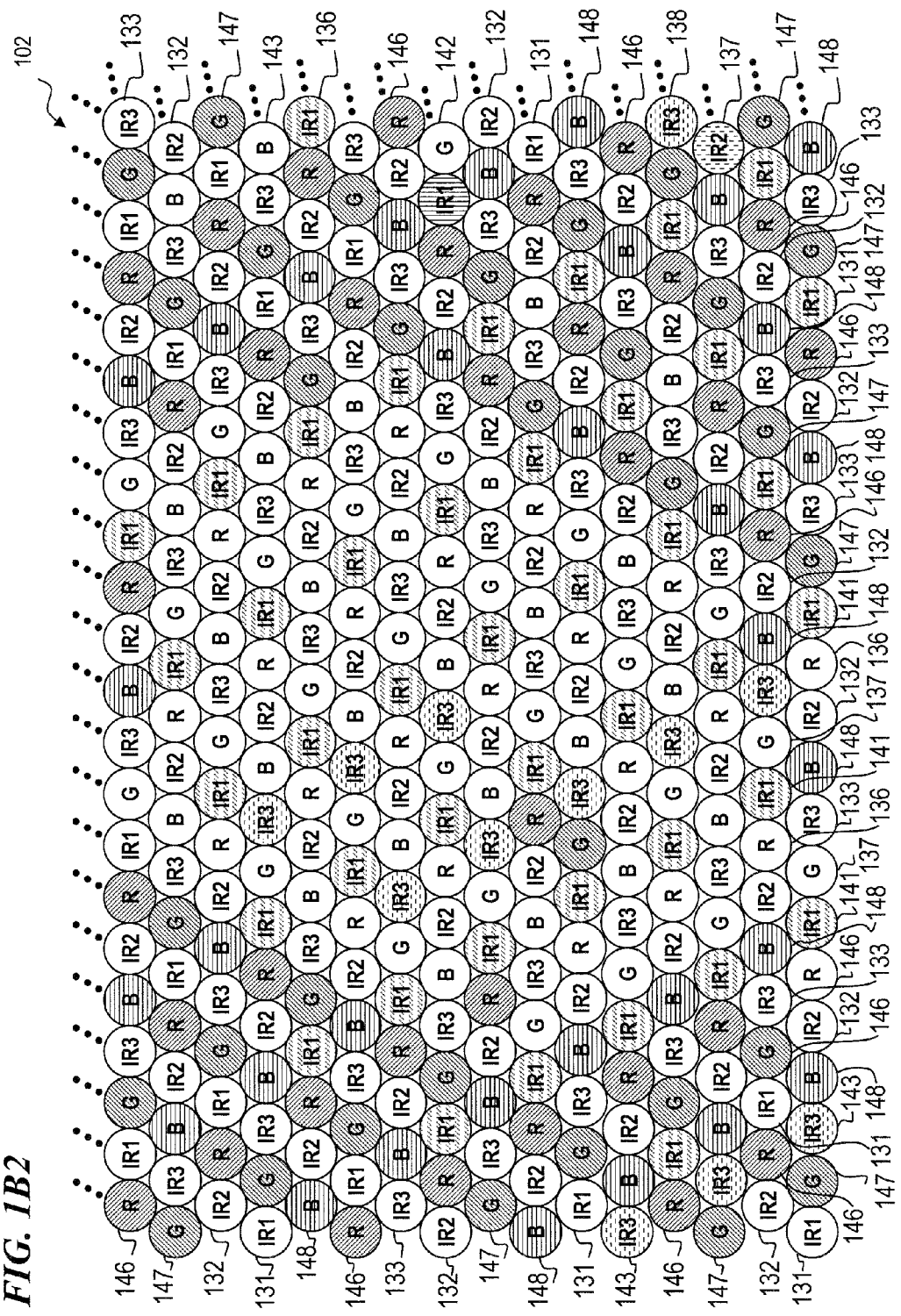
FIG. 1B2

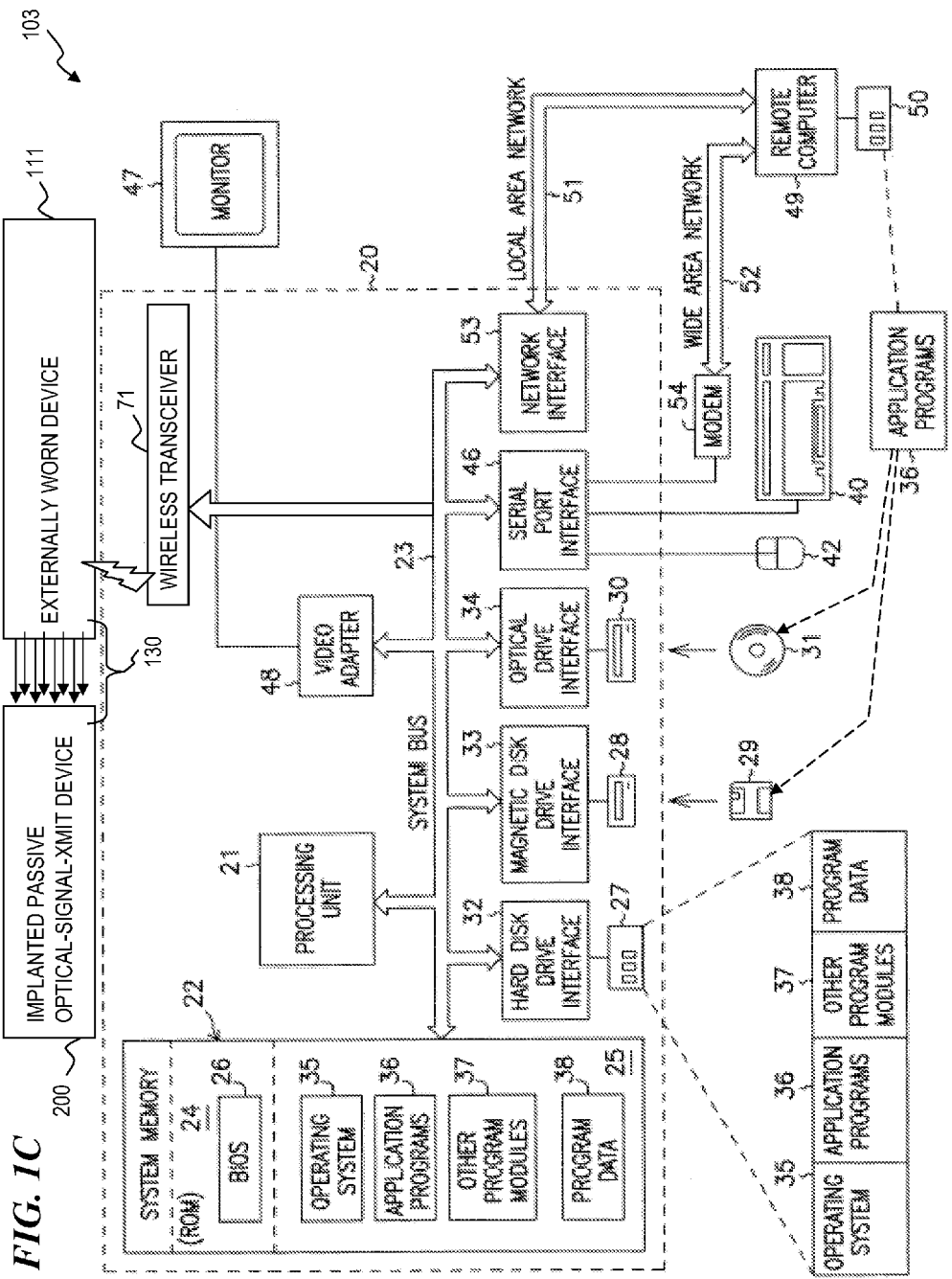

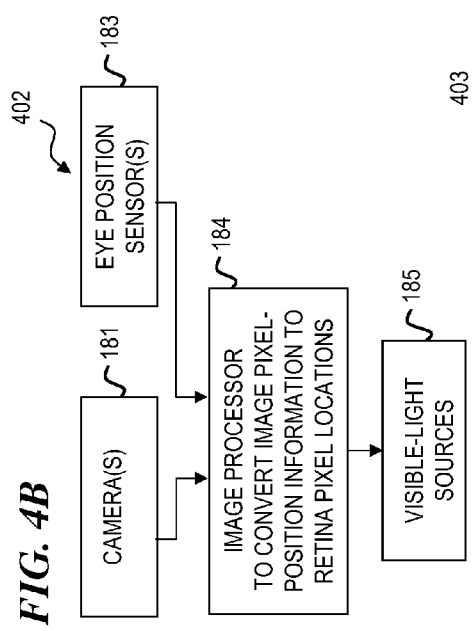
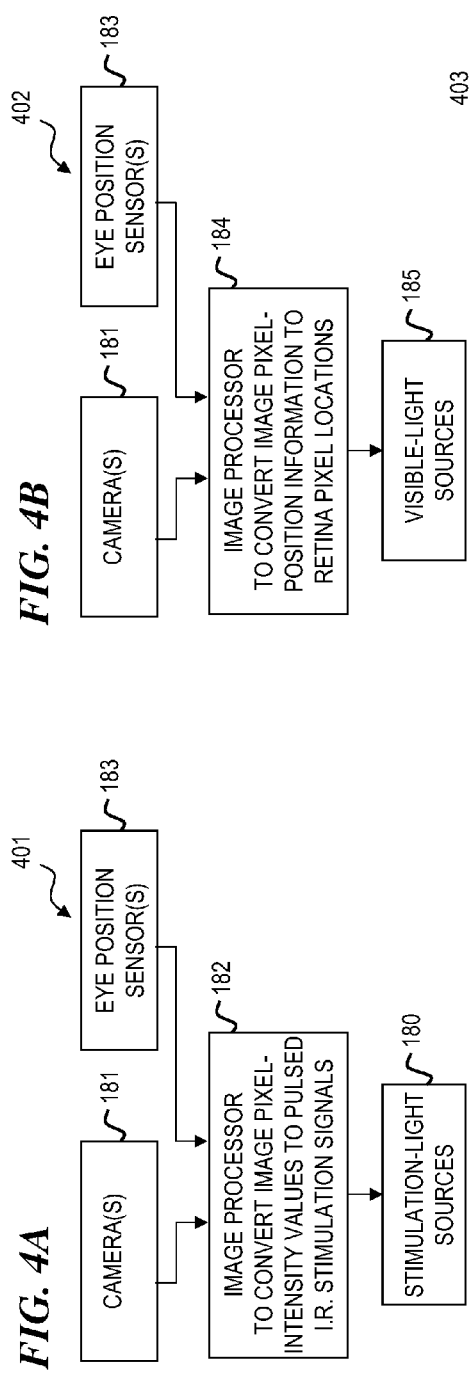
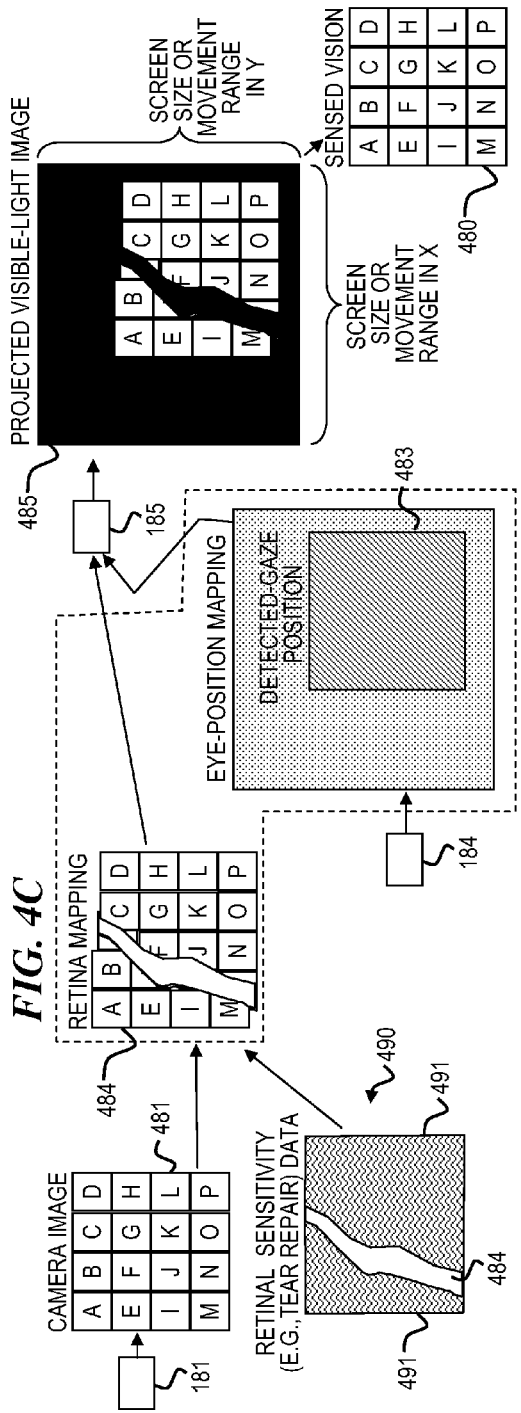

(Simplified Image Processing Diagram)

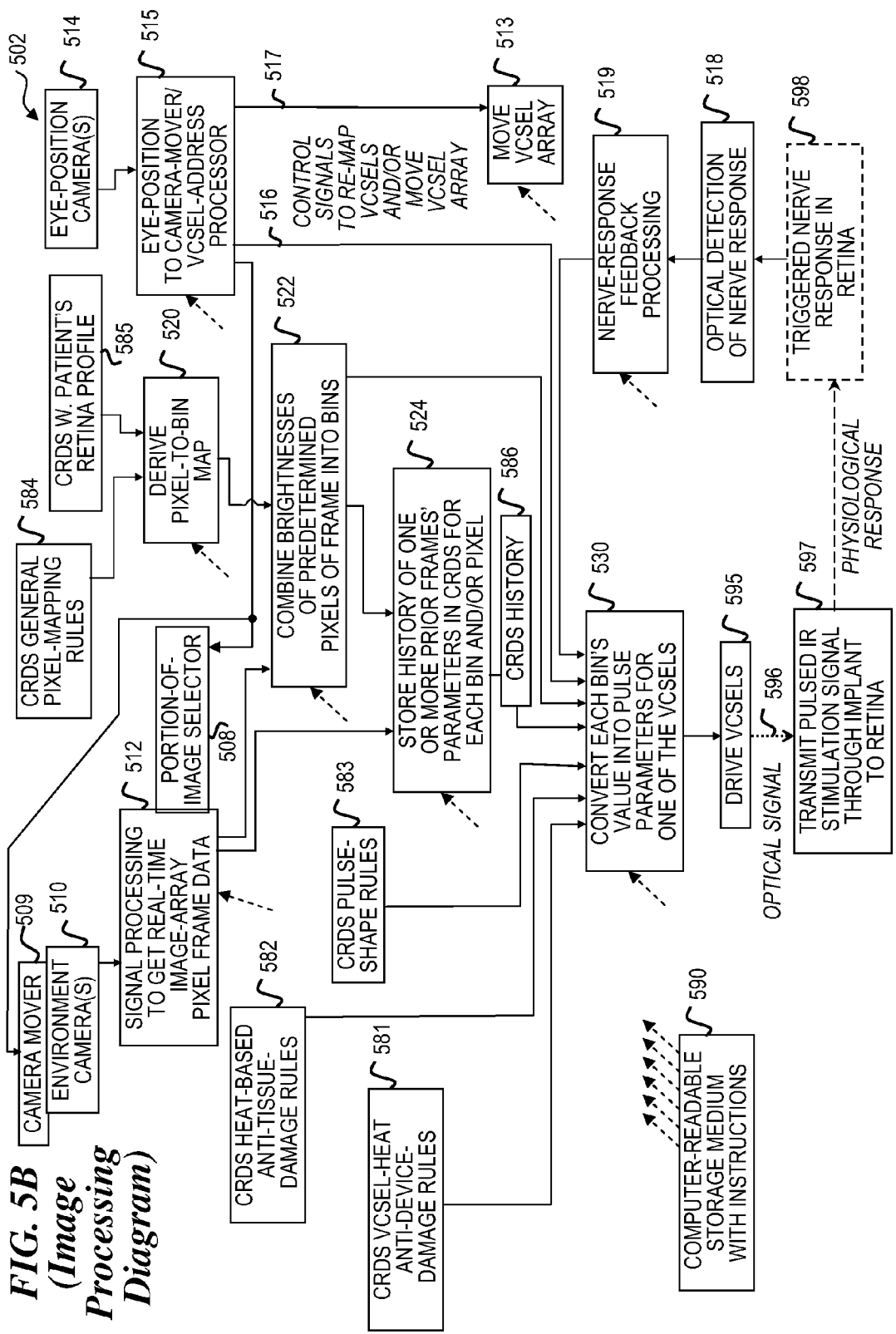
FIG. 5B (Image Processing Diagram)

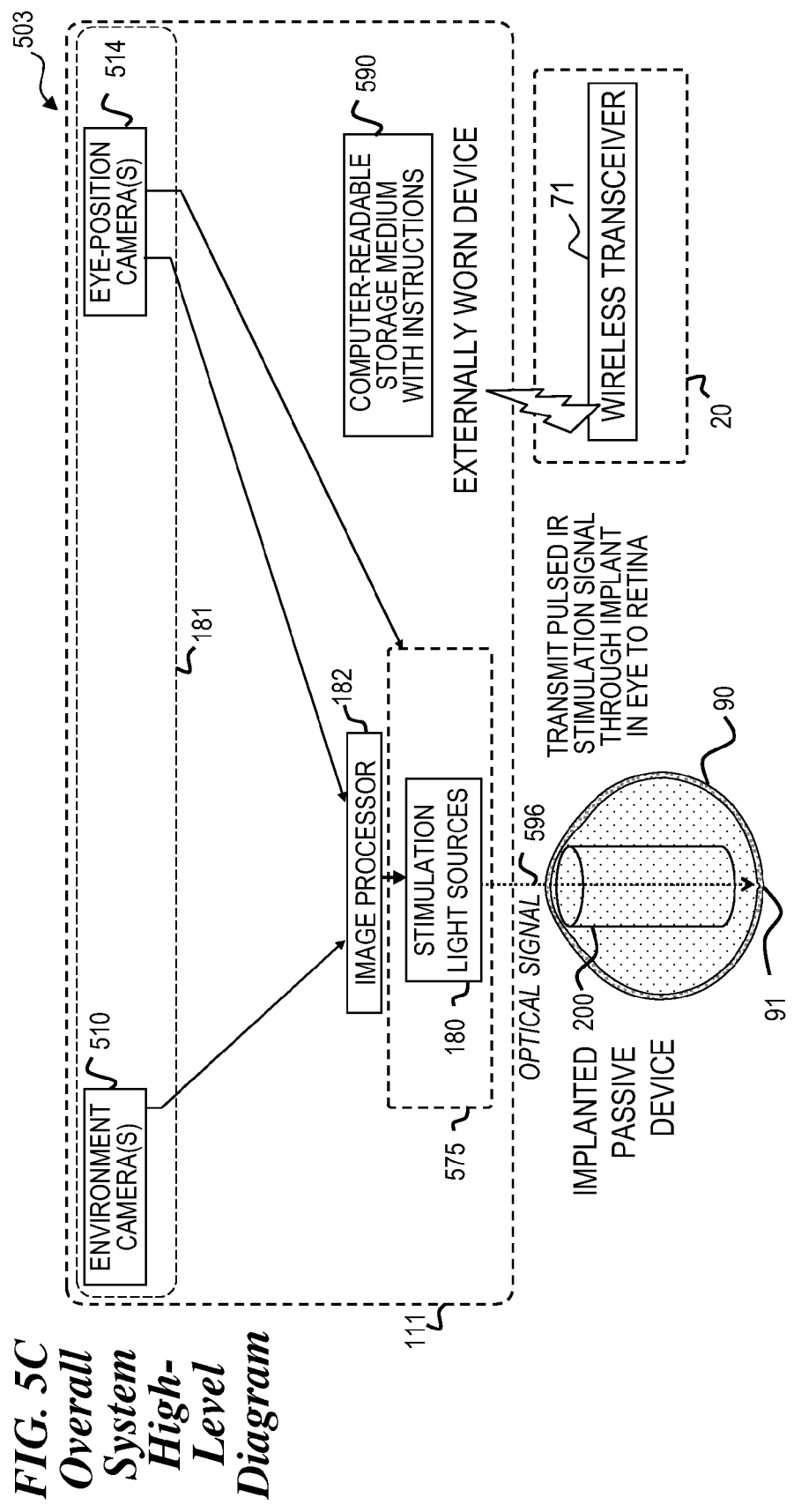
FIG. 5C Overall System High-Level Diagram

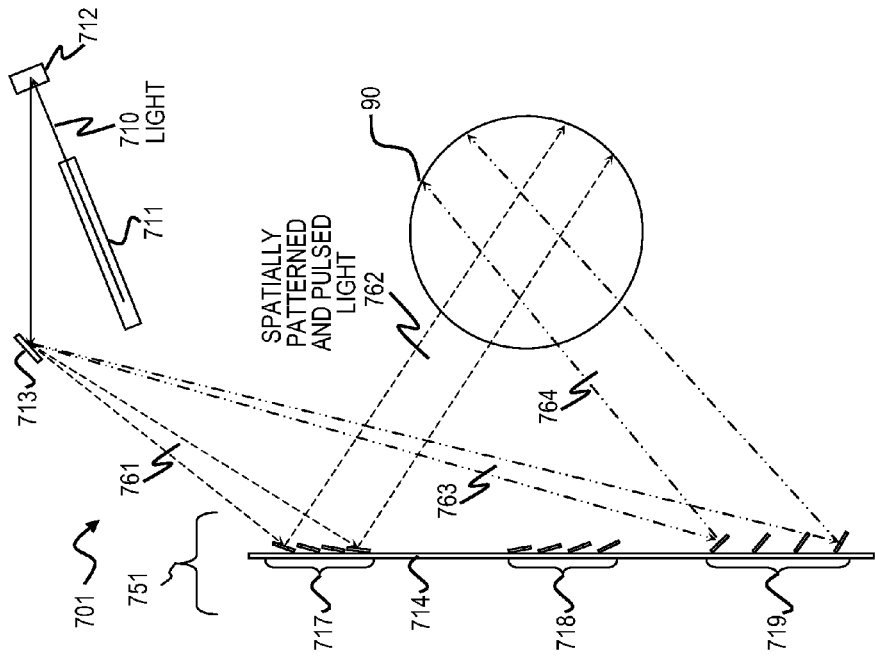
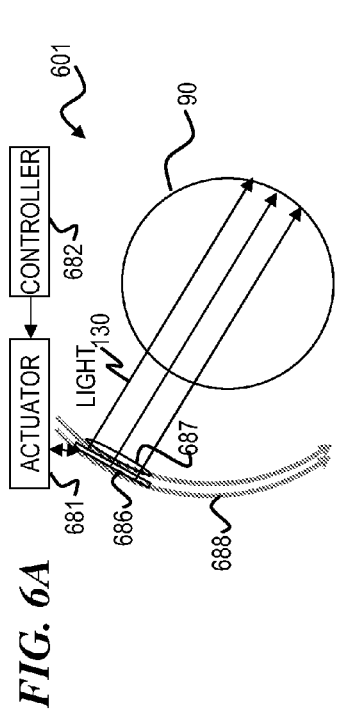
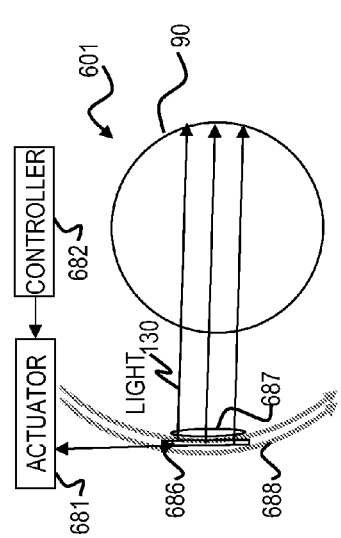
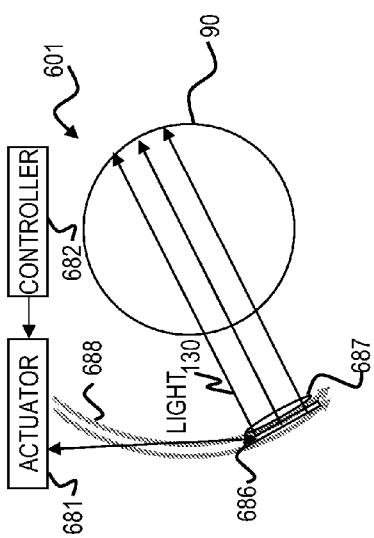

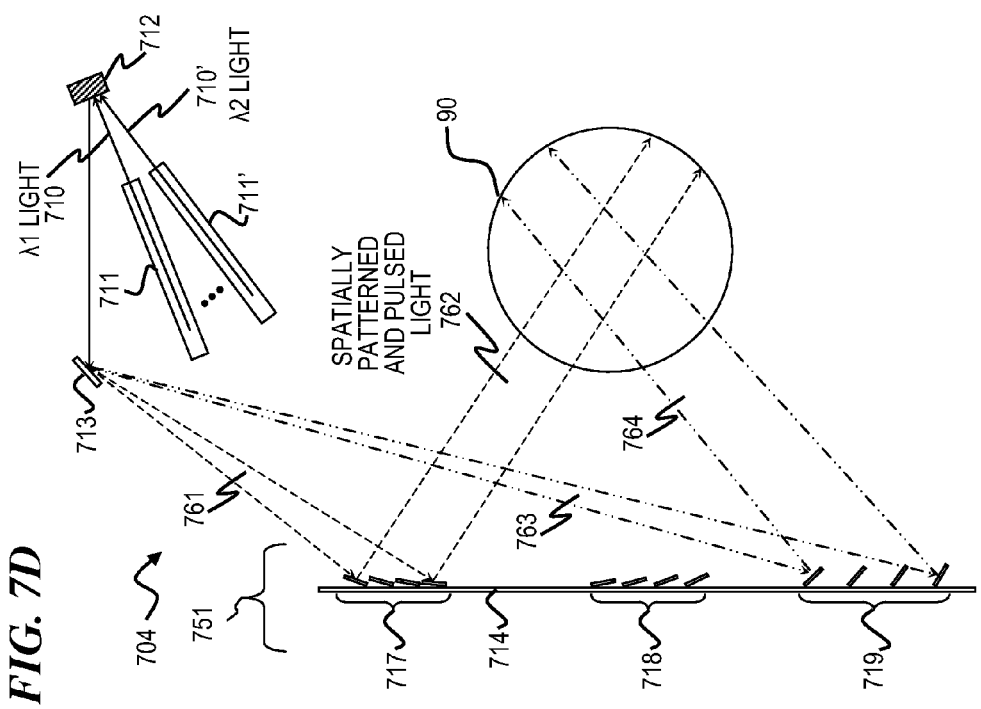

EYE-TRACKING VISUAL PROSTHETIC AND METHOD

CROSS-REFERENCE TO RELATED APPLICATIONS

This application claims priority benefit under 35 U.S.C. §119(e) of U.S. Provisional Patent Application No. 61/514,894 filed Aug. 3, 2011 by Michael E. Friend et al., titled "SIGHT-RESTORING VISUAL PROSTHETIC AND METHOD USING INFRARED NERVE-STIMULATION LIGHT", which is incorporated herein by reference in its entirety.

This invention is related to the following prior applications and patents:

U.S. patent application Ser. No. 13/525,268 filed on even date herewith (Jun. 15, 2012), titled "SIGHT-RESTORING VISUAL PROSTHETIC AND METHOD USING INFRARED NERVE-STIMULATION LIGHT";

U.S. Provisional Patent Application No. 60/715,884 filed Sep. 9, 2005, titled "Apparatus and Method for Optical Stimulation of Nerves";

U.S. patent application Ser. No. 11/257,793 filed Oct. 24, 2005, titled "Apparatus for Optical Stimulation of Nerves and Other Animal Tissue" (now U.S. Pat. No. 7,736,382 issued Jun. 15, 2010);

U.S. Provisional Patent Application No. 60/826,538 filed Sep. 21, 2006, titled "Miniature Apparatus and Method for Optical Stimulation of Nerves and Other Animal Tissue";

U.S. patent application Ser. No. 11/536,639 filed Sep. 28, 2006, titled "Miniature Apparatus and Method for Optical Stimulation of Nerves and Other Animal Tissue" (now U.S. Pat. No. 7,988,688 issued Aug. 2, 2011);

U.S. patent application Ser. No. 11/536,642 filed Sep. 28, 2006, titled "Apparatus and Method for Stimulation of Nerves and Automated Control of Surgical Instruments";

U.S. Provisional Patent Application No. 60/884,619 filed Jan. 11, 2007, titled "Vestibular Implant Using Infrared Nerve Stimulation";

U.S. patent application Ser. No. 11/971,874 filed Jan. 9, 2008, titled "Method and Vestibular Implant using Optical Stimulation of Nerves" (now U.S. Pat. No. 8,012,189 issued Sep. 6, 2011);

U.S. Provisional Patent Application No. 60/964,634 filed Aug. 13, 2007, titled "VCSEL Array Stimulator Apparatus and Method for Light Stimulation of Bodily Tissues";

U.S. patent application Ser. No. 12/191,301 filed Aug. 13, 2008, titled "VCSEL Array Stimulator Apparatus and Method for Light Stimulation of Bodily Tissues" (now U.S. Pat. No. 8,475,506 issued Jul. 2, 2013);

U.S. Provisional Patent Application No. 61/015,665 filed Dec. 20, 2007, titled "Laser Stimulation of the Auditory System at 1.94 μm and Microsecond Pulse Durations";

U.S. Provisional Patent Application No. 61/147,073 filed Jan. 23, 2009, titled "Optical Stimulation Using Infrared Lasers (or In Combination with Electrical Stimulation) of the Auditory Brainstem and/or Midbrain";

U.S. Provisional Patent Application 61/081,732 filed on Jul. 17, 2008, titled "Method and Apparatus for Neural Signal Capture to Drive Neuroprostheses or Bodily Function,"

U.S. Provisional Patent Application 61/226,661 filed on Jul. 17, 2009, titled "Method and Apparatus for Neural-Signal Capture to Drive Neuroprostheses or Control Bodily Function,"

U.S. Patent Publication No. 2010/0016732 (U.S. patent application Ser. No. 12/505,462) filed on Jul. 17, 2009, titled "Method and Apparatus for Neural-Signal Capture to Drive Neuroprostheses or Control Bodily Function";

U.S. patent application Ser. No. 12/693,427 filed Jan. 25, 2010, titled "Optical Stimulation of the Brainstem and/or Midbrain, including Auditory Areas" (now U.S. Pat. No. 8,744,570 issued Jun. 3, 2014);

U.S. Provisional Patent Application No. 61/349,813 filed May 28, 2010, by Jonathon D. Wells et al., titled "Laser-Based Nerve Stimulators for, e.g., Hearing Restoration in Cochlear Prostheses";

U.S. Provisional Patent Application No. 61/381,933 filed Sep. 10, 2010, by Jonathon D. Wells et al., titled "Laser-Based Nerve Stimulators for, e.g., Hearing Restoration in Cochlear Prostheses and Method";

U.S. patent application Ser. No. 12/890,602 filed Sep. 24, 2010, by Jonathon D. Wells et al., titled "Laser-Based Nerve Stimulators for, e.g., Hearing Restoration in Cochlear Prostheses and Method" (now U.S. Pat. No. 8,792,978 issued Jul. 29, 2014);

U.S. Provisional Patent Application No. 61/349,810 filed May 28, 2010, by Jonathon D. Wells et al., titled "Implantable Infrared Nerve Stimulation Devices for Peripheral and Cranial Nerve Interfaces";

U.S. Provisional Patent Application No. 61/386,461 filed Sep. 24, 2010, by Jonathon D. Wells et al., titled "Implantable Infrared Nerve Stimulation Devices for Peripheral and Cranial Nerve Interfaces";

U.S. patent application Ser. No. 13/117,121 filed May 26, 2011, by Jonathon D. Wells et al., titled "Implantable Infrared Nerve Stimulation Devices for Peripheral and Cranial Nerve Interfaces";

U.S. patent application Ser. No. 13/117,122 filed May 26, 2011, by Jonathon D. Wells et al., titled "Cuff Apparatus and Method for Optical and/or Electrical Nerve Stimulation of Peripheral Nerves" (now U.S. Pat. No. 8,652,187 issued Feb. 18, 2014);

U.S. patent application Ser. No. 13/117,125 filed May 26, 2011, by Jonathon D. Wells et al., titled "Nerve-Penetrating Apparatus and Method for Optical and/or Electrical Nerve Stimulation of Peripheral Nerves";

U.S. patent application Ser. No. 13/117,118 filed May 26, 2011, by Jonathon D. Wells et al., titled "Optical Bundle Apparatus and Method for Optical and/or Electrical Nerve Stimulation of Peripheral Nerves" (now U.S. Pat. No. 8,864,806 issued Oct. 21, 2014);

U.S. patent application Ser. No. 13/204,610 filed Aug. 5, 2011, by Michael E. Friend et al., titled "OCULAR IMPLANT AND METHOD FOR TRANSMISSION OF NERVE-STIMULATION LIGHT" (now U.S. Pat. No. 8,709,078 issued Apr. 29, 2014);

U.S. Provisional Patent Application 61/511,020 filed Jul. 22, 2011 by Ryan C. Stafford, titled "METHOD AND APPARATUS FOR OPTIMIZING AN OPTICALLY STIMULATING COCHLEAR IMPLANT", U.S. Provisional Patent Application 61/511,048 filed Jul. 22, 2011 by Ryan C. Stafford, titled "BROAD WAVELENGTH PROFILE TO HOMOGENIZE THE ABSORPTION PROFILE IN OPTICAL STIMULATION OF NERVES", and U.S. Provisional Patent Application 61/511,050 filed Jul. 22, 2011 by Ryan C. Stafford et al., titled "OPTICAL COCHLEAR IMPLANT WITH ELECTRODE(S) AT THE APICAL END FOR STIMULATION OF APICAL SPIRAL GANGLION CELLS OF THE COCHLEA", each of which is incorporated herein by reference in its entirety.

FIELD OF THE INVENTION

The invention relates generally to methods and apparatus for nerve stimulation, and more particularly to image processing and emission of optical signals (such as with pulsed infrared light) for stimulation of nerves in a human's eyes to obtain a sensation of vision.

BACKGROUND OF THE INVENTION

For many patients suffering from retinal degenerative diseases such as advanced or age-related macular degeneration (AMD) and retinitis pigmentosa (RP) there has been little hope for maintaining vision. Every year, 700,000 new cases of AMD in the U.S. are diagnosed and 10% of those patients will become legally blind. There are presently no cures for these debilitating diseases, and, at best, current treatments only slow the disease progression. The overall social and economic impact of AMD and RP is immense and the importance of treating blindness is profound as this is a problem of significant scope and breadth. There is an unmet need to treat this ailment by developing a visual prosthetic with a large number (e.g., thousands) of stimulation channels to realistically restore sight using infrared light to stimulate the retinal nerves. Advanced macular degeneration and retinitis pigmentosa are both degenerative diseases that degrade vision in patients and eventually can lead to blindness.

Researchers have artificially stimulated various parts of the human nervous system for many years as a way to restore lost or damaged neural function of various systems in the human body. Neuroprosthetic devices circumvent non-functioning physiological structures (hair cells in the ear, rods and cones in the eye) which would normally transduce an external stimulus (sound, light) into an action potential. Presently, there are numerous efforts underway to develop neuroprostheses to restore sight at various interventional anatomical locations: in the subretina, the epiretina, the optic nerve and in the visual cortex. These devices apply an electric current pulse to stimulate the neurons of the visual system which is inherently hindered by a lack of spatial selectivity. Electrical current spread leads to imprecise nerve stimulation and limits the ability of the neuroprosthesis to restore function. The limitation of spatial selectivity is based on fundamental physical principles of electrical stimulation. To date, after 20 years of development, electrical implants are just now hoping to make the jump to 64-channel systems from 16-channel systems. This is far less than the thousands of channels estimated to be needed for a good vision prosthetic. The technology is further limited by the fact that physical contact is required with tissue, which can lead to damage over time. Implantation of a complex powered device in very close proximity to sensitive neural tissue forms a significant drawback to this approach, making it impossible to update the technology without further risky surgeries.

There have been rudimentary attempts to stimulate the retinal nerves with electrical signals, which are being conducted by various groups globally. For example, the Argus™ II implantable device, by Second Sight Medical Products, Inc., 12744 San Fernando Road—Building 3, Sylmar, Calif. 91342, U.S.A., which is intended to treat profoundly blind people suffering from degenerative diseases such as RP. The Second Sight Medical Products, Inc. Argus™ II system works by converting video images captured from a miniature camera, housed in the patient's glasses, into a series of small electrical pulses that are transmitted wirelessly to an epiretinal prosthesis array of electrodes implanted inside the eye on the retina. These pulses then stimulate the retina's remaining cells resulting in the corresponding perception of patterns of light in the brain. Patients supposedly learn to interpret these visual patterns thereby gaining some functional vision.

U.S. Pat. No. 7,079,900 issued Jul. 18, 2006 to Greenberg et al., titled "Electrode Array for Neural Stimulation," is incorporated herein by reference. Greenberg et al. describe a retinal prosthesis to restore color vision by electrically stimulating areas of undamaged retinal cells, which remain in patients with lost or degraded visual function. There are three main parts: one is external to the eye, the second part is internal to the eye, and the third part communicates between those two parts. The external part has color imaging means (CCD or CMOS video camera), an eye-tracker, a head-motion tracker, a data processor, a patient's controller, a physician's local controller, a physician's remote controller, and a telemetry means. The color data is processed in the video data processing unit and encoded by time sequences of pulses separated by varying amounts of time, and also with the pulse duration being varied in time. The basis for the color encoding is the individual color code reference. Direct color stimulation is another operational basis for providing color perception. The electrodes stimulate the target cells so as to create a color image for the patient, corresponding to the original image as seen by the video camera. The physician's test unit can be used to set up or evaluate and test the implant during or soon after implantation.

U.S. Pat. No. 7,914,842 issued Mar. 29, 2011 to Greenberg et al., titled "Method of Manufacturing a Flexible Circuit Electrode Array," is incorporated herein by reference. Greenberg et al. describe polymer materials and electrode array bodies for neural stimulation, especially for retinal stimulation to create vision. The method lays down a polymer layer, applies a metal layer to the polymer and pattern to create electrodes and leads, and applies a second polymer layer over the metal layer and pattern to leave openings for electrodes. The array and its supply cable are a single body.

Electrical stimulation represents a major challenge in developing implantable devices with long-term system performance while reducing their overall size. The Boston Retinal Implant Project has identified long-term biocompatibility as one of the most significant challenges to be met in order to develop a successful retinal prosthesis. For example, U.S. Pat. No. 6,324,429 issued Nov. 27, 2001 to Shire et al., titled "Chronically Implantable Retinal Prosthesis," is incorporated herein by reference. Shire et al. describe a chronically implantable retinal prosthesis for the blind which will restore some useful vision to patients over at least several degrees of their former field of view. These thin, strong, and flexible epiretinal devices are constructed of or encapsulated in known biocompatible materials which will have a long working life in the eye's saline environment. The function of the implants is to electrically stimulate the ganglion cell layer at the surface of the retina using controlled current sources. Due to the exceptionally low mass of the implant and its flexible, nearly planar form, patient discomfort and fluid drag caused by the implant minimized. These physical attributes also substantially reduce the potential of harm to the most delicate structure of the eye, the retina, and therefore enhance the long term safety and biocompatibility of the device. Since no micro-cables are required to be attached to the device, and its overall form and edges are rounded, the device is not expected to stress the retina during chronic implantation. A provision is also made for nutrients to reach the retinal cells underneath the device for their long-term health.

U.S. Pat. No. 7,908,010 issued Mar. 15, 2011 to Greenberg et al., titled "Retinal Prosthesis with Side Mounted Inductive Coil," is incorporated herein by reference. Greenberg et al.

describe a retinal prosthesis with an inductive coil mounted to the side of the eye by means of a strap around the eye. This allows for close coupling to an external coil and movement of the entire implanted portion with movement of the eyeball.

Electrical stimulation, as described in the above devices and patents, is limited since the spread of electricity does not allow separate or independent stimulation of individual retinal nerve cells or even small-enough groups of nerve cells for sharp or clear vision. This electrical-stimulation technology is severely limited, as electricity spreads in human tissue and thus will severely limit the number of stimulation sites. Electrical stimulation thus greatly limits the number of sites that could be separately stimulated. Additionally, the electrical-stimulation approach will require implantation of a powered (e.g., an electrically powered) device, which has significantly difficult issues associated with obtaining power into the eye and using the power by devices in the eye.

An implant has been developed which refocuses the light normally aimed at the fovea region of the retina to the periphery of the retina. This approach is limited as there is a high degree of integration on the periphery of the fovea that, again, will severely limit resolution.

Other work is being done in the area of optogenetics wherein a virus is used to genetically sensitize nerve cells to certain wavelengths of light, e.g., PCT publication WO 2010/011404 A2 titled "Vectors for Delivery of Light-Sensitive Proteins and Methods of Use," which is incorporated herein by reference. Attempts have been made to sensitize nerve cells to optical light via injection of foreign DNA (optogenetic engineering). This area may have some potential, however it will require significant development work, it involves injecting a virus into nerve tissue (which may have significant side effects and FDA-approval issues), and the virus is only partially taken up by nerve cells.

Materials that are compatible with the eye are described in U.S. Pat. No. 6,254,637 to Jin Hak Lee et al., titled "Artificial Cornea and Implantation Thereof"; U.S. Pat. No. 6,391,055 to Yoshito Ikada et al., titled "Artificial Cornea"; U.S. Pat. No. 6,976,997 to Noolandi et al., titled "Artificial Cornea"; U.S. Pat. No. 7,857,849 to David Myung et al., titled "Artificial corneal implant"; and U.S. Pat. No. 7,909,867 to David Myung et al., titled "Interpenetrating Polymer Network Hydrogel Corneal Prosthesis"; each of which is incorporated herein by reference in its entirety.

Numerous digital-light-projection micro-electro-mechanical-system (MEMS) devices exist. For example, U.S. Pat. No. 4,566,935 issued to Hornbeck on Jan. 28, 1986, titled "Spatial Light Modulator and Method," is incorporated herein by reference in its entirety. Hornbeck described methods of fabrication of spatial light modulators (SLMs) with deflectable beams by plasma etching after dicing of a substrate into chips, each of the chips an SLM. Various architectures available with such plasma etching process were disclosed and include metal cloverleafs for substrate addressing, metal flaps formed in a reflecting layer over a photoresist spacer layer, and torsion-hinged flaps in a reflecting layer.

As another MEMS-display example, U.S. Pat. No. 7,776,631 issued to Miles on Aug. 17, 2010, titled "MEMS Device and Method of Forming a MEMS Device," and is incorporated herein by reference in its entirety. Miles described light in the visible spectrum being modulated using an array of modulation elements, and control circuitry connected to the array for controlling each of the modulation elements independently, each of the modulation elements having a surface which is caused to exhibit a predetermined impedance characteristic to particular frequencies of light.

U.S. Pat. No. 7,177,081 issued to Tomita et al. on Feb. 13, 2007, titled "High Contrast Grating Light Valve Type Device," and is incorporated herein by reference in its entirety. Tomita et al. describe a grating light valve with a plurality of spaced reflective ribbons that are spatially arranged over a substrate with reflective surfaces. The grating light valve is configured to optimize the conditions for constructive and destructive interference with an incident light source having a wavelength $\lambda$. The grating light valve preferably has a set of movable active ribbons alternating between the set of stationary bias ribbons. In operation, active ribbons are moved by a multiple of $\lambda/4$ to switch between the conditions for constructive and destructive interference.

U.S. Pat. No. 4,720,189 issued Jan. 19, 1988 to Heynen et al., titled "Eye-Position Sensor," is incorporated herein by reference in its entirety. Heynen et al. describe an eye-position sensor for use in an eye-activated optical transducer in which a spatial filter is used to modify light reflected from the eye to form a substantially rectangular pattern on a quadrennial array of contiguous sensors. This arrangement provides a substantially linear change in the output signal from the sensors in response to an equivalent movement of the eye.

U.S. Pat. No. 6,055,110 issued Apr. 25, 2000 to Kintz et al., titled "Compact Display System Controlled by Eye Position Sensor System," is incorporated herein by reference in its entirety. Kintz et al. describe a virtual image display system is provided which is made thinner through the use of an immersed beam splitter, and in one embodiment, total internal reflection. The display system includes an imaging surface on which a source object is formed, a first optical element having a reflective function and a magnification function, a second optical element having a magnification function and an immersed beam-splitting element positioned between the first and second optical elements, the immersed beam-splitting element including a beam splitter surrounded by an optically transparent material having a refractive index greater than air. An illumination source projects the source object formed at the imaging surface through the optically transparent material to the beam splitter. The beam splitter reflects the projected source object to the first optical element. The first optical element magnifies the projected source object and reflects a magnified virtual image of the projected source object to the beam splitter. The magnified virtual image traverses the beam splitter to the second optical element which magnifies the magnified virtual image to produce a compound magnified virtual image of the source object.

Yet, there remains a need in the art for an improved prosthesis and method for stimulating vision nerves to obtain a vision sensation that is more useful for the person.

BRIEF SUMMARY OF THE INVENTION

The present invention uses infrared nerve-stimulation (INS) technology that exploits infrared light (and/or other optical wavelengths) to cause action potentials in nerve cells in the eye. In recent years, optical-stimulation technology has been developed to stimulate nerves. This INS technology can achieve much higher precision and selectivity of stimulation than is possible using electrical current to trigger nerve action potentials. In some embodiments, the present technology uses pulsed, infrared lasers to excite the neural tissue next to the retina directly and without tissue damage. The advent of this technology represents a paradigm shift in artificial nerve stimulation because it allows a high degree of spatial selectivity of neural stimulation without the need for tissue contact.

The present invention provides a prosthetic system and method for restoring vision that was lost to advanced macular degeneration (AMD), retinitis pigmentosa (RP), or other causes. Infrared-light nerve stimulation (INS) is a technology that uses infrared light to trigger nerve action potentials (NAPs) in various nerves of an animal. The cells being stimulated are not necessarily the retina cone and rod cells themselves, which retina cone and rod cells are normally associated with receiving visible light (having wavelengths in the range of about 400 nm to about 700 nm) and that emit NAPs based on the visible light received to these cells. Instead, the cells stimulated by the present invention are typically cells in and/or near the nerves leading from the retina. The present invention leverages INS but applies it in a new manner. For the present invention, INS is used to stimulate the retinal nerves (those nerves between the light-sensitive cones and rods of the retina (the usual source of nerve action potentials for sight) and the optic nerve that exits the eye) of a person (the patient). These retinal nerves are essentially insensitive to visible light; however, nerve-action potential signals can be triggered by application of pulsed light, particularly light that has an infrared wavelength in the range of about 1800 nm to about 1900 nm. In some embodiments, images are first captured with a miniaturized camera and translated into infrared-light stimulation signals (i.e., changed from signals representing visible-light colors and intensities at each of an array of pixel positions, into a series of signal pulses having durations, repetition frequencies, and positions that may be different than the positions and temporal intensities that would directly correspond to the original image positions and intensities) that are then transmitted into the eye from a two-dimensional (2D) vertical-cavity surface-emitting laser (VCSEL) array (e.g., a grid of rows and columns of independently operable vertical-cavity surface-emitting lasers) or other suitable light source(s) and imaging modalities.

In the present invention, the wavelength(s), power(s) and/or energy(s) of the light and/or light pulses emitted from the laser elements in the VCSEL array, and the locations toward which the light is directed are optimized in order to most efficiently stimulate the retinal nerves (i.e., to obtain the desired nerve response) without damaging the nerves being stimulated and without drawing too much power from the power supply of the prosthesis. In some embodiments, the camera(s), processor(s), and VCSEL array(s) are all packaged into a pair of eyeglasses-like device or other headwear that is worn by the person. In some embodiments, in order to facilitate propagation of the infrared stimulation light to the retinal nerves, a passive light-focussing-and-transmitting implant (e.g., a polymer conduit) is surgically implanted within the eye of the patient. In some embodiments, this implant is made of an acrylic, or other suitable polymer, glass, or other material, that transmits well in the infrared (IR) region, and which is commonly used for certain ocular implants or specifically developed (i.e., having the desired specific gravity, focussing, transparency, bio-compatibility characteristics and the like) for use with the present invention. In some embodiments, this ocular implant also includes one or more lenses, and in order to appropriately focus and direct the path of the infrared stimulation light. In some embodiments, the implant length extends a considerable distance through the posterior chamber of the eye such that the optical path distance of the stimulating light within vitreous humor is minimized (in some embodiments, while maintaining a sufficient layer or film of vitreous humor at the back of the eye for the proper physiological functioning of the retina and optic nerves). In some embodiments, the implant is anchored in the region of the lens, while in other embodiments, a mount on one or more other surfaces of the eye is included.

In some embodiments, the sources of infrared (for stimulating nerves from the light-sensing cells that no longer function) and visible light (for sending conventional visible-light image information to the light-sensing cells that continue to function) are physically configured in a display that moves with the eye (e.g., FIGS. 6A-6C and 8, which include electromechanical actuators or the like to position the display(s) and camera(s) in different locations and angular directions, or FIGS. 7A-7D, which include light-beam scanners to sweep the infrared simulation sources and visible light sources); adjusting the geometry of image acquisition and image projection (left/right, angle, up/down, longitudinal (focus)); sensing a direction of gaze and adjusting stimulation light geometries accordingly. In some embodiments, cylinder focus (astigmatism) is also corrected by the displays of the present invention (e.g., in some embodiments, by inserting a lens or other optics that provide the required correction).

In some embodiments, the present invention provides one or more devices for focusing stimulation light. In some such embodiments, the device(s) project, onto and/or into the eye, visible points of light (fiducials) that are then imaged by a camera or other imager from outside the eye to assist the focusing of the stimulation light source to the desired nerves to be stimulated. In some such embodiments, the device(s) project stimulation light onto the sclera of the outer surface of the eye and correlate this projection to infer where light would focus on the back of the eye, and/or to determine the direction of gaze.

In some such embodiments, the device(s) project the stimulation light toward the back of the eye, and the camera or other imager obtains images of the tissue at the back of the eye, with the stimulation light projected thereon, from outside the eye, and these images are used to assist the focusing of the stimulation light source to the desired nerves to be stimulated, or use a camera located on the headwear and imaging the side of the eye to observe and/or follow some feature of the eye or fiducial device to assist the focusing of the stimulation light and/or to determine the direction of gaze. In some such embodiments, the device(s) project ultrasound signals (e.g., chirps or pulses) toward the eye and sense the return signal to assist the focusing of the stimulation light.

The infrared visual prosthetic (IVP) system of the present invention is an improved approach over conventional electrical stimulation or other methods conventionally used to stimulate vision nerves since the IVP increases the possible number of stimulation sites by at least an order of magnitude over electrical stimulation, and the IVP does not require implantation into the patient of a powered device. Additionally, if optogenetic technology is eventually successful, technology of the IVP stimulation device may be directly applicable.

BRIEF DESCRIPTION OF THE DRAWINGS

FIG. 1A demonstrates an image 101 of lily pads and flowers using 48 channels, 432 channels, and 6912 channels.

FIG. 1B1 is a much-enlarged schematic representation of a small portion of an array 102 of stimulation sources having both IR-nerve-stimulation VCSELs and visible light emitters.

FIG. 1B2 is an enlarged schematic representation of a larger portion of array 102 of stimulation sources having both IR-nerve-stimulation VCSELs and visible light emitters.

FIG. 1C is a schematic representation of a system 103 with a hardware- and operating-environment having an implanted passive optical-transmission device 200, an optional externally worn device 111 and a customization console computer 20.

FIG. 2 is a cut-away perspective view of a nerve-stimulation system 101 for an eye 90 that illustrates an implanted ocular unit 200, according to some embodiments of the invention.

FIG. 4A is a high-level flow diagram of the image generating system 401, according to some embodiments of the invention.

FIG. 4B is a high-level flow diagram of the image generating system 402, according to some embodiments of the invention.

FIG. 4C is a high-level data-flow diagram of the image generating system 402, according to some embodiments of the invention.

FIG. 5B is a flow diagram of image processing 502 according to some embodiments of the invention.

FIG. 5C is a schematic representation of a system 503 having an implanted device 110, an externally worn device 111 and a transceiver 71 of customization console computer such as shown in FIG. 1C.

FIG. 6A is a top cross-section view of a movable-external-light-source subsystem 601 in a first position relative to the eye of a patient, according to some embodiments of the present invention.

FIG. 6B is a top cross-section view of a movable-external-light-source subsystem 601 in a second position relative to the eye of a patient.

FIG. 6C is a top cross-section view of a movable-external-light-source subsystem 601 in a third position relative to the eye of a patient.

FIG. 7A is a top cross-section view of a scannable-external-light-source subsystem 701 emitting light toward a first position and toward a second position of a reflecting array 751 relative to the eye of a patient, according to some embodiments of the present invention.

FIG. 7D is a top cross-section view of a MEMS-array scannable-external-light-source subsystem 704 having a plurality of emitters (such as diode or fiber lasers), according to some embodiments of the present invention.

DETAILED DESCRIPTION OF THE INVENTION

Figure 2:
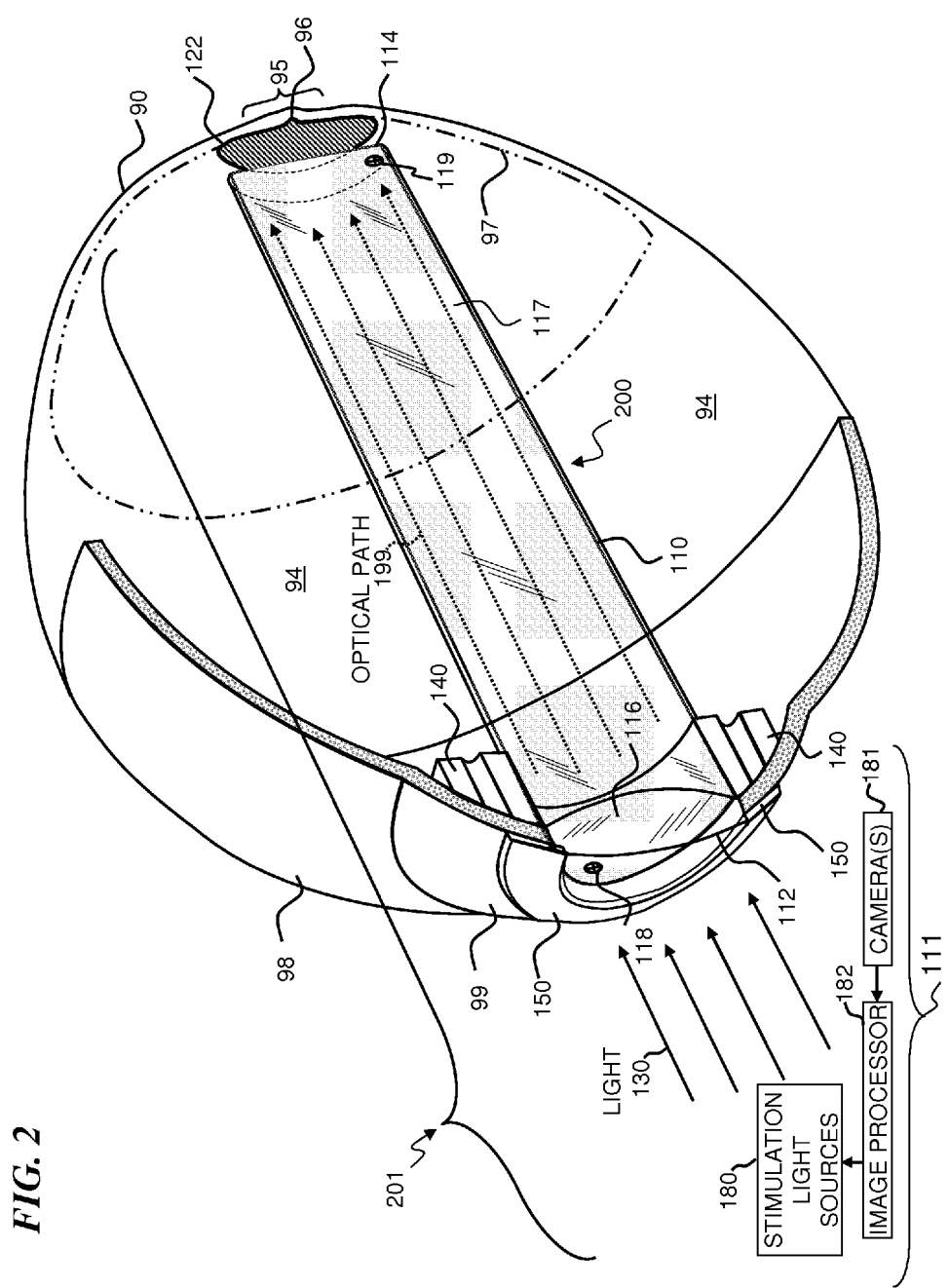

Although the following detailed description contains many specifics for the purpose of illustration, a person of ordinary skill in the art will appreciate that many variations and alterations to the following details are within the scope of the invention. Very narrow and specific examples are used to illustrate particular embodiments; however, the invention described in the claims is not intended to be limited to only these examples, but rather includes combinations and subcombinations of features shown in the various figures and descriptions. The invention includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

In recent years, a pioneering technology has been developed to stimulate nerves, which can achieve much more precision and selectivity of stimulation than electric current. This technology uses pulsed, infrared lasers to excite the neural tissue directly without tissue damage. The advent of this technology represents a paradigm shift in artificial nerve stimulation because it allows a high degree of spatial selectivity of neural stimulation without the need for tissue contact.

Research is in process of using infrared-light nerve stimulation (INS) technology to provide hearing restoration using an implantable prosthetic in the cochlea and vestibular systems. In cochlear implants, the higher spatial selectivity of INS allows the implant to better mimic the natural stimulation of the neurons which results in superior hearing fidelity. This approach also has added benefits over existing technologies including residual hearing preservation and faster healing from surgery because light can be directed through the round window. The enhancement achievable over electrical stimulation has only been demonstrated in animals. Additional work is necessary to provide safety and efficacy data and develop the device hardware and software for nerve stimulation such that it will be ready for clinical trials.

Transitioning INS technology to the retina has some unique challenges not found in the cochlea, however along with those challenges are some unique opportunities. The higher level of specificity enabled by INS technology can potentially result in a prosthetic containing tens of thousands of channels. For the retina, high quantities of channels are especially important for realistic sight restoration.

FIG. 1A demonstrates an image 101 of lily pads and flowers using 48 channels, 432 channels, and 6912 channels. Most of today's electrical optical stimulators are working in the range of 64 to 256 channels. Higher numbers of channels are needed to restore vision to more realistic levels.

FIG. 1B1 is a much-enlarged schematic representation of a small portion of an array 102 of stimulation sources having both IR-nerve-stimulation light source(s) (in some embodiments, VCSELs that emit infrared light of one or more wavelengths that are effective to stimulate nerve action potential signals in nerves when applied as a pulse of sufficient energy and properly focussed) and visible-light source(s) (in some embodiments, VCSELs that emit visible light of one or more wavelengths (such as red, green and blue)), used by some embodiments of the present invention. In some embodiments, array 102 is fabricated as a VCSEL array on one or more chips, wherein emitters of the various wavelengths are arranged in an array such as shown in this example, which shows three IR wavelengths and three visible wavelengths interleaved with one another. In some embodiments, more or fewer different IR wavelengths are used (in some embodiments, a single IR wavelength is used), and in some embodiments, more or fewer visible wavelengths are used. In some other embodiments, such as described below in the description of FIG. 7D a plurality of emitters (such as diode or fiber lasers) are used in a scanned projection system (e.g., in some embodiments, one, two, or three IR lasers 711 and one, two, or three visible light lasers 711' emit collimated light toward a system 704 of MEMS-deflection mirrors that create the spatial pattern of each wavelength that is projected into ocular implant 200 (see FIG. 2) and then onto the retinal nerves and/or retina of the patient). In such a system that combines both visible light emitters (to stimulate those areas of the light-sensitive rods and cones in the retina that remain functional in a patient with partial loss of vision) and IR nerve-stimulation light emitters (that stimulate the nerves leading from the non-functional rods and cones, which nerves generally overlie rods and cones that may or may not still be functional), these embodiments of the present invention provide the novel capability of stimulating both the remaining functional rod and cone cells that underlie the layer of nerve cells that conduct signals toward the optical nerve, as well as the nerve cells leading from non-functional rod and cone cells. In some embodiments, the present invention provides the ability to test the effectiveness of each emitter or group of emitters, and using the results of the testing to reprogram the controller to recalibrate the algorithms that convert image into stimulation signals and change which areas of the eye receive visible-light signals and which areas of the eye receive IR light signals. These visible-stimulation and IR-stimulation areas can overlap (to provide additional stimulation capabilities when desired) or not overlap (selectively turning off various of the stimulation sources, particularly to save electrical power by not using emitters that provide no function (providing little or no IR nerve stimulation to nerves from functioning visible-light-sensitive cells and little or no visible light to cells that have been found by testing to be non-functioning), and/or to prevent overheating of tissue by reducing the frequency of nerve-stimulation pulses to areas that have recently been stimulated to near a limit of the tissue's ability to dissipate local heating, and/or to turn off the stimulation when the patient blinks or closes their eyes). In some embodiments, array 102 is as described further in the description of FIG. 1B2 below.

FIG. 1B2 is an enlarged schematic representation of a larger portion of array 102 of stimulation sources having both IR-nerve-stimulation VCSELs and visible light emitters. In some embodiments, array 102 includes a first plurality of IR-nerve-stimulation pixels (IR1 pixels, wherein the IR1 emitters 131 are indicated with a clear background and are always "OFF" until configuration software enables them, while the IR1 emitters 141 are selectively enabled and indicated with a hashed background in FIG. 1C), a second plurality of IR-nerve-stimulation pixels (IR2 pixels, wherein the IR2 emitters 132 are indicated with a clear background and are always "OFF" until configuration software enables them, while the IR2 emitters 142 are selectively enabled and indicated with a hashed background in FIG. 1C), and a third plurality of IR-nerve-stimulation pixels (IR3 pixels, wherein the IR3 emitters 133 are indicated with a clear background and are always "OFF" (inactivated for stimulation and not powered for extended periods of time) until configuration software enables them, while the IR3 emitters 143 are "ON" (activated for use and selectively enabled based on the input image) and indicated with a hashed background in FIG. 1C). In some embodiments, array 102 includes a plurality of IR1 pixels 131 that are turned OFF (inactivated for stimulation and not emitting regardless of the received image for extended periods of time, e.g., until a recalibration and/or change in stimulation mode) and a plurality of IR1 pixels 141 that are turned ON (activated for use and selectively emitting, depending on the received image and the image processing that may temporarily inhibit emitting based on heuristics in the image-processing algorithm that enhance certain features such as edges and motion, and/or to prevent local overheating). In some embodiments, array 102 includes a plurality of IR2 pixels 132 that are turned OFF (not emitting regardless of the received image) and a plurality of IR2 pixels 142 that are turned ON (selectively emitting, depending on the factors described above). In some embodiments, array 102 includes a plurality of IR3 pixels 133 that are turned OFF (not emitting regardless of the received image) and a plurality of IR3 pixels 143 that are turned ON (selectively emitting, depending on the factors described above). In some embodiments, array 102 includes a plurality of visible-red-light pixels 136 that are turned OFF (not emitting regardless of the received image), a plurality of visible-red-light pixels 146 that are turned ON (selectively emitting, depending on the factors described above), a plurality of visible-green-light pixels 137 that are turned OFF (not emitting regardless of the received image), a plurality of visible-green-light pixels 147 that are turned ON (selectively emitting, depending on the factors described above), a plurality of visible-blue-light pixels 138 that are turned OFF (not emitting regardless of the received image), and a plurality of visible-blue-light pixels 148 that are turned ON (selectively emitting, depending on the factors described above). Note that in the example shown in FIG. 1B2, the processor has been programmed to turn off most of the visible-light pixels in the center of this portion of the array 102 (such that these turned-off pixels do not emit regardless of the received image), and turn on (selectively enable for light emission depending on the received image) most of the visible-light pixels around the edges of this portion of the array 102, and the processor has been programmed to turn on (selectively enable for light emission depending on the received image) most of the IR-light pixels in the center of this portion of the array 102, and turn off (such that these turned-off pixels do not emit regardless of the received image) most of the IR-light pixels around the edges of this portion of the array 102. Such a configuration may be used for a patient with macular degeneration where the macula has stopped functioning. Note that even in such a situation, there may be some cells in the mostly IR-light-stimulation area that are still functional as to visible light and thus selective ones of the visible-light emitters are enabled, and there may be nerves over the mostly visible-light stimulation areas that one desired to stimulate and thus some of the IR emitters around the edges are then enabled for selective emission to stimulate those nerves.

In some embodiments, the device of the present invention has a plurality of stimulation modes that can be selectively activated, and different subsets of the emitters 102 are activated for use in the different modes of operation. For example, in some embodiments, a first set of modes of operation can be optimized for reading and enhance the contrast of the image, change the received text to black-and-white or other contrasting colors, enhance edges and smooth edges, and similar image processing that makes text images more readable and understandable (in some embodiments, the device can also be set to a text-reading calibration mode and generate various test patterns, and elicit and receive user input to customize the image-processing algorithm to best suit the individual user for one or more different text-reading situations, such that the user can later select one of one-or-more different text-reading modes based on the text to be read). In some embodiments, one or more additional modes of operation can be calibrated and selectively activated based on the environment and/or user input, such that the image processing can pre-process the video images to suit a particular activity, such as recognizing various colors useful for cooking food and identifying types of food or defects in the food, or for recognizing different denominations of money, or for walking and bicycling outdoors, or for participating in various social or business activities, or for manipulating and assembling parts as part of a job or hobby. In some embodiments, two or more image-processing modes can be selectively activated at the same time, such that the device of the present invention can simultaneously be suited for combined activities (such as card playing, which can benefit from both shape and text enhancement as well as color differentiation). In some embodiments, the device can receive user input in conventional ways (such as from voice commands or manual mode selection) to select its operational mode, and/or by automatically recognizing the need for a particular mode (such as by sensing when the eye-direction (gaze) of the user is directed towards an area of the field of view that has text or particular symbols, or that faces of people are in the field of view), and the device then automatically changes its mode of operation to enhance image processing to suit that environment. Thus, in some of the plurality of image-processing modes, different subsets of the visible-light emitters 146, 147, and/or 148 and of the infrared-light emitters 136, 137, and/or 138 can be activated or de-activated, based on the content of the environmental video images received and on the various areas of nerves to be stimulated (where rods and cones are not properly functioning) and areas of rod and cones to receive visible wavelengths of light.

In some embodiments, the present invention provides a test-and-recalibration system for the patient to use by themselves, or with the help of a care-giver, that provides an interactive test (e.g., a program that goes through a set of images displayed on a personal computer (such as a desktop computer, iPad®-like tablet, smart phone or the like), and based on patient feedback of the perceptions of those images, recalibrates which pixels are to be IR-stimulation pixels and which are to be visible-light emitters, and also frequently recalibrates the image-processing algorithms to optimize the perceived vision each week, each day, or each hour, or on an activity-by-activity basis (e.g., in some embodiments, different algorithms are used for reading, for household chores, or for outdoor walking and the like). In some embodiments, this recalibration program determines which nerves (or areas of visual perception) are stimulated by which IR-stimulation pixel position, and stores a set of mapping parameters that are used by the image processor (for example, in some embodiments, a system and algorithm such as illustrated in FIG. 5B described below) to assist in mapping the received environmental image to particular ones of the nerves to be stimulated. For example, in some embodiments, the test program displays a set of images on the screen of a smart phone, which is programmed to receive user input (e.g., by touch screen input or voice input) as to what the patient user perceives, and the smart phone (system 103 of FIG. 1C) then wirelessly transmits mapping parameters to the externally worn device (device 111 of FIG. 1C), which uses the mapping parameters to convert the data from the received environmental image to particular ones of the stimulation sources to stimulate the desired nerves to achieve the vision sensations for the patient in subsequent use of the now-recalibrated device 111. In other embodiments, the device 111 itself generates the series of test stimulation signals that include both visible-light stimulation signals and IR-light stimulation signals, and device 111 itself receives feedback input from the patient (either directly (such as by voice input, motion input or touch input) or indirectly (by wireless signals from another device such as a smart phone or personal computer), and device 111 performs the necessary recalibration and re-mapping functions and stores the parameters needed for future mapping in the device 111 as used in a particular environment. In yet other embodiments, the device 111 itself generates the series of test stimulation signals that include both visible-light stimulation signals and IR-light stimulation signals, and device 111 itself receives feedback input from imaging the patient's eye (e.g., optically sensing physiological nerve signals that are generated in various nerves as a result of the stimulation, such as by the systems and methods described in U.S. Patent Publication No. 2010/0016732 (U.S. patent application Ser. No. 12/505, 462) filed on Jul. 17, 2009, titled "Method and Apparatus for Neural-Signal Capture to Drive Neuroprostheses or Control Bodily Function," which is incorporated herein by reference), and does the needed recalibration periodically or in real time (on a periodic (weekly, daily, hourly, or based on a given activity, such as reading versus walking outside) or continuous basis throughout the day of usage).

In other embodiments, (not shown) two or more chips of VCSEL arrays or other emitters (for example, one chip with an array of VCSELs all emitting just one wavelength of IR-stimulation light signal, and one chip with an array of MEMS mirrors used to reflect three visible wavelengths (e.g., red, green, and blue), or one chip with an array of VCSELs all emitting just one wavelength of IR-stimulation light signal, another chip with an array of VCSELs all emitting red-stimulation light signal, another chip with an array of VCSELs all emitting green-stimulation light signal, and another chip with an array of VCSELs all emitting blue-stimulation light signal) are provided (e.g., side-by-side) and projection optics are used to superimpose pixel images from the plurality of sources each including an array of one or more wavelengths of emitters. In some such embodiments, the sources include both array emitters (such as a two-dimensional VCSEL array, wherein each pixel of light of a given wavelength from that "object" (the 2D source of light) is imaged into the back of the eye, such that each pixel of the "image" (the 2D image of the "object" as projected into the back of the eye) comes from a different VCSEL in the array) and projection emitters (wherein a plurality of the pixels of light imaged into the back of the eye all come from a single emitter (e.g., a diode or fiber laser, or a wavelength-conversion device such as a non-linear frequency doubler of 1064-nm IR light that is frequency doubled to 532-nm green light), wherein the light from that single emitter is scanned to different pixel positions at the back of the eye by a system of MEMS mirrors, for example, as described below).

FIG. 1C is an overview schematic diagram of a hardware- and operating-environment (or system) 103 that is used in conjunction with embodiments of the invention. The description of FIG. 1C is intended to provide a brief, general description of suitable computer hardware and a suitable computing environment in conjunction with which the invention may be implemented. In some embodiments, aspects of the invention are described in the general context of computer-executable instructions, such as program modules, that are stored on computer-readable media and that are executed by a computer, such as a microprocessor residing in an implanted device (located within a patient) and/or in an external device worn by the patient and/or personal computer that is/are wirelessly linked to the implanted device. Generally, program modules include routines, programs, objects, components, data structures, and the like, that perform particular tasks or implement particular abstract data types.

In some embodiments, system 103 includes an optometrist- and/or user-control console computer 20 that is programmable and that has a wireless transceiver 71 that allows wireless control (i.e., reprogramming of the remote microprocessors) of the externally worn device 111 (which includes a programmed microcontroller), that transmits pulsed laser nerve-stimulation laser-light signals 130 to the passive implanted device (ocular unit 200). In some embodiments, application programs 36 stored on a computer-readable storage device (e.g., optical disk 31 (CDROM, DVD, Blu-ray® Disc (BD), or the like), magnetic or FLASH storage device 29 (e.g., floppy disk, thumb drive, SDHC (Secure Digital High Capacity, one type of FLASH memory) memory card or the like), and/or a storage device 50 connected to a remote computer 49 that connects to computer 20 across a local-area network 51 or a wide-area network 52 such as the internet) contain instructions and/or control structures (such as look-up tables, control parameters, databases and the like) that are processed and/or transmitted into the externally worn device 111 to control its operation by methods of the present invention described herein. In some embodiments, the applications programs 36 are partially executed in the computer 20 and/or the externally worn device 111.

Accordingly, in some embodiments, an optometrist and/or user can adjust parameters of the externally worn device 111 to customize its operation to a much greater extent than is possible with a conventional electrical-stimulation ocular implant, because externally worn device 111 has a far greater number of parameters that can be finely adjusted (e.g., pulse width, amplitude, frequency, wavelength, polarization, wavelength profile, beam profile, beam angle, and, the like). In some embodiments, the applications programs 36 contain a substantial amount of safety control code that runs in computer 20 to guide the optometrist and/or user to adjust the parameters of the externally worn device 111 and to help prevent operation that might harm the patient or damage the externally worn device 111 (such as what might occur if too much optical energy were applied in a concentrated small area of the nerve layers of the retina or within too short a period of time, or if overheating occurred in the device 111 due to too many vertical-cavity surface-emitting lasers (VCSELs) next to one another being activated in a short period of time).

Although many of the embodiments herein have light-emitting elements that include VCSELs (vertical-cavity surface emitting lasers) implemented as electrically pumped semiconductor diode lasers, other embodiments of the present invention use edge-emitting semiconductor diode lasers, optically pumped semiconductor lasers, optically pumped optical-fiber lasers, light-emitting diodes, superluminescent devices, or any other suitable light source. Some embodiments use wavelengths in the range of 1.75 microns to 2 microns, other embodiments use any other suitable wavelengths.

Moreover, those skilled in the art will appreciate that the invention may be practiced with other computer-system configurations, including hand-held devices, multiprocessor systems, microprocessor-based or programmable consumer electronics, network PCs, minicomputers, mainframe computers, and the like. The invention may also be practiced in distributed computer environments where tasks are performed by remote processing and input-output (I/O) devices that are linked through a communications network. In a distributed-computing environment, program modules may be located in both local and remote storage devices.

As shown in FIG. 1C, in some embodiments, the hardware- and operating-environment includes optometrist- and/or user-control console computer 20, or a server 20, including a processing unit 21, a system memory 22, and a system bus 23 that operatively couples various system components including the system memory 22 to the processing unit 21. In some embodiments, there may be only one, or in other embodiments, there may be more than one processing unit 21, such that the processor of computer 20 comprises a single central-processing unit (CPU), or a plurality of processing units, commonly referred to as a multiprocessor or parallel-processing environment. In various embodiments, computer 20 may be implemented using a conventional computer, a distributed computer, or any other type of computer including those embedded in cell phones, personal-data-assistant devices or other form factors.

The system bus 23 can be any of several types of bus structures including a memory bus or memory controller, a peripheral bus, and a local bus using any of a variety of bus architectures. The system memory can also be referred to as simply the memory, and includes read-only memory (ROM) 24 and random-access memory (RAM) 25, a basic input/output system (BIOS) 26, containing the basic routines that help to transfer information between elements within the computer (or server) 20, such as during start-up, may be stored in ROM 24. The computer 20 further includes a hard disk drive 27 for reading from and writing to a magnetic hard disk, a removable-media drive or FLASH controller 28 for reading from or writing to a removable magnetic floppy-disk or FLASH storage device 29, and an optical disk drive 30 for reading from or writing to a removable optical disk 31 (such as a CDROM, DVD, Blu-ray Disc (BD) or other optical media).

The hard disk drive 27, magnetic disk drive 28, and optical disk drive 30 couple with a hard disk drive interface 32, a magnetic disk drive interface 33, and an optical disk drive interface 34, respectively. The drives and their associated computer-readable media provide non-volatile, non-ephemeral storage of computer-readable instructions, data structures, program modules and other data for the computer 20. It should be appreciated by those skilled in the art that any type of computer-readable media which can store data that is accessible by a computer, such as magnetic cassettes, FLASH memory cards, digital video disks, Bernoulli cartridges, random-access memories (RAMs), read-only memories (ROMs), redundant arrays of independent disks (e.g., RAID storage devices) and the like, can be used in the exemplary operating environment.

A plurality of program modules that implement the optimization methods of the present invention can be stored on the hard disk, magnetic or FLASH storage device 29, optical disk 31, ROM 24, or RAM 25, including an operating system 35, one or more application programs 36, other program modules 37, and program data 38. A plug-in program containing a security transmission engine for the present invention can be resident on any one, or on a plurality of these computer-readable media.

In some embodiments, a user (e.g., the optometrist or the patient) enters commands and perception information into the computer 20 through input devices such as a keyboard 40, pointing device 42 or other suitable device such as a microphone (not shown). Other input and/or output devices (not shown) can include a microphone, joystick, game pad, satellite dish, scanner, speaker, headphones or the like. These other input and output devices are often connected to the processing unit 21 through a serial port interface 46 that is coupled to the system bus 23, but can be connected by other interfaces, such as a parallel port, game port, or a universal serial bus (USB), a monitor 47 or other type of display device can also be connected to the system bus 23 via an interface, such as a video adapter 48. The monitor 47 can display a graphical user interface for the optometrist and/or user. In addition to the monitor 47, computers typically include other peripheral output devices (not shown), such as speakers and printers.

In some embodiments, the monitor 47 or other image-output device outputs calibration images, and system 20 elicits and receives user input (e.g., as to perception sensations) into the computer 20 through keyboard 40 or any other suitable input device, for example such as described above. In some embodiments, the calibration images include images having lines, edges, object movement, colors and/or other features at various angles, positions and motions in the field of vision, and the user input is used to map the regions of nerves that provide various visual sensations to the patient. This retinal map (i.e., a map that indicates which sensations result from optical stimulation of each small area of the nerve layers of the retina) is then stored in a computer-readable data structure (CRDS) and used in the transformation of image information (intensities and/or colors at each pixel location) into pulsed IR stimulation light at each of a plurality of areas on the nerve layers of the retina.

In some embodiments, computer 20 operates in a networked environment using logical connections to one or more remote computers or servers, such as remote computer 49. These logical connections are achieved by a communication device coupled to or a part of the computer 20; the invention is not limited to a particular type of communications device. The remote computer 49 can be another computer, a server, a router, a network PC, a client, a peer device or other common network node, and typically includes many or all of the elements described above relative to the computer 20, although only memory storage device 50 and application programs 36 have been illustrated in FIG. 1C. The logical connections depicted in FIG. 1C include local-area network (LAN) 51 and wide-area network (WAN) 52. Such networking environments are commonplace in office networks, enterprise-wide computer networks, intranets and the Internet, which are all types of networks. In some embodiments, the local computer 20 has merely a user interface (e.g., a browser) to a remote system 49 located remote from the user and accessed across the internet, wherein the system 49 performs the control and calculations of the calibration process. In some embodiments, the method of the calibration process is embodied as instructions and/or data structures stored on a computer-readable storage medium that causes the method to be performed when the instructions are read and executed by a suitable information-processing system.

When used in a local-area networking (LAN) environment, the computer 20 is connected to the LAN 51 through a network interface, modem or adapter 53, which is one type of communications device. When used in a wide-area networking (WAN) environment such as the internet, the computer 20 typically includes an adaptor or modem 54 (a type of communications device), or any other type of communications device, e.g., a wireless transceiver, for establishing communications over the wide area network 52, such as the internet. The modem 54, which may be internal or external, is connected to the system bus 23 via the serial port interface 46. In a networked environment, program modules depicted relative to the personal computer 20, or portions thereof, (or those stored in the externally worn device 111 or the implanted ocular unit 200) can be stored in the remote memory storage device 50 of remote computer, or server 49 and accessed over the internet or other communications mechanism. Note that the transitory signals on the internet may move stored program code from a non-transitory storage medium at one location to a computer that executes the code at another location by the signals on one or more networks. The program instructions and data structures obtained from a network or the internet are not "stored" on the network itself, but are stored in non-transitory storage media that may be connected to the internet from time to time for access. It is appreciated that the network connections shown are exemplary and in some embodiments, other mechanisms of, and communications devices for, establishing a communications link between the computers may be used including hybrid fiber-coax connections, T1-T3 lines, DSL's, OC-3 and/or OC-12, TCP/IP, microwave, WAP (wireless application protocol), and all other electronic media through standard switches, routers, outlets and power lines, as the same are known and understood by one of ordinary skill in the art.

The hardware and operating environment in conjunction with which embodiments of the invention may be practiced has been described. The computer 20 in conjunction with which embodiments of the invention can be practiced can be a conventional computer, a distributed computer, or any other type of computer; the invention is not so limited. Such a computer 20 typically includes one or more processing units as its processor, and a computer-readable medium such as a memory. The computer 20 can also include a communications device such as a network adapter or a modem, so that it is able to communicatively couple to other computers, servers, or devices.

In some embodiments, one or more parts of system 103 elicits and receives input from a user, and based on the input, modifies, adjusts or executes one or more of the methods of the present invention as described herein.

The INS technology as disclosed in the invention herein also enables the use of an external stimulator, thus eliminating the need to implant a powered device (only a passive implant device) and allowing for easier upgrades as the stimulator technology advances since the active stimulator device is not implanted. Because the tissue of the eye normally absorbs at infrared light wavelengths, a passive implant will have to be surgically placed in the eye to create a "light pipe" from the external stimulator array to the retina nerve cells. Infrared light from an external infrared stimulating array passes through an implanted "light pipe" that allows it to be imaged or focused on the retina, especially the macula and fovea. In some embodiments, the main light-transmission material of the passive implant is an acrylic such as PMMA, which is used today for ocular implants lenses. The implant allows the infrared light to reach the retina which would normally be highly absorbed by the fluid of the eye.

In some embodiments, the system provides sight restoration to patients blinded by retinitis pigmentosa (RP) and age-related or advanced macular degeneration (AMD). It utilizes infrared-nerve-stimulation (INS) technology to cause action potentials in retinal nerve cells in the in the retina, especially the macula and fovea regions. In some embodiments, two 2D (2-dimensional) VCSEL arrays (one for each eye) are used to generate the stimulation patterns at the stimulating infrared wavelength (1400-1900 nm). In some embodiments, images are captured with miniaturized cameras and converted into stimulation patterns in an image processor. In order for the stimulating light to be able to reach the retinal nerves, an ocular implant is placed in the eyeball. The ocular implant is made of a material that is both biocompatible and highly transmissive to the stimulating light. In some embodiments, the ocular implant contains optics that serve to focus the light on the back on the retina. In some embodiments, the VCSEL arrays, camera, processor, and power supply are all packaged in a headset or set of eyeglasses to be worn by the patient. In some other embodiments, portions of the system (e.g., the power supply and/or processor) are packaged separate from the headset or glasses that include the VCSEL arrays.

FIG. 2 is a cut-away perspective view of a nerve-stimulation system 201 for an eye 90 that illustrates an implanted ocular unit 200, according to some embodiments of the invention. Appendix A., titled "Ocular Implant and Method for Transmission of Nerve-Stimulation Light" of related U.S. Provisional Patent Application No. 61/514,894 filed Aug. 3, 2011 by Michael E. Friend et al., titled "SIGHT-RESTORING VISUAL PROSTHETIC AND METHOD USING INFRARED NERVE-STIMULATION LIGHT", incorporated herein by reference, describes various ocular implants and methods for transmission of nerve-stimulation light through the eye.

In some embodiments, the ocular unit 200 includes a light-transparent pathway or "image pipe" 110 (which includes an optional lens system 116 and a transparent body 117) for transmitting a stimulation pattern of infrared light 130 from an external stimulator array 180 through the eye 90 along optical path 199, the ocular unit 200 having a light-receiving anterior end 112 closest to the eye's anterior surface and extending to a posterior end 114 of image pipe 110 closer to the fovea 96 than to the eye's anterior surface, transmitting light and/or projecting image 122 onto the retina 97, including onto the macula 95 and fovea 96. In some embodiments, the curved anterior surface of image pipe 110 acts as the anterior-end focussing element and no separately formed lens 116 is needed.

As used herein, an "image pipe" is an optical device that forms an image just beyond its posterior end (e.g., when an image pipe of the present invention is implanted in the eye, the image is formed on the nerves at the anterior surface of the retina) that is based on light 130 entering the anterior end. In some embodiments, an image pipe includes internal imaging components such as lenses, holographs, fiber optics or fiber-optic bundles, or the like, which assist in providing a focussed image at the retina. In other embodiments, the image pipe is simply a transparent path that allows external imaging components to form the image on the nerves at the front surface of the retina. Because some embodiments of the present invention use single-wavelength infrared lasers, holographic imagers are well suited to form images through such an image pipe.

In some embodiments, the image pipe 110 is substantially transparent to at least some infrared wavelengths of light between about 1000 nm and about 2000 nm, and in particular, is substantially transparent to those infrared wavelengths output by the source lasers of the stimulation apparatus. In some embodiments, the image pipe 110 has a substantially cylindrical shape such as shown in FIG. 2, such that both ends of the image pipe 110 have substantially the same diameter. In some embodiments, the image pipe 110 is formed from a biocompatible-transparent-thermoplastic material such as poly(methyl methacrylate) (PMMA), or the like. In some embodiments, such as shown in FIG. 2, the light-receiving anterior end 112 of ocular unit 200 replaces at least a portion of the cornea 99 of the eye and thus forms part of the anterior surface of the eye.

Poly(methyl methacrylate) (PMMA) is a transparent thermoplastic. PMMA has been sold under many different names including Plexiglas®, Lucite® and Perspex®. PMMA is substantially transparent (i.e., a given thickness of about a centimeter or more passes a majority of incident light) to visible light (having wavelengths of 400 nm to 700 nm) and infrared light (IR) having wavelengths from about 700 nm to about 2800 nm. Colored or tinted PMMA varieties allow specific IR wavelengths to pass while blocking visible light and/or other IR wavelengths.

In some embodiments, ocular unit 200 is surgically secured in place to the cornea 99 and/or sclera 98 in the eye with anchoring collar 140 and hydrogel skirt 150. In some embodiments, the implant is sewn (or stapled or otherwise anchored) to the ciliary muscle or secured to other internal parts of the eye to hold it securely in place. Ocular unit 200 extends well into the vitreous humor 94, which is less transparent than is image pipe 110 to certain infrared light wavelengths useful for nerve stimulation.

The posterior end 114 of the image pipe 110 is closer to the fovea than the front of the eye. In some embodiments, image pipe 110 has a length such that the posterior end 114 of the image pipe 110 is near the retina 97 in the region of the macula 95 and fovea 96. In some embodiments, the image pipe 110 does not contact the retina 97, in order to leave a pathway for the vitreous humor 94 to circulate and nourish the cells of the retina. In some embodiments, the posterior end 112 is positioned close enough to the retina 97 and fovea 96 such that the remaining vitreous humor is thin enough and transparent enough that infrared light output from the posterior end of the image pipe 110 will be sufficiently intense to cause retinal-nerve stimulation (i.e., triggering of nerve action potentials in the nerves of the retina due to impinging pulses of infrared light).

In some embodiments, the ocular image pipe 110 is solid material. PMMA has a higher density than the vitreous humor. To more closely match the density of the vitreous humor, some embodiments of image pipe 110 include at least one hollow portion such that the overall density of the image pipe 110 is the same as the density of the surrounding vitreous humor and the center of mass of the image pipe 110 coincides with the center of rotation of the eye, in order that the image pipe 110 does not tend to move relative to the eye with movement. In some embodiments, the hollow portion is filled with an inert gas. In some embodiments, the hollow portion is filled with a low-pressure gas having a pressure of no more than about 1000 Torr. In some embodiments, the hollow portion is in the light path of the light path and at least one end of the hollow portion is shaped to form a lens to focus the infrared light on nerves of the retina.

The placement, size, and shape of the hollow portion in the image pipe 110 is used in some embodiments to not only match the density of the vitreous humor but to also control the center of gravity to help provide a more stable implant the is resistant to movement of the head or eyeball. In some embodiments, the light-transmitting portion of image pipe 110 is solid material and the hollow portion is formed in a peripheral portion outside and surrounding the light-transmitting path. This configuration reduces the number of optical interfaces in the light path. In some embodiments, the light-transmitting portion of image pipe 110 is solid material and the hollow portion is formed symmetrically around a peripheral portion outside and surrounding the light-transmitting path, such that regardless of whether the person's head is upright or is lying on one side, there is no rotational or other force acting to move the implant (i.e., image pipe 110) relative to the eye. In other embodiments, the hollow portion is formed in (or is very slightly larger in) a top portion of image pipe 110, in order to help keep the image pipe 110 upright and in the desired position when the patient's head is upright.

In some embodiments, one or both ends of the image pipe 110 are shaped to focus the external stimulator array signals 130 on the retina and fovea. In some embodiments, there is an external light source 180 that emits IR-wavelength stimulation light 130. For example, in some embodiments, source 180 includes a two-dimensional array of vertical-cavity surface-emitting lasers (VCSEL-array) that form an IR stimulator, which provides IR light 130 into the anterior end 112 of the ocular implant 200. In some embodiments, the user has an ocular unit 200 implanted in each eye, and the system provides there is a separate external two-dimensional array IR stimulator source 180 for each eye, wherein the two separate images help provide three-dimensional images to the brain through each eye's ocular unit 200. In some embodiments, image pipe 110 includes a lens or lens system 116, with a different index of refraction than the rest of image pipe 110, to focus the image on the retina 97. In some embodiments, the lens system 116 inverts the incoming image and focuses the image on the retina. In some other embodiments, the lens system 116 is non-inverting and directs diverging, collimated, or converging light on the nerve-tissue layer of the retina 97. In some embodiments, the image pipe 110 and its lens 116, in combination with an external laser image-generation device 180 and its image processor(s) 182 and one or more cameras in camera system 181, produce an infrared image on the retina, similar to the inverted optical-wavelength image a normal human eye. Since the human brain will automatically accustom itself to any image consistently formed on the retina whether or not the image is inverted, the camera system 181, image processor 182 and stimulation light sources 180 can be configured to form the image as inverted or not according to the preferences of the user. In some embodiments, camera system 181 includes at least one camera directed toward the user's eye (e.g., to determine the locations of indicia 118 and/or 119) to determine the location and/or direction of movement of the gaze of the user, and this image of the eye (or of the indicia 118/119) is processed by image processor system 182 in order to control the position of the stimulation light sources that are generating the stimulation light signals 130, in order to position the projected pattern of stimulation light onto the desired locations on retina 122. In some embodiments, the array of light sources 180 themselves are physically moved to the desired position, while in other embodiments, different ones of the light sources 180 that are already in the desired positions are activated.

In some embodiments, the ocular unit 200 has at least one indicia mark to facilitate detection of the eye's position. In some embodiments, the ocular unit has at least one indicia mark 118 on the anterior end to facilitate external detection of the position of the eye and the pointing directions. In some embodiments, the ocular unit 200 has at least one indicia mark 119 on the posterior end to facilitate external detection of the position of the eye and the pointing directions. In some embodiments, one or more indicia marks are placed on both the anterior end posterior end, and/or on one or more other locations on the ocular unit 200. In some embodiments the location and/or orientation of the implant is determined, for example, by obtaining an image of, or detecting reflected or fluorescent light from, the indicia mark or marks 118 and/or 119 and the external stimulator array signals are adjusted to compensate for the position of the eye (e.g., the image or pattern is moved such that the desired nerve tissue continues to be stimulated). In some such embodiments, an eye-position processor in the external image processor 182 uses an "inward-pointing" camera in camera system 181 (i.e., a camera pointed toward the user to obtain an image of the eye and/or indicia 118/119) to detect movement or position of the user's eye(s), and generates control signals that direct an external camera view (i.e., the direction in which the camera system 181 is pointing, or if a very-wide-angle lens and/or multiple cameras are used, which of the images obtained by camera system 181 is used), providing a more realistic sensation of "looking around" to the user, instead of requiring movement of the user's entire head to obtain different images. In some embodiments, a plurality of "outward-pointing" cameras is included in camera system 181 (i.e., a plurality of cameras pointed toward different directions in the environment surrounding user to obtain a plurality of images from which to select based on the detected direction of the user's gaze).

In some embodiments, (e.g., FIG. 2) the stimulation system 101 includes a camera 181, an image processor 182, and a laser output device 180 that outputs stimulation light signals into ocular implant 200. In some embodiments, the image processor 182 receives images signals from camera 181 that represent pixel-intensity values for light received at each of a plurality of pixels in a rectangular array of pixels. In some embodiments, the rectangular array of pixels detected by camera 181 includes a plurality of pixels for each of a plurality of colors (each having a range of wavelengths).

In some embodiments, such as FIG. 2, the image processor 182 receives the camera 181 output and converts the image information into electrical signals that drive the IR stimulation light sources 180. The brightness of a particular pixel in the field of vision is not directly converted to the brightness of a particular IR stimulation signal. The individual stimulation signals that are transmitted into the eye are converted by the image processor from a series of image brightness signals for each pixel into pulse repetition patterns that represent brightness wherein the pulse repetition patterns stimulate the nerves of the retina to produce actions potentials. In some embodiments, and individual stimulating laser signal is off, or on at a below-threshold level, and then pulsed on in order to trigger the nerve action signal in the retina. The stimulation signals generated are pulse representations of the brightness of a pixel, and the pulse intensity is not a representation of the brightness, similar to how the nerves in a normal eye work. The image processor converts image pixel brightness, and in some embodiments converts the image pixel color, into what will become IR stimulating nerve pulse patterns, where the pulse patterns are of substantially the same height and the same length sufficient to generate nerve axons but at different pulse rate frequencies and directed to different locations on the retina in order to accomplish the perception of vision to the patient. In some embodiments, the perception of different colors is reproduced for the patient by stimulating particular nerve axons of the retina rather than by modifying the frequency of the IR stimulating light.

In some embodiments, the nerve stimulating pulse repetition rate of the optical signal is about 1 to 2 pulses per second. In some embodiments, the nerve stimulating pulse repetition rate of the optical signal is about two to five (2 to 5) pulses per second. In some embodiments, the nerve stimulating pulse repetition rate of the optical signal is about five to ten (5 to 10) pulses per second. In some embodiments, the nerve stimulating pulse repetition rate of the optical signal is about 10 to 20 pulses per second. In some embodiments, the nerve stimulating pulse repetition rate of the optical signal is about 20 to 50 pulses per second. In some embodiments, the nerve stimulating pulse repetition rate of the optical signal is about 50 to 100 pulses per second. In some embodiments, the nerve stimulating pulse repetition rate of the optical signal is about 100 to 200 pulses per second. In some embodiments, the nerve stimulating pulse repetition rate of the optical signal is about 200 to 500 pulses per second. In some embodiments, the nerve stimulating pulse repetition rate of the optical signal is about 500 to 1000 pulses per second. In some embodiments, the nerve stimulating pulse repetition rate of the optical signal is about 1000 to 2000 pulses per second. In some embodiments, the nerve stimulating pulse repetition rate of the optical signal is more than about 2000 pulses per second.

In some embodiments of the apparatus, the one or more lasers output an infrared signal having a radiant exposure of the retina of no more than 4 J/cm$^2$ per nerve-action-potential (NAP) response generated. In some embodiments of the apparatus, the one or more lasers output an infrared signal having a radiant exposure of the retina of no more than 3 J/cm$^2$ per NAP response generated. In some embodiments of the apparatus, the one or more lasers output an infrared signal having a radiant exposure of the retina of no more than 2 J/cm$^2$ per NAP response generated.

In some embodiments of the apparatus, the one or more lasers output an infrared signal having a radiant exposure of the retina of between about 5 J/cm$^2$ and about 6 J/cm$^2$ per NAP response generated. In some embodiments of the apparatus, the one or more lasers output an infrared signal having a radiant exposure of the retina of between about 4 J/cm$^2$ and about 5 J/cm$^2$ per NAP response generated. In some embodiments of the apparatus, the one or more lasers output an infrared signal having a radiant exposure of the retina of between about 3 J/cm$^2$ and about 4 J/cm$^2$ per NAP response generated. In some embodiments of the apparatus, the one or more lasers output an infrared signal having a radiant exposure of the retina of between about 3 J/cm$^2$ and about 3.5 J/cm$^2$ per NAP response generated. In some embodiments of the apparatus, the one or more lasers output an infrared signal having a radiant exposure of the retina of between about 2.5 J/cm$^2$ and about 3 J/cm$^2$ per NAP response generated. In some embodiments of the apparatus, the one or more lasers output an infrared signal having a radiant exposure of the retina of between about 2 J/cm$^2$ and about 2.5 J/cm$^2$ per NAP response generated. In some embodiments of the apparatus, the one or more lasers output an infrared signal having a radiant exposure of the retina of between about 1.5 J/cm$^2$ and about 2 J/cm$^2$ per NAP response generated. In some embodiments of the apparatus, the one or more lasers output an infrared signal having a radiant exposure of the retina of between about 1 J/cm$^2$ and about 1.5 J/cm$^2$ per NAP response generated. In some embodiments of the apparatus, the one or more lasers output an infrared signal having a radiant exposure of the retina of between about 0.5 J/cm$^2$ and about 1 J/cm$^2$ per NAP response generated. In some embodiments of the apparatus, the one or more lasers output an infrared signal having a radiant exposure of the retina of between about 0.2 J/cm$^2$ and about 0.5 J/cm$^2$ per NAP response generated. In some embodiments of the apparatus, the one or more lasers output an infrared signal having a radiant exposure of the retina of between about 0.1 J/cm$^2$ and about 0.2 J/cm$^2$ per NAP response generated.

In some embodiments, the one or more lasers output an infrared signal having an energy of less than about 2 mJ per pulse.

In some embodiments, the one or more lasers output an infrared signal providing an energy of less than about 2 mJ per pulse to the retina.

In some embodiments, the one or more lasers output an infrared signal having a pulse width of between about ten microseconds (10 μs) and about five milliseconds (5 ms).

In some embodiments, the one or more lasers output an infrared signal having a pulse width of between about 1 μs and about 10 μs. In some embodiments, the one or more lasers output an infrared signal having a pulse width of between about 10 μs and about 20 μs. In some embodiments, the one or more lasers output an infrared signal having a pulse width of between about 20 μs and about 50 μs. In some embodiments, the one or more lasers output an infrared signal having a pulse width of between about 20 μs and about 40 μs. In some embodiments, the one or more lasers output an infrared signal having a pulse width of between about 40 μs and about 80 μs. In some embodiments, the one or more lasers output an infrared signal having a pulse width of between about 80 μs and about 160 μs. In some embodiments, the one or more lasers output an infrared signal having a pulse width of between about 50 μs and about 100 μs. In some embodiments, the one or more lasers output an infrared signal having a pulse width of between about 100 μs and about 200 μs. In some embodiments, the one or more lasers output an infrared signal having a pulse width of between about 200 μs and about 500 μs. In some embodiments, the one or more lasers output an infrared signal having a pulse width of between about 200 μs and about 400 μs. In some embodiments, the one or more lasers output an infrared signal having a pulse width of between about 400 μs and about 800 μs. In some embodiments, the one or more lasers output an infrared signal having a pulse width of between about 800 μs and about 1600 μs. In some embodiments, the one or more lasers output an infrared signal having a pulse width of between about 500 μs and about 1000 μs. In some embodiments, the one or more lasers output an infrared signal having a pulse width of between about 1 millisecond (ms) and about 2 ms. In some embodiments, the one or more lasers output an infrared signal having a pulse width of between about 2 ms and about 5 ms. In some embodiments, the one or more lasers output an infrared signal having a pulse width of between about 2 ms and about 4 ms. In some embodiments, the one or more lasers output an infrared signal having a pulse width of between about 4 ms and about 8 ms. In some embodiments, the one or more lasers output an infrared signal having a pulse width of between about 8 ms and about 16 ms. In some embodiments, the one or more lasers output an infrared signal having a pulse width of between about 5 ms and about 10 ms.

Figure 3:
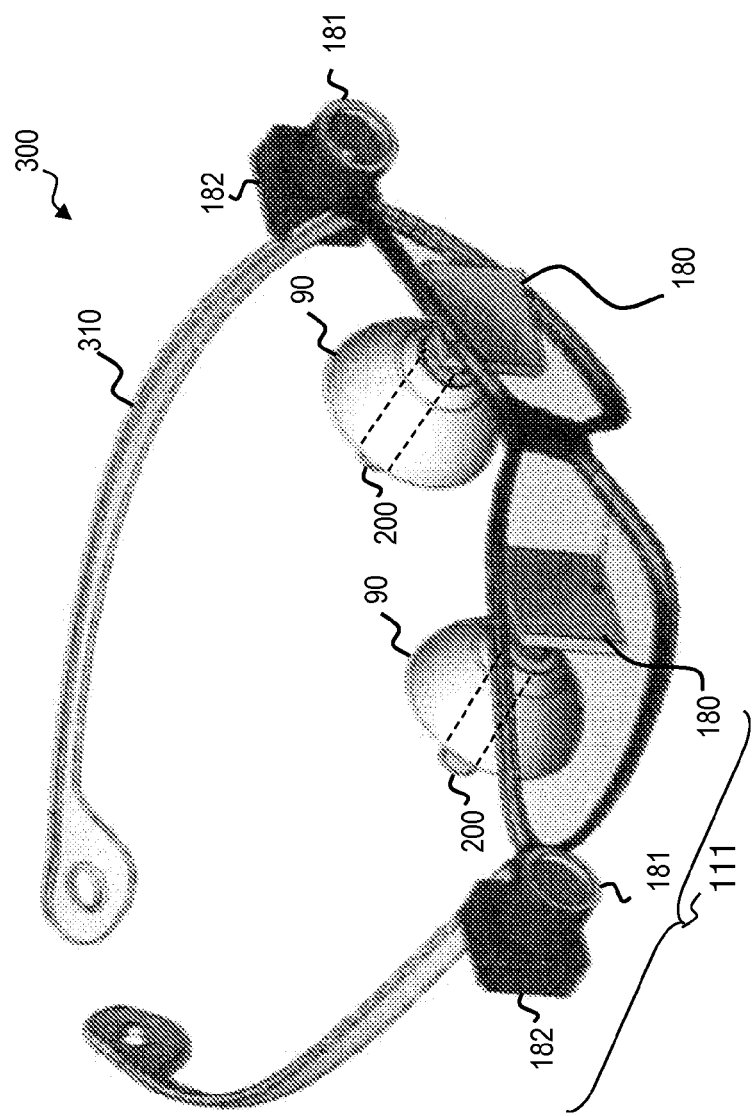
FIG. 3 is a perspective view of a nerve-stimulation system 301, according to some embodiments of the invention.

FIG. 3 is a perspective view of a nerve-stimulation system 301, according to some embodiments of the invention. Nerve-stimulation system 301 includes a headset 310 with one or more cameras 181 and one or more displays 180. In some embodiments, camera(s) capture images that are conveyed to the image processor (not shown in FIG. 3). The image processor converts the images to electrical signals that drive the display(s) 180. In some embodiments, the displays include VCSEL arrays to provide an array of infrared laser signals. In some embodiments, as demonstrated in FIG. 3, one camera and one display is used for each eye to restore stereoscopic vision with depth perception. In some embodiments, the displays 180 convert electrical signals from the image processor into a plurality of infrared laser signals that are transmitted through the eye(s) 90 using implanted ocular unit(s) 200 to stimulate NAPS in the patient's retina.

In some embodiments, the image processor and associated power supply is mounted on or in the headset 310. In some other embodiments, one or both of the image processor and associated power supply are remotely mounted, e.g., on a belt worn around the patient's waist.

In some embodiments, eye position sensors detect the position or movement of eye(s) 90 and the image processor or other mechanisms (e.g., see FIG. 6A, FIG. 6B, FIG. 6C, FIG.

7A, FIG. 7B, FIG. 7C, and FIG. 8 described below) are used to adjust the display(s) 180 to compensate for the eye movement. In some embodiments, the eye position sensors are mounted or imbedded on the display(s) 180.

FIG. 4A is a high-level flow diagram of the image generating system 401, according to some embodiments of the invention. In some embodiments, camera(s) 181 capture images that are processed by the image processor 182 into signals driving the stimulation light sources 180. Additional information provided to the image processor, in some embodiments, includes the positions of the eyes detected by eye position sensor(s) 183.

FIG. 4B is a high-level flow diagram of the image generating system 402, according to some embodiments of the invention. Patients with a partially damaged retina that is still largely light sensitive (such as when a detached retina has been reattached but the edges could not be reconnected without a gap or missing or relocated pieces, or in the case of starting macular degeneration), it is sometimes beneficial to obtain image information with camera(s) 181, detect eye position with sensor(s) 183, remap the locations of various pieces of the image information using image processor 184, and generate a visible-light image using visible-light sources 185 (using configurations such as shown in FIGS. 6A, 6B, 6C, 7A, 7B, 7C, and/or 8 or other suitable image sources), where various pieces of the image have been re-arranged in their positions, such that when projected or imaged onto the patient's remaining light-sensitive retina areas, the image is perceived by the patient's eye and brain to be a normal, or at least improved vision sensation. As one particular example, some persons with a gap in their reattached retina would normally not see the portions of the scene that land in the gap, but when the image of the scene is remapped such that parts of the scene are moved to the sensitive areas on one side of the gap and other parts of the scene are moved to the sensitive areas on the other side of the gap, a continuous scene is perceived. As another particular example, some persons with macular degeneration have lost light-sensitivity in the detail-sensing central part of the retina, but could perceive sentences in a book or newspaper if the successive letters are enlarged and scanned across the remaining light-sensitive peripheral retina area, so some embodiments of the present invention focus on printed text, acquire an image of the text, and then image processor 184 enlarges the letters and light sources 185 scan the test across the peripheral field(s) of remaining vision so that the patient can read the text. As yet another example, the eye may require changes in eye fixation direction (either microsaccades, or more large-scale changes in gaze direction), and for patients unable to provide this movement of the eye, some embodiments of the present invention move the displayed or projected image to compensate for the lack of eye movement. As still another example, binocular fixation disparity (e.g., perhaps caused by strabismus, also known as heterotropia), is a condition in which the eyes are not properly aligned with each other, and in some embodiments, the present invention independently moves the positions of the displayed or projected visible images based on the two different directions of gaze of the two eyes of the patient.

FIG. 4C is a high-level data-flow diagram of the image generating system 402, according to some embodiments of the invention. In some embodiments, camera(s) 181 acquire image data 481 (shown in this example as areas A, B, C, D, E, F, G, H, I, J, K, L, M, N, O, P). A map of the sensitive areas of the retina 490 is obtained in a calibration procedure to determine where the various light-sensitive areas (e.g., the locations 491 of the retina on either side of gap 484 (there may be more than one gap, and each sensitive area is mapped), and an image-retina mapping process is used to remap the positions of various regions of the image (in some embodiments, each region is a set of one or more pixels) so that the appropriate regions of the retina are illuminated with the corresponding regions from the image. In some embodiments, eye-position detector 184 detects the position 483 locating where in the field of possible views the gaze of the patient is directed, and this is used to further map the positions of the various regions from the original camera image. In other embodiments, the order of mapping operations are rearranged or combined. The visible light sources (e.g., display screen or image projector) 185 then create the visible-light image 485 that is imaged into the eye of the patient, and is perceived as an improved sensed vision 480 with reduced or eliminated gaps. In some embodiments, the light sources 485 comprise a display screen that moves within a range of possible X and Y positions. In other embodiments, the display is in a fixed position relative to the eye, and the image is moved to various X and Y positions on the display screen.

Figure 5A:
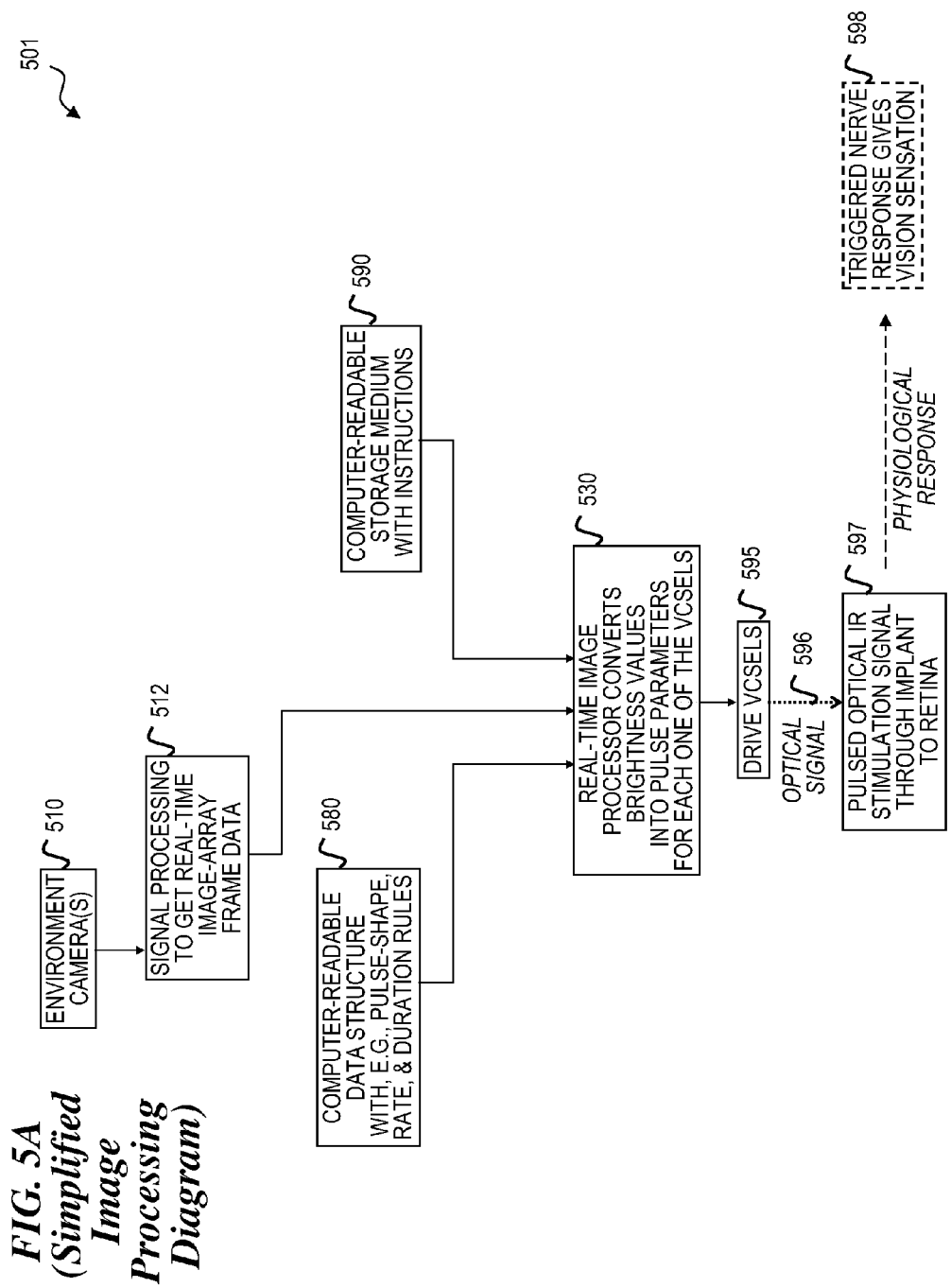
FIG. 5A is a simplified flow diagram of image processing 501 according to some embodiments of the invention.

FIG. 5A is a flow chart of a method 501, according to some embodiments of the present invention. In some embodiments of method 501, at block 510 a video signal is obtained from one or more cameras configured to obtain signals of a scene representing the visual field the patient would have if the patient could see, and to generate electrical signals that are processed by process 512 to obtain real-time data representing the image of the visual filed as an array of pixels, wherein the array of pixels representing the scene at the current time (or processing cycle) is commonly referred to as a frame. In some embodiments, the frame pixels of the scene are processed by process 530 to select which pixels will be combined within each of a plurality of bins. In some embodiments, experimental rules for visual stimulation are derived and a storage-medium having a general-rule computer-readable data structure (CRDS) 580 contains general rules for mapping image input to visual stimulation based on physiological considerations. Operation 530 takes the pixel information for the current time frame (and optionally from a predetermined number of prior time frames) and using the heat-based anti-tissue-damage-rules CRDS 580 (which limit the number of VCSELs that are allowed to be activated in any one time frame and/or within P successive time frames), along with data from VCSEL heat-based anti-device-damage-rules and rules for stimulation pulse shapes (pulse width and/or rise/fall shape) also in CRDS 580, and operation 530 generates pulse parameters for the stimulation light for each VCSEL to be activated. Operation 595 takes the pulse parameters from operation 530 and drives the VCSELs to emit stimulation signals 596 (a set of infrared optical-stimulation signal pulses) which are transmitted 597 through the ocular implant to the retina to trigger NAPs 598 providing a vision sensation. In some embodiments, a reloadable computer-readable storage medium 590 holds instructions data structures that control the operations described above.

FIG. 5B is a flow chart of a method 502, according to some embodiments of the present invention. In some embodiments of method 502, at block 510 a video signal is obtained from one or more cameras configured to obtain signals of a scene representing the visual field the patient would have if the patient could see, and to generate electrical signals that are processed by process 512 to obtain real-time data representing the image of the scene as an array of pixels, wherein the array of pixels representing the scene at the current time (or processing cycle) is commonly referred to as a frame. In some embodiments, the frame pixels of the scene are processed by process 522 to select which pixels will be combined within each of a plurality of bins, and a history of such values is stored by process 524 into data structure 586. In some embodiments, experimental rules for visual stimulation are derived and a storage-medium having a general-rule computer-readable data structure (CRDS) 584 contains general rules for mapping image input to visual stimulation based on physiological considerations. In addition, some embodiments include a patient-specific CRDS 585 that modifies or supplements the general-rule CRDS 584. In some embodiments, patient-specific CRDS 585 is derived by empirically outputting a set of visual output signals to the implanted system and eliciting and receiving feedback from the patient indicative of the sensations perceived as a result of the optical stimulation applied. In some embodiments, operation 520, based on general-rule CRDS 584 and patient-specific CRDS 585, derives a map of visual input (e.g., pixels)-to-stimulation site(s) based on the patient's feedback. In some embodiments for each successive time frame, operation 522 combines the pixel brightness values from image-processing operation 512 and the mapping rules from 520 into bin-stimulation values. In some embodiments, operation 524 stores into CRDS 586 a history of the bin and/or pixel values for most-recent P frames. Operation 530 then takes the bin information for the current time frame (and optionally from a predetermined number of prior time frames) and using the heat-based anti-tissue-damage-rules CRDS 582 (which limit the number of bins that are allowed to be activated in any one time frame and/or within P successive time frames), along with data from VCSEL heat-based anti-device-damage-rules CRDS 581 and rules for stimulation pulse shapes (pulse width and/or rise/fall shape) in CRDS 583, and operation 530 generates pulse parameters for the stimulation light for each VCSEL to be activated. Operation 595 takes the pulse parameters from operation 530 and drives the VCSELs to emit stimulation signals 596 (a set of infrared optical-stimulation signal pulses) which are transmitted 597 through the ocular implant to the retina to trigger NAPs. In some embodiments, the resulting physiological response is a set of NAPs 598 that is transmitted to the brain of the patient, and operation 518 optionally measures the nerve response and operation 519 processes a feedback signal that is fed back into operation 530. In some embodiments, a reloadable computer-readable storage medium 590 holds instructions data structures that control the operations described above.

In some embodiments, the present invention further includes eye-position cameras 514 that track where in the visual field the patient's eye is pointed. Operation 515 takes the eye-position camera information from 514 and generates control signals 516 used in operation 530 to re-map VCSELs altering the portion of the scene transmitted by the VCSELs to the patient's retina. In other embodiments, operation 515 takes the eye-position camera information from 514 and generates control signals 517 to move the VCSEL array 513 to keep it positioned in front of the ocular implant as the gaze of the patient's eye changes, as shown in FIG. 6A, FIG. 6B and FIG. 6C.

In some embodiments, process 502 includes a "fail-safe" function in operation 530 that immediately (or after a short predetermined amount of time) turns off all stimulation devices (including lasers or other optical sources) if and when communications are lost to the environment camera(s) 510.

FIG. 5C is a schematic representation of a system 503 having an implanted device 110, an externally worn device 111 and a transceiver 71 of customization console computer 20 such as shown in FIG. 1C. Elements shown here that have identical numbers as elements in FIG. 1C are described above in the description of FIG. 1C. Elements here having identical numbers as elements in FIG. 5B are described above in the description of FIG. 5B. In some embodiments, a light-source-moving device 575 (such as used in movable external light source subsystem 601 of FIG. 6A or scannable-external-light-source subsystem 701 of FIG. 7A or scannable-external-light-source subsystem 702 of FIG. 7B or MEMS-array scannable-external-light-source subsystem 703 of FIG. 7C) is coupled to light source system 180 to move the optical signal light 596 as the eye 90 moves, in order to keep the infrared stimulation aligned with the nerves that are to be stimulated. In some embodiments, eye-position-determining camera(s) 514 obtain images of the eye, and the position of the eye is calculated by the image processor 182 which then controls the light-source-moving device 575 such that the stimulation signal 596 tracks to the correct positions on the nerves at the back of the eye 90 at or near the retina 96. In some embodiments, the programming computer 20 communicates with the externally worn device 111 from time-to-time to recalibrate and/or improve the programs 590 stored therein. In some embodiments, the externally worn device 111 communicates back to programming computer 20 to download device parameters and usage characteristics such that the programming computer 20 can diagnose issues and appropriately reconfigure externally worn device 111 for best performance.

FIG. 6A, FIG. 6B and FIG. 6C are top views of an external light source 180 which in some embodiments of the present invention is a movable external light source subsystem 601, wherein the external light source moves to follow a patient's eye movements. In some embodiments, the external light source 601 subsystem emits IR-wavelength stimulation light 130. The external light source subsystem includes a light emitter 686 and, in some embodiments, a carrier 688 upon which the light emitter 686 moves. For example, in some embodiments, light emitter 688 includes a two-dimensional array of vertical-cavity surface-emitting lasers (VCSEL-array) that form an IR stimulator, which provides IR light 130 into the eye 90. In some embodiments, an eye tracking camera (for example, 514 in FIG. 5B, but not shown here) senses the side to side direction to which the eye is pointed. The light emitter 686 moves and is kept in substantially the same location relative to the front of the eye. That is, as the eye looks ahead, or side-to-side, the light emitter moves to stay in front of the eye. FIG. 6A shows the eye oriented to look toward the right, and the light emitter 686 is positioned at the right side of the carrier. FIG. 6B shows the eye oriented to look straight ahead, and the light emitter 686 is at the middle of the carrier 688. FIG. 6C shows the eye oriented to look toward the left, and the light emitter 686 is at the left side of the carrier 688. In some embodiments, the carrier 688 is a curved track in which the light emitter moves, and in some embodiments, the light emitter is moved along the track by an actuator 681. In other embodiments, the carrier is a set of mechanical linkages the move the light emitter in such a way that it stays located in front of the eye, and substantially perpendicular to the long axis of the ocular implant 200. In some embodiments, carrier 688 is configured such that light emitter 686 can be moved in a left-right x-direction, an up-down y-direction, and a forward-backward (e.g., toward the eye and away from the eye) direction, and such that the angle in which light emitted from light emitter 686 contacts the eye can be modified.

In some embodiments of the present invention, the image processor 182 further includes an actuator controller 682. The actuator controller causes the actuator 681 to move the light emitter 686 from side to side, keeping the light emitter in front of the ocular implant 200 such that image projected by light emitter stays in substantially the same position on the retina of the patient's eye as the eye looks from side to side.

In some embodiments, the image processor 182 of the nerve stimulation system controls the light emitter 686 such that the nerve stimulation light signals emitted correspond with the external scene in the direction the eye is pointing. This allows a patient to look in different directions without the need to actually rotate one's head. A nerve stimulation system with capability to allow a patient to see side-to-side simply by changing the direction in which one's eyes are pointing better simulates natural vision and provides an improved experience for the patient.

In some embodiments, the external light source 180 further includes an optical element 687 between the light emitter 686 and the eye 90. The optical element corrects for distortions in the IR light 130 from the light emitter 686 for further improve the accuracy of the nerve stimulation in the eye. In some embodiments, the optical element moves with the light emitter 686 along the carrier 688 to provide consistent optical correction in all directions of viewing.

Figure 7B:
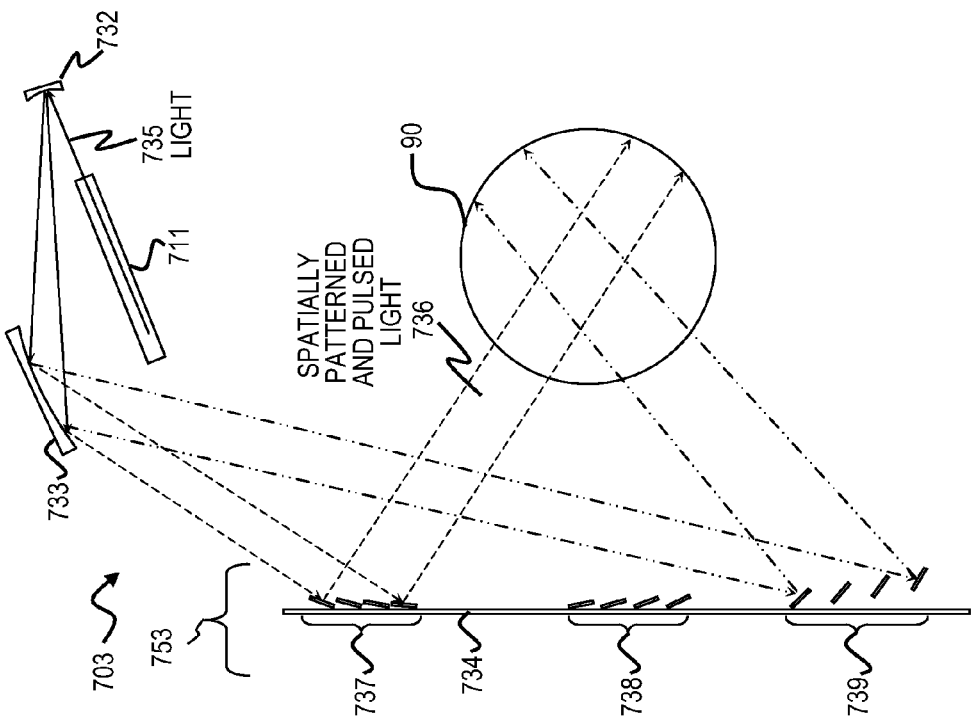
FIG. 7B is a top cross-section view of a scannable-external-light-source subsystem 702 emitting light toward a first position and toward a second position of a holographic or diffractive unit 752 based on movement of the eye of a patient, according to some embodiments of the present invention.

FIG. 7A is a top cross-section view of a scannable-external-light-source subsystem 701 emitting light toward a first position and toward a second position of a reflecting array 751 relative to the eye of a patient, according to some embodiments of the present invention. In some embodiments, system 701 includes a laser unit 711 (e.g., an optically pumped fiber-optic laser, VCSEL, or VCSEL array) that emits one or more laser beams 710 that are deflected in a first direction by angularly movable scanning minor 712 (e.g., in some embodiments, the first direction being one of a plurality of angles in a plane perpendicular to the figure sheet (e.g., in some embodiments, this moves the beam in an X direction)), and that are then that are deflected in a second direction by angularly movable scanning mirror 713 (e.g., in some embodiments, the second direction being one of a plurality of angles in a plane parallel to the figure sheet (e.g., in some embodiments, this moves the beam in an Y direction)). This type of scanning is generally called raster scanning. In some embodiments, the effective extent of the raster scanned light pattern during any one time frame is scanned across only a small portion of reflecting array 751 (the field of vision that is being acquired in the position that the eye is in during that time frame). For example, when the eye 90 is looking at the minor array 717, the light beam 710 is only scanned across the area of reflectors 717; since no stimulation of action potentials will occur for light coming from other directions, this saves power. This eye tracking and moving of the raster pattern also allows the patient to move their eyes in different directions to control the image being acquired, and system 111 will move the cameras toward the direction of gaze and generate the raster-scanned pulsed light pattern such that the pattern reaches the desired area of the retina. Similarly, if the patient's gaze is directed toward the area of reflectors 719, the system's mirrors will raster scan the pattern of IR nerve-stimulation light only towards the area of reflectors 719. In some embodiments, each area of reflectors 717, 718, 719 (and other areas of reflecting array 751 not shown here for clarity) has pixilated arrays of very small reflectors where each reflector is configured to reflect incoming light from scanning mirror 713 toward a direction into ocular implant 200. In some embodiments, a grating light valve (such as described FIG. 7B is a top cross-section view of a scannable-external-light-source subsystem 702 emitting light toward a first position and toward a second position of a holographic or diffractive unit 752 based on movement of the eye of a patient, according to some embodiments of the present invention.

Figure 7C:
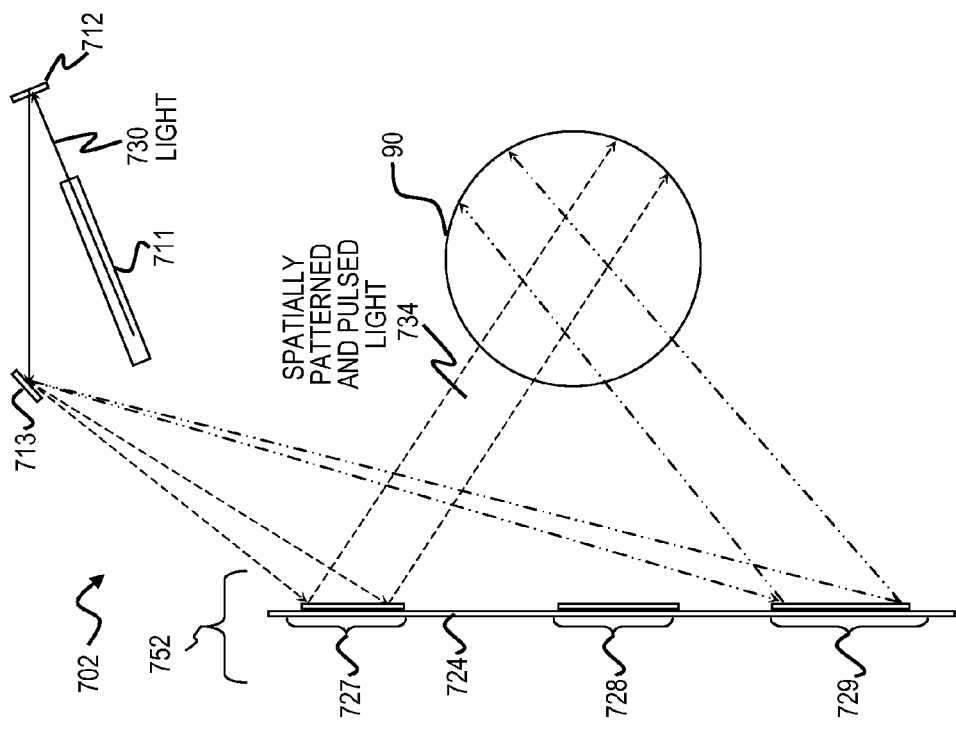
FIG. 7C is a top cross-section view of a MEMS-array scannable-external-light-source subsystem 703 emitting light toward a first position and toward a second position of a MEMS reflector unit 753 based on movement of the eye of a patient, according to some embodiments of the present invention.

FIG. 7C is a top cross-section view of a MEMS-array scannable-external-light-source subsystem 703 emitting light toward a first position and toward a second position of a MEMS reflector unit 753 based on movement of the eye of a patient, according to some embodiments of the present invention.

FIG. 7D is a top cross-section view of a MEMS-array scannable-external-light-source subsystem 704 having a plurality of emitters (such as diode or fiber lasers), according to some embodiments of the present invention, which are used in a scanned projection system (e.g., in some embodiments, one, two, or three IR lasers 711 and one, two, or three visible light lasers 711' emit collimated light toward a system 751 of MEMS-deflection mirrors that create the spatial pattern of each wavelength that is projected into ocular implant 200 (see FIG. 2) and then onto the retinal nerves and/or retina of the patient). Other than the visible light lasers 711' and their light output 710', the rest of the elements of subsystem 704 are as described for subsystem 701 (above) and as shown in FIG. 7A.

Figure 8:
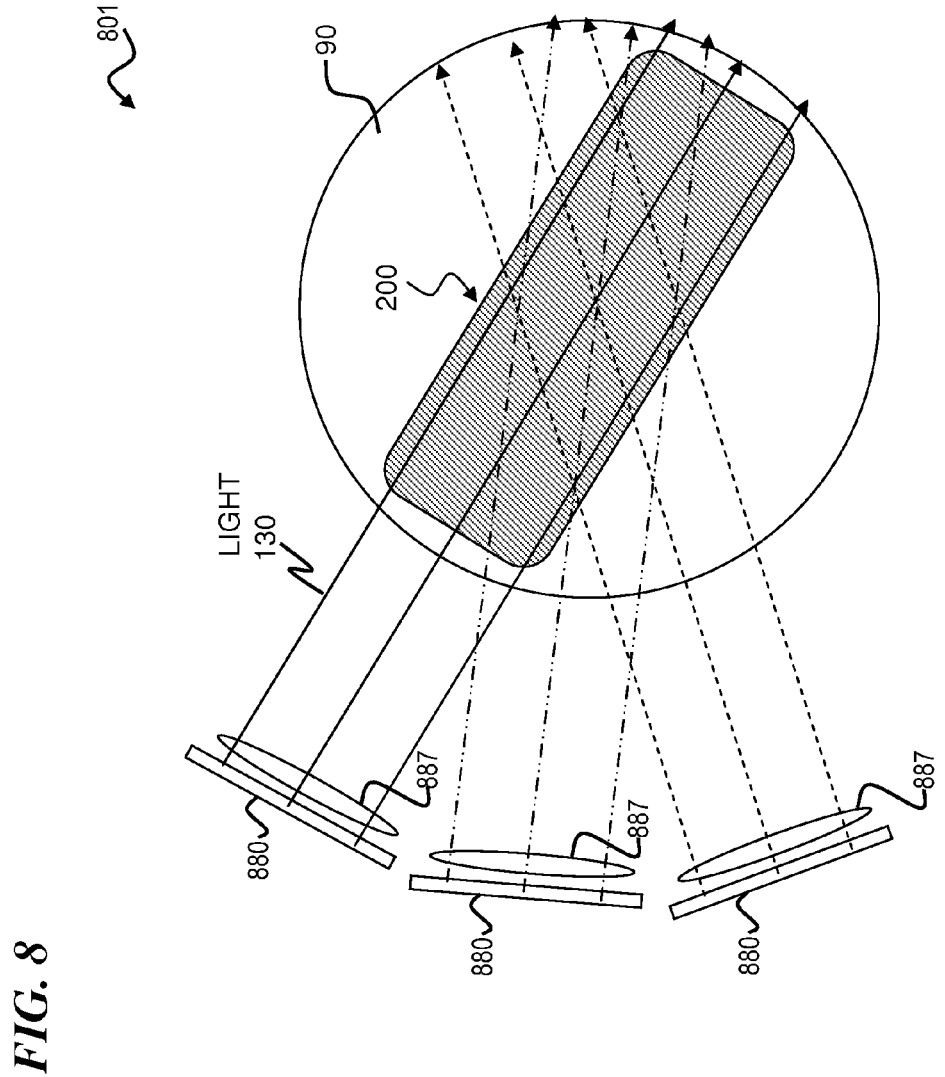
FIG. 8 is top cross-section view of a multiple element external light source subsystem 801.

FIG. 8 is a top cross-section view of an external light source 180, which in some embodiments of the present invention is a multiple-light-emitter subsystem 801. In some embodiments, the multiple-light-emitter subsystem includes a plurality of light emitters 880. In some embodiments, each of the plurality of light emitters 880 includes a two-dimensional array of vertical-cavity surface-emitting lasers (VCSEL-array) that forms an IR stimulator, which provides IR light 130 into the eye 90. In some embodiments, the plurality of light emitters is arranged as a single horizontal row of emitters, wherein the row is located so that images projected from the emitters fall on the desired portion of the retina of the patient's eye.

In some embodiments, the present invention provides a vision system to aid in the treatment of a vision problem of an eye of a person, wherein the eye has a retina having at least one functional nerve layer, wherein an ocular implant is implanted in the eye of the person, and wherein at least part of the vision system is immediately in front of the eye of the person, the vision system including: at least one imager that obtains a temporal sequence of images and converts the sequence of images into digital-image signals; an image-processing unit that generates a series of laser-driving signals based on the digital-image signals; and a laser unit that receives the laser-driving signals and generates pulsed infrared-light (IR) nerve-stimulation laser signals, and directs the pulsed IR nerve-stimulation laser signals into the ocular implant in the eye of the person, wherein the ocular implant transmits the IR nerve-stimulation laser signals through an inner portion of the eye and onto the at least one functional nerve layer of the retina, and wherein the IR nerve-stimulation laser signals produce optical nerve action potentials directly in nerve cells other than rods or cones, in order to produce a vision sensation to the person. In some embodiments, the ocular implant is used to provide a transparent path for the nerve-stimulation signals that are at wavelengths that are substantially absorbed by the cornea, aqueous humor, lens and/or vitreous humor in the eye. In some other embodiments, the present invention omits the ocular implant and generates pulsed light nerve-stimulation laser signals at one or more wavelengths at which the cornea, aqueous humor, lens and vitreous humor are all relatively highly transparent but at which the nerve tissue at the back of the eye is sufficiently absorbent to be optically stimulated to trigger a nerve action potential (in some embodiments, the wavelength(s) are infrared (e.g., between about 700 nm and about 1400 nm), while in other embodiments, one or more visible or ultraviolet wavelengths are used to trigger nerve action potential signals in nerve cells in the eye that are between the rod cells and the optic nerve and/or to trigger nerve action potential signals in nerve cells in the eye that are between the cone cells and the optic nerve.

In some embodiments of the system, the laser unit includes at least one array of infrared (IR) vertical-cavity surface-emitting lasers (VCSELs) having output wavelengths between about 1800 and about 1900 nm, and wherein the at least one array of VCSELs are included in a wearable headpiece.

In some embodiments of the system, the at least one image-gathering unit obtains a temporal sequence of pairs of images of three-dimensional (3-D) scenes, wherein the image-processing unit generates a different series of laser-driving signals for each eye of a person, and wherein the at least one array of lasers generates different infrared-light (IR) nerve-stimulation signals directed into each of both eyes of the person (i.e., one set of IR nerve-stimulation signals that are projected into the user's left-hand eye trigger nerve signals that convey a left-hand-eye visual scene to the user's brain, while the other set of IR nerve-stimulation signals that are projected into the user's right-hand eye trigger nerve signals that convey a right-hand-eye visual scene to the user's brain), in order to produce a 3-D vision sensation to the person.

Some embodiments of the system further include an eye-position sensor, wherein the image-processing unit adjusts the generated series of laser-driving signals to adjust positions of the stimulation emitters based on the current position(s) of the person's eye(s) for each of a plurality of successive times and positions of the person's eye(s).

In some embodiments of the system, the image-processing unit preprocesses the sequence of images (i.e., the sequence of frames) to perform at least part of the image processing that normally occurs in the layers of the retina before image-processing unit generates the series of laser-driving signals based on the digital-image signals. In some such embodiments, the image-processing unit preprocesses the sequence of images to determine edges on objects and generates the series of laser-driving signals to stimulate edge-detecting nerves in the retina. In some embodiments, the image-processing unit preprocesses the sequence of images to determine areas of increased brightness and generates the series of laser-driving signals to stimulate increased-brightness-detecting nerves in the retina. In some embodiments, the image-processing unit preprocesses the sequence of images to determine areas of decreased brightness and generates the series of laser-driving signals to stimulate decreased-brightness-detecting nerves in the retina.

In some embodiments of the system, the image-processing unit generates a series of laser-driving signals based on motion of an object in a series of the digital-image frames received over a period of time and generates the series of laser-driving signals that stimulate the nerves of the retina that detect motion.

In some embodiments of the system, the image-processing unit that generates a series of laser-driving signals based on the digital-image signals received over a period of time and generates the series of laser-driving signals modified to ensure nerves in the retina are not overheated by IR laser signals.

Some embodiments of the system further include the ocular implant implanted in the eye of the person.

In some embodiments, the present invention includes a vision system to aid in the treatment of a vision problem of an eye of a person, where the eye has a retina having at least one functional nerve layer, an ocular implant is implanted in the eye of the person and at least part of the vision system is immediately in front of the eye of the person. The vision system includes at least one imager that obtains a temporal sequence of images of a scene and converts the sequence of images into digital-image signals, an image-processing unit that is operatively coupled to the imager, that processes the digital-image signals, and that generates a series of optical-source-driving signals based on the digital-image signals, and an optical source that receives the optical-source-driving signals and generates pulsed infrared-light (IR) nerve-stimulation optical signals, and directs the pulsed IR nerve-stimulation optical signals into the ocular implant in the eye of the person. In some embodiments, the ocular implant transmits the IR nerve-stimulation optical signals through an inner portion of the eye and onto the at least one functional nerve layer of the retina, and the IR nerve-stimulation optical signals produce optical nerve action potentials directly in nerve cells other than rods or cones, in order to produce a vision sensation to the person.

Some embodiments omit the ocular implant, and some such embodiments use one or more visible light wavelengths that are directed into the eye of the person, in order to stimulate working portions of the retina to generate nerve action potentials that are sent to the brain for a vision sensation. Such a system can be useful for restoring vision to a person who has had a torn retina reattached but the retina pieces are no longer located at correct places in the eye, in which case the remapping functionality of the present invention can map pieces of a received camera image to locations on the retina pieces in their reattached positions, and project the remapped image into the eye. For example, if a torn retina were reattached to the back of the eye with a gap between two edges, the portions of a normal image formed by the lens of the eye that landed on the gap would not be sensed or seen, but the present invention can split portions of the received camera image and remap to the locations of the retina and avoid losing image in the gap. These embodiments are useful for improving vision for other defects or injuries that would benefit from remapping a received image to other patterns such that the light-sensitive regions of the patients' eye(s) receive the various pieces of the image as remapped by the image processor of the present invention. In some such embodiments, no infrared signals are projected into the eye, but rather a visible image of remapped portions of the scene captured by video cameras of the present invention.

In some embodiments, the optical unit includes at least one array of infrared (IR) vertical-cavity surface-emitting lasers (VCSELs) having output wavelengths between about 1800 and about 1900 nm. In some embodiments, the at least one array of VCSELs are included in a wearable headpiece.

In some embodiments, the at least one image-gathering unit vision system of the present invention obtains a temporal sequence of pairs of images of three-dimensional (3-D) scenes, the image-processing unit generates a different series of laser-driving signals for each eye of a person, and the at least one array of lasers generates different 3-D infrared-light (IR) nerve-stimulation signals directed into each of both eyes of the person, in order to produce a 3-D vision sensation to the person.

The vision system further includes, in some embodiment, an eye-position sensor used by the image-processing unit to adjust the generated series of optical-driving signals based on a current position of the person's eye.

In some embodiments, the image-processing unit preprocesses the sequence of images to perform at least part of the image processing that normally occurs in the layers of the retina before image-processing unit generates the series of optical-driving signals based on the digital-image signals. In other embodiments, the image-processing unit preprocesses the sequence of images to determine edges on objects and generates the series of optical-driving signals to stimulate edge-detecting nerves in the retina.

The present invention further includes the ocular implant implanted in the eye of the person, in some embodiments.

In some embodiments, the image-processing unit generates a series of laser-driving signals based on motion of an object in a series of the digital-image frames received over a period of time and generates the series of laser-driving signals that stimulate the nerves of the retina that detect motion.

In some embodiments, the image-processing unit generates a series of laser-driving signals based on the digital-image signals received over a period of time and generates the series of laser-driving signals modified to ensure nerves in the retina are not overheated by IR laser signals.

In some embodiments, the image-processing unit identifies an edge of a contiguous area in the scene based on a plurality of pixels of the area, and the optical-source-driving signals are pulsed signals configured to directly trigger nerve action potentials on an edge-detection nerve. In some embodiments, the image-processing unit identifies a line in the scene based on a plurality of pixels in the scene, and n the optical-source-driving signals are pulsed signals configured to directly trigger nerve action potentials on a line-detection nerve. In some embodiments, the image-processing unit identifies motion in the scene based on a plurality of pixels in a plurality of frames of the scene, and the optical-source-driving signals are pulsed signals configured to directly trigger nerve action potentials on a motion-detection nerve.

In other embodiments, the image processing unit identifies a first pattern in the scene based on a plurality of pixels in one or more frames in the scene, and based on the first pattern, generates optical-source-driving pulsed signals configured to directly trigger nerve action potentials on one or more excitatory nerves, and the image processing unit identifies a second pattern in the scene based on a plurality of pixels in one or more frames in the scene, and based on the second pattern, generates optical-source-driving pulsed signals configured to directly trigger nerve action potentials on one or more inhibitory nerves.

In some embodiments, the patterns in the scene are determined by a pattern-recognition algorithm such as described in U.S. Pat. No. 4,504,970 issued Mar. 12, 1985, titled "Training Controller for Pattern Processing System"; U.S. Pat. No. 4,541,115 issued Sep. 10, 1985, titled "Pattern Processing System"; U.S. Pat. No. 4,550,431 issued Oct. 29, 1985, titled "Address Sequencer for Pattern Processing System"; U.S. Pat. No. 4,551,850 issued Nov. 5, 1985, titled "Response Detector for Pattern Processing System"; U.S. Pat. No. 5,473,707 issued Dec. 5, 1995, titled "Pattern Processing System with Weighted Training Codes"; and/or U.S. Pat. No. 5,473,708 issued Dec. 5, 1995, titled "Pattern Processing System Using Minimum Length Address Loops"; each of which is incorporated herein by reference in its entirety. In some embodiments, the patterns determined from the scene are used to stimulate particular nerves or sets of nerves that would normally be triggered by visual stimulation by corresponding patterns if the eyes were functioning normally.

In some embodiments of the present invention, the image-processing unit is configured to transmit a sequential set of optical signals onto a patient's retina through the ocular implant, determine the patient's perceived visual response to the optical signals, and empirically produce a retinal map by correlating the perceived responses to the sequential set of optical-signal stimuli.

In some embodiments of the present invention, the image-processing unit is configured to transmit a sequential set of optical signals onto a patient's retina through the ocular implant, determine the patient's nerve-action-potential responses to the optical signals, and empirically produce a retinal map by correlating the perceived responses to the sequential set of optical-signal stimuli. In some such embodiments, the nerve-action-potential responses are detected optically, such as by the systems and methods described in U.S. Patent Publication No. 2010/0016732 (U.S. patent application Ser. No. 12/505,462) filed on Jul. 17, 2009, titled "Method and Apparatus for Neural-Signal Capture to Drive Neuroprostheses or Control Bodily Function," which is incorporated herein by reference.

In some embodiments, the image-processing unit is configured to transmit a sequential set of optical signals onto a patient's retina through the ocular implant, determine the patient's perceived visual response to the optical signal, and empirically produce a set of temporal and spatial optical signal patterns that when transmitted through the ocular implant directly trigger nerve action potentials that result in the visual perception of a line by the patient. In some embodiments, the image-processing unit is further configured to transmit a sequential set of optical signals onto a patient's retina through the ocular implant, determine the patient's perceived visual response to the optical signal, and empirically produce a set of temporal and spatial optical signal patterns that when transmitted through the ocular implant directly trigger nerve action potentials that result in the visual perception of an edge by the patient. In some embodiments, the image-processing unit is further configured to transmit a sequential set of optical signals onto a patient's retina through the ocular implant, determine the patient's perceived visual response to the optical signal, and empirically produce a set of temporal and spatial optical signal patterns that when transmitted through the ocular implant directly trigger nerve action potentials that result in the visual perception of motion by the patient In some embodiments, the present invention is a method to aid in the treatment of a vision problem of an eye of a person, where the eye has an anteroposterior axis extending from the eye's anterior surface to the eye's fovea. In some embodiments, the method includes forming an infrared (IR)-transparent optical path inside the person's eye, imaging a temporal sequence of images of a scene and converting the sequence of images into digital-image signals, generating a series of optical-source-driving signals based on the digital-image signals, receiving the optical-source-driving signals and generating pulsed infrared-light (IR) nerve-stimulation optical signals, and directing the pulsed IR nerve-stimulation optical signals into the ocular implant in the eye of the person, where the ocular implant transmits the IR nerve-stimulation optical signals through an inner portion of the eye and onto the at least one functional nerve layer of the retina, and the IR nerve-stimulation optical signals produce optical nerve action potentials directly in nerve cells other than rods or cones, in order to produce a vision sensation to the person.

In some embodiments, the method further includes outputting optical signals from a laser unit wherein the laser unit includes at least one array of infrared (IR) vertical-cavity surface-emitting lasers (VCSELs) having output wavelengths between about 1800 and about 1900 nm and including the at least one array of VCSELs in a wearable headpiece.

In other embodiments, imaging the scene includes obtaining a temporal sequence of pairs of images of three-dimensional (3-D) scenes, where the image-processing unit generates a different series of optical-driving signals for each eye of a person and different 3-D infrared-light (IR) nerve-stimulation signals are directed into each of both eyes of the person, in order to produce a 3-D vision sensation to the person.

In some embodiments, further includes adjusting the generated series of laser-driving signals based on a current position of the person's eye, wherein the current position of the person's eye is determined by an eye-position sensor.

The present invention, in some embodiments, includes preprocessing the sequence of images to perform at least part of the image processing that normally occurs in the layers of the retina before image-processing unit generates the series of optical-driving signals based on the digital-image signals. In other embodiments, the method includes preprocessing the sequence of images to determine edges on objects and generating the series of optical-driving signals to stimulate edge-detecting nerves in the retina.

In some embodiments, the method includes implanting the ocular implant in the eye of the person.

In some embodiments, the present invention includes generating a series of optical-driving signals based on motion of an object in a series of the digital-image frames received over a period of time and generating the series of optical-driving signals that stimulate the nerves of the retina that detect motion.

In some embodiments, the method includes generating a series of optical-driving signals based on the digital-image signals received over a period of time and generating the series of optical-driving signals modified to ensure nerves in the retina are not overheated by IR laser signals.

In some embodiments, the present invention includes identifying an edge of a contiguous area in the scene based on a plurality of pixels of the area, and generating optical-source-driving pulsed signals configured to directly trigger nerve action potentials on an edge-detection nerve. In some embodiments, the method further includes identifying a line in the scene based on a plurality of pixels in the scene, and generating optical-source-driving pulsed signals configured to directly trigger nerve action potentials on a line-detection nerve. In some embodiments, the method further includes identifying motion in the scene based on a plurality of pixels in a plurality of frames of the scene, and generating optical-source-driving pulsed signals configured to directly trigger nerve action potentials on a motion-detection nerve.

In some embodiments, the present invention includes identifying a first pattern in the scene based on a plurality of pixels in one or more frames in the scene, generating optical-source-driving pulsed signals based on the first pattern and configured to directly trigger nerve action potentials on one or more excitatory nerves, identifying a second pattern in the scene based on a plurality of pixels in one or more frames in the scene, and generating optical-source-driving pulsed signals based on the second pattern and configured to directly trigger nerve action potentials on one or more inhibitory nerves.

In some embodiments, the method further includes transmitting a sequential set of optical signals onto a patient's retina through the ocular implant, determining the patient's perceived visual response to the optical signal, and empirically producing a retinal map by correlating the perceived responses to the sequential set of optical-signal stimuli.

In some embodiments, the present invention includes transmitting a sequential set of optical signals onto a patient's retina through the ocular implant, determining the patient's perceived visual response to the optical signal, and empirically producing a set of temporal and spatial optical signal patterns that when transmitted through the ocular implant directly trigger nerve action potentials that result in the visual perception of an edge by the patient. In some embodiments, the method includes transmitting a sequential set of optical signals onto a patient's retina through the ocular implant, determining the patient's perceived visual response to the optical signal, and empirically producing a set of temporal and spatial optical signal patterns that when transmitted through the ocular implant directly trigger nerve action potentials that result in the visual perception of a line by the patient. In some embodiments, the method includes transmitting a sequential set of optical signals onto a patient's retina through the ocular implant, determining the patient's perceived visual response to the optical signal, and empirically producing a set of temporal and spatial optical signal patterns that when transmitted through the ocular implant directly trigger nerve action potentials that result in the visual perception of motion by the patient.

In some embodiments, the present invention includes an apparatus to aid in the treatment of a vision problem of an eye of a person, where the eye has an anteroposterior axis extending from the eye's anterior surface to the eye's fovea. The apparatus includes a means for forming an optical path inside the person's eye, where the optical path is substantially transparent to at least some infrared wavelengths of light between about 1000 nm and about 2000 nm, where the optical path has a light-receiving anterior end closest to the eye's anterior surface and extends to a posterior end, where the posterior end is closer to the fovea than to the eye's anterior surface; and a means for shining the light.

In some embodiments, the means for forming the optical path further includes a means for transmitting to the posterior end more than half of infrared light having wavelengths between about 1800 and about 2000 nm that is incident on the anterior end.

In some embodiments, the means for forming the optical path includes poly(methyl methacrylate) (PMMA).

In some embodiments, the means for forming the optical path includes a means for forming a substantially cylindrical-shaped path of a transparent material from the anterior end to the posterior end, and wherein the posterior end of the transparent material has a diameter substantially equal to a diameter of the anterior end of the transparent material.

In some embodiments, the present invention provides an apparatus to aid in the treatment of a vision problem of an eye of a person, wherein the eye has an anteroposterior axis extending from the eye's anterior surface to the eye's fovea. The apparatus includes an ocular implant inside the person's eye; means for imaging a temporal sequence of images of a scene and for converting the sequence of images into digital-image signals; means for generating a series of optical-source-driving signals based on the digital-image signals; means for receiving the optical-source-driving signals and for generating pulsed infrared-light (IR) nerve-stimulation optical signals; and means for directing the pulsed IR nerve-stimulation optical signals into the ocular implant in the eye of the person, wherein the ocular implant transmits the IR nerve-stimulation optical signals through an inner portion of the eye and onto the at least one functional nerve layer of the retina, and wherein the IR nerve-stimulation optical signals produce optical nerve action potentials directly in nerve cells other than rods or cones, in order to produce a vision sensation to the person. In some embodiments, the means for imaging of the scene includes: means for obtaining a temporal sequence of pairs of images of three-dimensional (3-D) scenes; means for generating a different series of optical-driving signals for each eye of a person; and means for generating different 3-D infrared-light (IR) nerve-stimulation signals directed into each of both eyes of the person, in order to produce a 3-D vision sensation to the person.

Some embodiments further include means for adjusting the generated series of laser-driving signals based on a current position of the person's eye; and means for in the current position of the person's eye is determined by an eye-position sensor.

Some embodiments further include means for preprocessing the sequence of images to perform at least part of the image processing that normally occurs in the layers of the retina before generating the series of optical-driving signals based on the digital-image signals.

Some embodiments further include means for preprocessing the sequence of images to determine edges on objects and generating the series of optical-driving signals to stimulate edge-detecting nerves in the retina.

Some embodiments further include the ocular implant implanted in the eye of the person.

Some embodiments further include means for generating a series of optical-driving signals based on motion of an object in a series of the digital-image frames received over a period of time; and means for generating the series of optical-driving signals that stimulate the nerves of the retina that detect motion.

Some embodiments further include means for generating a series of optical-driving signals based on the digital-image signals received over a period of time; and means for generating the series of optical-driving signals modified to ensure nerves in the retina are not overheated by IR laser signals.

Some embodiments further include means for identifying an edge of a contiguous area in the scene based on a plurality of pixels of the area, and wherein the optical-source-driving signals are pulsed signals configured to directly trigger nerve action potentials on an edge-detection nerve.

Some embodiments further include means for identifying a line in the scene based on a plurality of pixels in the scene, and wherein the optical-source-driving signals are pulsed signals configured to directly trigger nerve action potentials on a line-detection nerve.

Some embodiments further include means for identifying motion in the scene based on a plurality of pixels in a plurality of frames of the scene, and wherein the optical-source-driving signals are pulsed signals configured to directly trigger nerve action potentials on a motion-detection nerve.

Some embodiments further include means for identifying a first pattern in the scene based on a plurality of pixels in one or more frames in the scene; means for generating optical-source-driving pulsed signals based on the first pattern and configured to directly trigger nerve action potentials on one or more excitatory nerves; means for identifying a second pattern in the scene based on a plurality of pixels in one or more frames in the scene; and means for generating optical-source-driving pulsed signals based on the second pattern and configured to directly trigger nerve action potentials on one or more inhibitory nerves.

Some embodiments further include means for transmitting a sequential set of optical signals onto a patient's retina through the ocular implant, determining the patient's perceived visual response to the optical signal, and empirically producing a retinal map by correlating the perceived responses to the sequential set of optical-signal stimuli.

Some embodiments further include means for transmitting a sequential set of optical signals onto a patient's retina through the ocular implant, determining the patient's perceived visual response to the optical signal, and empirically producing a set of temporal and spatial optical signal patterns that when transmitted through the ocular implant directly trigger nerve action potentials that result in the visual perception of an edge by the patient.

Some embodiments further include means for transmitting a sequential set of optical signals onto a patient's retina through the ocular implant, determining the patient's perceived visual response to the optical signal, and empirically producing a set of temporal and spatial optical signal patterns that when transmitted through the ocular implant directly trigger nerve action potentials that result in the visual perception of a line by the patient.

Some embodiments further include means for transmitting a sequential set of optical signals onto a patient's retina through the ocular implant, determining the patient's perceived visual response to the optical signal, and empirically producing a set of temporal and spatial optical signal patterns that when transmitted through the ocular implant directly trigger nerve action potentials that result in the visual perception of motion by the patient.

Some embodiments further include means for outputting optical signals from a laser unit wherein the laser unit includes at least one array of infrared (IR) vertical-cavity surface-emitting lasers (VCSELs) having output wavelengths between about 1800 and about 1900 nm, wherein the at least one array of VCSELs is in a wearable headpiece.

In some embodiments, the present invention includes a wearable system to aid in the treatment of a vision problem of a first eye of a person, wherein the first eye has a retina having at least one functional nerve layer, and wherein at least part of the system is immediately in front of the first eye of the person. This system includes at least one imager that obtains a temporal sequence of images of a scene and converts the sequence of images into digital-image signals; an eye-position detector that detects a direction of gaze of the first eye; an image-processing unit that is operatively coupled to the at least one imager, that processes the digital-image signals, and that generates a series of optical-source-driving signals based on the digital-image signals; an optical source that receives the optical-source-driving signals and generates optical signals; and an image-position moving unit that directs the optical signals into the first eye of the person, such that directions of the optical signals track changes in the direction of gaze of the first eye, in order to produce a vision sensation to the person.

In some embodiments of this wearable system, the optical source includes at least one array of infrared (IR) vertical-cavity surface-emitting lasers (VCSELs) having output wavelengths between about 1800 and about 1900 nm, and wherein the at least one array of VCSELs are included in a wearable headpiece.

In some embodiments of this wearable system, the optical source includes at least one display screen, and the image-position moving unit moves the screen based on the detected direction of gaze of the first eye.

In some embodiments of this wearable system, the optical source includes at least one laser and a MEMS-based projection system that scans light from the least one laser to form a projected image, and wherein the image-position moving unit moves the image based on the detected direction of gaze of the first eye.

Some embodiments of this wearable system further include an ocular implant implanted in the first eye of the person, wherein the optical source includes at least one infrared (IR) laser that generates pulsed IR nerve-stimulation optical signals, and a MEMS-based projection system that scans light from the pulsed IR nerve-stimulation optical signals to form a projected image, and wherein the image-position moving unit moves the image based on the detected direction of gaze of the first eye.

In some embodiments of this wearable system, the image-processing unit has a calibration mode configured to transmit a sequential set of test-and-calibration optical signals onto a patient's retina through the ocular implant and to determine the patient's perceived visual response to the optical signal, and to empirically produce a retinal map by correlating the perceived responses to the sequential set of optical-signal stimuli, and wherein the image-processing unit has a vision mode configured to remap image information from the imager based on the retinal map.

Some embodiments of this wearable system further include an ocular implant implanted in the first eye of the person, wherein the optical source includes at least one infrared-wavelength light source and at least one visible-wavelength light source and is configured to form a projected image having interleaved infrared-wavelength pixels and visible-wavelength light pixels, and wherein the image-processing unit generates a series of optical-source-driving signals to control the at least one infrared-wavelength light source and the at least one visible-wavelength light source based on the digital-image signals.

In some embodiments, the present invention provides a method to aid in the treatment of a vision problem of a first eye of a person, wherein the first eye has an optical path extending along an anteroposterior axis extending from the first eye's anterior surface to the first eye's interior posterior surface. This method includes imaging a temporal sequence of images of a scene and converting the sequence of images into digital-image signals; generating a first series of optical-source-driving signals based on the digital-image signals; detecting a direction of gaze of the first eye and generating a first gaze-direction indication; receiving the first optical-source-driving signals and generating optical signals to form a first image; and moving the first image and directing the optical signals into the optical path in the first eye of the person in a direction based in the first gaze-direction indication, wherein the optical path transmits the optical signals through an inner portion of the first eye and onto the at least one functional nerve layer of the retina, and wherein the optical signals produce optical nerve action potentials in order to produce a vision sensation to the person.

In some embodiments of the method, the receiving of the optical-source-driving signals and the generating of the optical signals further includes outputting pulsed infrared-light (IR) nerve-stimulation optical signals from a laser unit, wherein the laser unit includes at least one array of infrared (IR) vertical-cavity surface-emitting lasers (VCSELs) having output wavelengths between about 1800 and about 1900 nm; and including the at least one array of IR VCSELs in a wearable headpiece.

Some embodiments of this method further include detecting a direction of gaze of a second eye of the person and generating a second gaze-direction indication; generating a second series of optical-source-driving signals based on the digital-image signals; detecting a direction of gaze of the second eye and generating a second gaze-direction indication; receiving the second optical-source-driving signals and generating optical signals to form a second image; and moving the second image and directing the optical signals into the optical path in the second eye of the person in a direction based in the second gaze-direction indication, wherein the optical path transmits the optical signals through an inner portion of the second eye and onto the at least one functional nerve layer of the retina, and wherein the optical signals produce optical nerve action potentials in order to produce a vision sensation to the person.

In some embodiments of the method, the generating of the optical signals further includes adjusting the generated series of optical-source-driving signals based on a current position of the person's eye as indicated by the first gaze-direction indication.

In some embodiments of the method, the generating of the optical signals to form the first image further includes generating laser light and using a MEMS-based projection system to scan light from the laser light to form a first projected image, and wherein the moving of the first image moves the first projected image based on the first gaze-direction indication.

In some embodiments of the method, the generating of the optical signals further includes outputting pulsed infrared-light (IR) nerve-stimulation optical signals from a laser unit, wherein the laser unit includes at least one array of infrared (IR) vertical-cavity surface-emitting lasers (VCSELs) having output wavelengths between about 1800 and about 1900 nm; and the method further includes implanting an ocular implant in the eye of the person, wherein the ocular implant is more transparent to IR wavelengths between about 1800 and about 1900 nm than is aqueous humor in the eye and than is vitreous humor in the eye.

Some embodiments further include transmitting a sequential set of optical signals onto a patient's retina through the ocular implant, determining the patient's perceived visual response to the sequential set of optical signals, and empirically producing a retinal map of retinal sensitivity by correlating the perceived responses to the sequential set of optical-signal stimuli.

In some embodiments, the present invention provides an apparatus to aid in the treatment of a vision problem of a first eye of a person, wherein the first eye has an optical path extending along an anteroposterior axis extending from the eye's anterior surface to the first eye's fovea and retina. This apparatus includes means for imaging a temporal sequence of images of a scene and for converting the sequence of images into digital-image signals; means for generating a series of optical-source-driving signals based on the digital-image signals; means for detecting a direction of gaze of the first eye and generating a first gaze-direction indication; means for receiving the optical-source-driving signals and for generating optical signals to form an image; and means for moving the image and directing the optical signals into the optical path the eye of the person in a direction based in the gaze-direction indication, wherein the optical path transmits the optical signals through an inner portion of the eye and onto the at least one functional nerve layer of the retina, and wherein the optical signals produce optical nerve action potentials in order to produce a vision sensation to the person.

In some embodiments, the means for receiving the optical-source-driving signals and the means for generating the optical signals further include means for outputting pulsed infrared-light (IR) nerve-stimulation optical signals from a laser unit, wherein the laser unit includes at least one array of infrared (IR) vertical-cavity surface-emitting lasers (VCSELs) having output wavelengths between about 1800 and about 1900 nm; and means for including the at least one array of IR VCSELs in a wearable headpiece.

In some embodiments, the means for generating the optical signals further includes means for forming a visible-wavelength image on each of two display screens, wherein the means for directing of the optical signals into the optical path in the eye of the person further includes means for moving each display screen to remain oriented along and substantially perpendicular to the anteroposterior axis of each respective eye, and the apparatus further includes means for adjusting the generated series of laser-driving signals based on a current position of each of the person's eyes, wherein the means for detecting the direction of gaze of the eye includes means for sensing a position of the person's eye.

In some embodiments, the means for receiving the optical-source-driving signals and for generating optical signals to form the first image further include means for generating laser light and MEMS-based means for scanning the laser light from the means for generating laser light to form the first image, and wherein the means for moving moves the first image based on the first gaze-direction indication.

Some embodiments further include means for transmitting a sequential set of optical signals onto the person's retina through the ocular implant, means for determining the patient's perceived visual response to the sequential set of optical signals, and means for empirically producing a retinal map of retinal sensitivity by correlating the perceived responses to the sequential set of optical-signal stimuli.

Some embodiments further include an ocular implant implanted in the eye of the person, wherein the ocular implant is more transparent to IR wavelengths between about 1800 and about 1900 nm than is aqueous humor in the eye and than is vitreous humor in the eye.

Some embodiments further include means for outputting optical signals from a laser unit wherein the laser unit includes at least one array of infrared (IR) vertical-cavity surface-emitting lasers (VCSELs) having output wavelengths between about 1800 and about 1900 nm, wherein the at least one array of VCSELs is in a wearable headpiece.

As discussed in par. 55 of Ser. No. 11/257,793, in some embodiments, a laser diode emitting light with a 1.87-micron wavelength stimulates nerves. This wavelength is important because devices capable of generating this wavelength are more available than longer mid-IR wavelengths. In some embodiments, laser-diode light of a 2.1-micron wavelength is used for nerve stimulation. Laser diodes that emit 2.1-micron-wavelength light are currently in research and would most likely work as well as other wavelengths, since this wavelength, when generated by a lamp-pumped solid-state laser, has been shown to be effective in stimulating nerves. In some embodiments, a laser-diode device (having one or more emitters) outputs light that is used for nerve stimulation, wherein the light has a wavelength of between about 1.5 microns and about 6 microns; in various embodiments, for example, the wavelength is in the far infrared at about 1.5 microns, or about 1.51 microns, about 1.52 microns, about 1.53 microns, about 1.54 microns, about 1.55 microns, about 1.56 microns, about 1.57 microns, about 1.58 microns, about 1.59 microns, about 1.6 microns, about 1.61 microns, about 1.62 microns, about 1.63 microns, about 1.64 microns, about 1.65 microns, about 1.66 microns, about 1.67 microns, about 1.68 microns, about 1.69 microns, about 1.7 microns, about 1.71 microns, about 1.72 microns, about 1.73 microns, about 1.74 microns, about 1.75 microns, about 1.76 microns, about 1.77 microns, about 1.78 microns, about 1.79 microns, about 1.8 microns, about 1.81 microns, about 1.82 microns, about 1.83 microns, about 1.84 microns, about 1.85 microns, about 1.86 microns, about 1.87 microns, about 1.88 microns, about 1.89 microns, about 1.9 microns, about 1.91 microns, about 1.92 microns, about 1.93 microns, about 1.94 microns, about 1.95 microns, about 1.96 microns, about 1.97 microns, about 1.98 microns, about 1.99 microns, about 2.0 microns, about 2.01 microns, about 2.02 microns, about 2.03 microns, about 2.04 microns, about 2.05 microns, about 2.06 microns, about 2.07 microns, about 2.08 microns, about 2.09 microns, about 2.1 microns, about 2.11 microns, about 2.12 microns, about 2.13 microns, about 2.14 microns, about 2.15 microns, about 2.16 microns, about 2.17 microns, about 2.18 microns, about 2.19 microns, about 2.2 microns, about 2.21 microns, about 2.22 microns, about 2.23 microns, about 2.24 microns, about 2.25 microns, about 2.26 microns, about 2.27 microns, about 2.28 microns, about 2.29 microns, about 2.3 microns, about 2.31 microns, about 2.32 microns, about 2.33 microns, about 2.34 microns, about 2.35 microns, about 2.36 microns, about 2.37 microns, about 2.38 microns, about 2.39 microns, about 2.4 microns, about 2.5 microns, about 2.6 microns, about 2.7 microns, about 2.8 microns, about 2.9 microns, about 3 microns, about 3.1 microns, about 3.2 microns, about 3.3 microns, about 3.4 microns, about 3.5 microns, about 3.6 microns, about 3.7 microns, about 3.8 microns, about 3.9 microns, about 4 microns, about 4.1 microns, about 4.2 microns, about 4.3 microns, about 4.4 microns, about 4.5 microns, about 4.6 microns, about 4.7 microns, about 4.8 microns, about 4.9 microns, about 5 microns, about 5.1 microns, about 5.2 microns, about 5.3 microns, about 5.4 microns, about 5.5 microns, about 5.6 microns, about 5.7 microns, about 5.8 microns, about 5.9 microns, or about 6.0 microns, or, in other embodiments, in ranges between any two of the above values. In other embodiments, an LED having output wavelengths centered in one of these ranges is used as a source of light to stimulate nerves.

As discussed in par. 99 of Ser. No. 12/191,301, in some embodiments, the present invention provides a VCSEL array configured to output light pulses capable of optically stimulating neural tissue (e.g., cochlear nerve tissue, deep brain tissue, white brain matter tissue, gray brain matter tissue, spinal cord tissue, cardial nerve tissue, central nervous system nerve tissue, olfactory nerve tissue, optic nerve tissue, nerve bundles and the like). In some embodiments, the stimulating lights pulses have a wavelength that results in the appropriate penetration depth for effective stimulation of the tissue of interest without causing tissue damage (e.g., in some embodiments, the wavelength of stimulating light pulses is in the range of about 1.8 microns to about 2.2 microns, in some embodiments, the wavelength of stimulating light pulses is in the range of about 1.85 microns to about 2.0 microns, in some embodiments, the wavelength of stimulating light pulses is about 1.87 microns, in some other embodiments the wavelength of stimulating light pulses is in the range of about 4.0 microns to about 5.0 microns, in some other embodiments the wavelength of stimulating light pulses is in the range of about 4.2 microns to about 4.8 microns, in some other embodiments the wavelength of stimulating light pulses is in the range of about 4.4 microns to about 4.6 microns).

As discussed in U.S. patent application Ser. No. 13/204,610, in some embodiments, one or both ends of the image pipe are shaped to focus the externally generated stimulator-array signals on the retina and fovea. In some embodiments, the present invention includes an external two-dimensional array VCSEL-array IR stimulator providing IR light into the anterior end of the ocular implant. In other embodiments of any of the embodiments of the present invention, other IR light sources are used, such as LED array emitters, or one or more single IR light sources that project light to an array modulator such as one or more grating light valves (for example, as described in U.S. Pat. No. 7,177,081 titled "High Contrast Grating Light Valve Type Device,") and/or one or more digital light projector devices (such as described in U.S. Pat. No. 4,566,935 issued to Hornbeck on Jan. 28, 1986, titled "Spatial light modulator and method," or U.S. Pat. No. 7,776,631 titled "MEMS Device and Method of Forming a MEMS Device,"), wherein the array light modulator provides a modulated nerve-stimulation signal to each of a plurality of locations on the patient's retina via the ocular implant. In yet other embodiments, any other suitable sources of IR stimulation light are used, including light sources emitting from a plurality of heights from their substrates (such as LED arrays or MEMS minors configured to focus at a plurality of depths in the nerves of the retina).

Although the various figures and embodiments described herein explicitly show some combinations of the individual features of the present invention in combination, other embodiments include any subset or all of the features in combination, and it is sepecifically contemplated that features described in one embodiment herein ma be added to other embodiments, and that not all features of any one described embodiments are required for other variations of that embodiment.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A wearable system to aid in treating a vision problem of a first eye of a person, wherein the first eye has a retina having at least one functional nerve layer, and wherein at least part of the system is immediately in front of the first eye of the person, the system comprising:
    at least one imager that obtains a temporal sequence of images of a scene and converts the sequence of images into digital-image signals, the at least one imager having a field of view facing away from the person;
    an eye-position detector that detects a direction of gaze of the first eye;
    a field-of-view controller configured to direct the field of view of the at least one imager in response to the direction of gaze of the first eye detected by the eye-position detector;
    an image-processing unit that is operatively coupled to the at least one imager, wherein the image-processing unit processes the digital-image signals and generates a series of optical-source-driving signals based on the digital-image signals;
    an optical source configured to receive the optical-source-driving signals and to generate and emit optical signals, wherein the optical signals have a wavelength between 1800 nm and 1900 nm and a pulse width between 1 microsecond and 8 milliseconds;
    an ocular implant configured to be implanted at least in part within the first eye of the person, wherein the ocular implant has a light-receiving anterior end closest to the first eye's anterior surface, and extends to a posterior end that is closer to the first eye's fovea than to the first eye's anterior surface; and
    an image-position moving unit configured to direct the optical signals into the ocular implant, such that directions of the optical signals follow changes in the direction of gaze of the first eye, wherein the ocular implant is configured to transmit the optical signals through an inner portion of the first eye and onto an at least one functional nerve layer of the first eye's retina, and wherein the optical signals produce nerve action potentials in order to produce a vision sensation to the person.

2. The system of claim 1, wherein the optical source includes at least one array of infrared (IR) vertical-cavity surface-emitting lasers (VCSELs), and wherein the at least one array of VCSELs are included in a wearable headpiece.

3. The system of claim 1, wherein the optical source includes at least one display screen, and the image-position moving unit moves the screen based on the detected direction of gaze of the first eye.

4. The system of claim 1, wherein the optical source includes at least one laser and a MEMS-based projection system that scans light from the least one laser to form a projected image, and wherein the image-position moving unit moves the image based on the detected direction of gaze of the first eye.

5. The system of claim 1, wherein the optical source includes at least one infrared (IR) laser that generates the optical signals, and a MEMS-based projection system that scans light from the optical signals to form a projected image, and wherein the image-position moving unit moves the image based on the detected direction of gaze of the first eye.

6. The system of claim 1,
    wherein the image-processing unit has a calibration mode configured to transmit a sequential set of test-and-calibration optical signals onto a patient's retina through the ocular implant, and to determine the patient's perceived visual response to the sequential set of optical signals, and to empirically produce a retinal map by correlating the perceived responses to the sequential set of optical signals, and wherein the image-processing unit has a vision mode configured to remap image information from the imager based on the retinal map.

7. The system of claim 1,
    wherein the optical source includes at least one infrared-wavelength light source and at least one visible-wavelength light source and is configured to form a projected image having interleaved infrared-wavelength pixels and visible-wavelength light pixels, and wherein the image-processing unit generates a series of optical-source-driving signals to control the at least one infrared-wavelength light source and the at least one visible-wavelength light source based on the digital-image signals.

8. The system of claim 1, wherein the field-of-view controller generates control signals configured to cause the at least one imager to move such that the at least one imager points in the direction of gaze of the first eye.

9. The system of claim 1, wherein the at least one imager includes a wide-angle lens camera, and wherein the field-of-view controller selects an image signal of the field of view from the wide-angle lens camera based on the direction of gaze of the first eye.

10. The system of claim 1, wherein the at least one imager includes a plurality of cameras pointed toward different directions in an environment surrounding the person, and wherein the field-of-view controller selects an image signal of the field of view from the plurality of cameras based on the direction of gaze of the first eye.

11. The system of claim 1, wherein the system has a plurality of different modes of operation that are selectable to enhance text recognition in a first mode and face recognition in a second mode.

12. The system of claim 1, wherein the posterior end of the ocular implant is within 2 mm of the first eye's retina.

13. A method to aid in treating a vision problem of a first eye of a person, wherein the first eye has an optical path extending along an anteroposterior axis extending from the first eye's anterior surface to the first eye's interior posterior surface, the method comprising:

provided the system of claim 1;

imaging a temporal sequence of images of a scene in the field of view and converting the sequence of images into digital-image signals;

generating a first series of optical-source-driving signals based on the digital-image signals;

detecting a direction of gaze of the first eye and generating a first gaze-direction indication, wherein the imaging includes directing the field of view for the scene in response to the first gaze-direction indication;

receiving the first optical-source-driving signals and generating and emitting the optical signals to form a first image;

implanting the ocular implant at least in part within the first eye of the person such that the ocular implant has a light-receiving anterior end closest to the first eye's anterior surface, and extends to a posterior end that is closer to the first eye's fovea than to the first eye's anterior surface;

and moving the first image and directing the optical signals into the implanted ocular implant in the first eye of the person in a direction based on the first gaze-direction indication, wherein the ocular implant transmits the optical signals through an inner portion of the first eye and onto an at least one functional nerve layer of the retina, and wherein the optical signals nerve action potentials in order to produce a vision sensation to the person.

14. The method of claim 13, the receiving of the optical-source-driving signals and the generating of the optical signals further comprising:

outputting the optical signals from a laser unit, wherein the laser unit includes at least one array of infrared (IR) vertical-cavity surface-emitting lasers (VCSELs); and including the at least one array of IR VCSELs in a wearable headpiece.

15. The method of claim 13, further comprising:

detecting a direction of gaze of a second eye of the person and generating a second gaze-direction indication;

generating a second series of optical-source-driving signals based on the digital-image signals;

detecting a direction of gaze of the second eye and generating a second gaze-direction indication;

receiving the second optical-source-driving signals and generating optical signals to form a second image; and moving the second image and directing the optical signals into the optical path in the second eye of the person in a direction based on the second gaze-direction indication, wherein the optical path transmits the optical signals through an inner portion of the second eye and onto the at least one functional nerve layer of the retina, and wherein the optical signals produce nerve action potentials in order to produce a vision sensation to the person.

16. The method of claim 13, wherein the generating of the optical signals further includes adjusting the generated series of optical-source-driving signals based on a current position of the person's eye as indicated by the first gaze-direction indication.

17. The method of claim 13, wherein the generating of the optical signals to form the first image further includes generating laser light and using a MEMS-based projection system to scan light from the laser light to form a first projected image, and wherein the moving of the first image moves the first projected image based on the first gaze-direction indication.

18. The method of claim 13, wherein the generating of the optical signals further includes outputting the optical signals from a laser unit, wherein the laser unit includes at least one array of infrared (IR) vertical-cavity surface-emitting lasers (VCSELs); and wherein the ocular implant is more transparent to the wavelength of the optical signals than is aqueous humor in the first eye and than is vitreous humor in the first eye.

19. The method of claim 18, further comprising:

transmitting a sequential set of optical signals onto a patient's retina through the ocular implant, determining the patient's perceived visual response to the sequential set of optical signals, and empirically producing a retinal map of retinal sensitivity by correlating the perceived responses to the sequential set of optical signals.

20. An apparatus to aid in treating a vision problem of a first eye of a person, wherein the first eye has an optical path extending along an anteroposterior axis extending from the first eye's anterior surface to the first eye's fovea and retina, the apparatus comprising:

means for imaging a temporal sequence of images of a scene and for converting the sequence of images into digital-image signals, the means for imaging having a field of view facing away from the person;

means for generating a series of optical-source-driving signals based on the digital-image signals;

means for detecting a direction of gaze of the first eye and generating a first gaze-direction indication;

means for directing a field of view of the means for imaging in response to the first gaze-direction indication;

means for receiving the optical-source-driving signals and for generating and emitting optical signals to form an image, wherein the means for generating and emitting optical signals include an optical source configured to emit the optical signals at a wavelength between 1800 nm and 1900 nm and with a pulse width between 1 microsecond and 8 milliseconds;

an ocular implant configured to be implanted at least in part within the first eye of the person, wherein the ocular implant has a light-receiving anterior end closest to the first eye's anterior surface, and extends to a posterior end, wherein the posterior end is closer to the first eye's fovea than to the first eye's anterior surface; and means for moving the image and directing the optical signals into the ocular implant in a direction based on the first gaze-direction indication, wherein the ocular implant is configured to transmit the optical signals through an inner portion of the first eye and onto an at least one functional nerve layer of the retina, and wherein the optical signals nerve action potentials in order to produce a vision sensation to the person.

21. The apparatus of claim 20, wherein the means for receiving the optical-source-driving signals and the means for generating the optical signals further include means for outputting the optical signals from a laser unit, wherein the laser unit includes at least one array of infrared (IR) vertical-cavity surface-emitting lasers (VCSELs); and means for including the at least one array of IR VCSELs in a wearable headpiece.

22. The apparatus of claim 20, wherein the means for generating the optical signals further includes means for forming a visible-wavelength image on each of two display screens, wherein the means for directing of the optical signals into the ocular implant in the eye of the person further includes means for moving each display screen to remain oriented along and substantially perpendicular to the antero-posterior axis of each respective eye, the apparatus further comprising:

means for adjusting the generated series of laser-driving signals based on a current position of each of the person's eyes, wherein the means for detecting the direction of gaze of the eye includes means for sensing a position of the person's eye.

23. The apparatus of claim 20, wherein the means for receiving the optical-source-driving signals and for generating optical signals to form the first image further include means for generating laser light and MEMS-based means for scanning the laser light from the means for generating laser light to form the first image, and wherein the means for moving moves the first image based on the first gaze-direction indication.

24. The apparatus of claim 20, further comprising:

means for transmitting a sequential set of optical signals onto the person's retina through the ocular implant;

means for determining the patient's perceived visual response to the sequential set of optical signals; and means for empirically producing a retinal map of retinal sensitivity by correlating the perceived responses to the sequential set of optical signals.

25. The apparatus of claim 20, wherein the ocular implant is more transparent to the wavelength of the optical signals than is aqueous humor in the first eye and than is vitreous humor in the first eye.

\* \* \* \* \*